(12) United States Patent
Atkinson et al.

(10) Patent No.: US 11,319,307 B2
(45) Date of Patent: *May 3, 2022

(54) 2,3-DIHYDROBENZOHURANS AS BROMODOMAIN INHIBITORS

(71) Applicant: GLAXOSMITHKLINE INTELLECTUAL PROPERTY (NO.2) LIMITED, Middlesex (GB)

(72) Inventors: Stephen John Atkinson, Stevenage (GB); Emmanuel Hubert Demont, Stevenage (GB); Lee Andrew Harrison, Stevenage (GB); Simon Christopher Cranko Lucas, Stevenage (GB); Alexander G. Preston, Stevenage (GB); Jonathan Thomas Seal, Stevenage (GB); Ian David Wall, Stevenage (GB); Robert J. Watson, Stevenage (GB); James Michael Woolven, Stevenage (GB)

(73) Assignee: GlaxoSmithKline Intellectual Property (No.2) Limited, Middlesex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/753,543

(22) PCT Filed: Oct. 4, 2018

(86) PCT No.: PCT/EP2018/076938
§ 371 (c)(1),
(2) Date: Apr. 3, 2020

(87) PCT Pub. No.: WO2019/068782
PCT Pub. Date: Apr. 11, 2019

(65) Prior Publication Data
US 2020/0291009 A1    Sep. 17, 2020

(30) Foreign Application Priority Data
Oct. 6, 2017 (GB) ..................... 1716392

(51) Int. Cl.
*C07D 413/12* (2006.01)
*C07D 307/80* (2006.01)
*C07D 405/12* (2006.01)
*C07D 407/12* (2006.01)
*A61K 45/06* (2006.01)

(52) U.S. Cl.
CPC ......... *C07D 413/12* (2013.01); *C07D 307/80* (2013.01); *C07D 405/12* (2013.01); *C07D 407/12* (2013.01); *A61K 45/06* (2013.01)

(58) Field of Classification Search
CPC ........................... C07D 307/80; C07D 413/12
See application file for complete search history.

(56) References Cited

U.S. PATENT DOCUMENTS 10,583,112 B2 * 3/2020 Atkinson ............. A61K 31/343
2015/0315207 A1 11/2015 Morales et al.

FOREIGN PATENT DOCUMENTS

| CN | 105 085 427 A | 11/2015 |
| WO | WO 2014/140077 A1 | 9/2014 |
| WO | WO 2014/164771 A1 | 10/2014 |
| WO | WO 2014/173241 A1 | 10/2014 |
| WO | WO 2017/050714 A1 | 3/2017 |

* cited by examiner

*Primary Examiner* — Golam M Shameem
(74) *Attorney, Agent, or Firm* — James K. Leonard

(57) ABSTRACT

The present invention relates to compounds of formula (I) and salts thereof, pharmaceutical compositions containing such compounds and to their use in therapy.

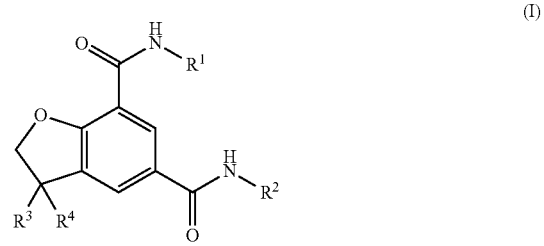

18 Claims, No Drawings

2,3-DIHYDROBENZOHURANS AS BROMODOMAIN INHIBITORS

This application is a § 371 of International Application No. PCT/EP2018/076938, filed 4 Oct. 2018, which claims the priority of GB 1716392.4, filed 6 Oct. 2017.

FIELD OF THE INVENTION

The present invention is directed to certain compounds which are bromodomain inhibitors, processes for their preparation, pharmaceutical compositions comprising the compounds and the use of the compounds or the compositions in the treatment of various diseases or conditions, for example acute or chronic autoimmune and/or inflammatory conditions, viral infections and cancer.

BACKGROUND TO THE INVENTION

The genomes of eukaryotic organisms are highly organised within the nucleus of the cell. The long strands of duplex DNA are wrapped around an octomer of histone proteins (most usually comprising two copies of histones H2A, H2B, H3 and H4) to form a nucleosome. This basic unit is then further compressed by the aggregation and folding of nucleosomes to form a highly condensed chromatin structure. A range of different states of condensation are possible, and the tightness of this structure varies during the cell cycle, being most compact during the process of cell division. Chromatin structure plays a critical role in regulating gene transcription, which cannot occur efficiently from highly condensed chromatin. The chromatin structure is controlled by a series of post translational modifications to histone proteins, notably histones H3 and H4, and most commonly within the histone tails which extend beyond the core nucleosome structure. These modifications include acetylation, methylation, phosphorylation, ubiquitinylation, SUMOylation. These epigenetic marks are written and erased by specific enzymes, which place the tags on specific residues within the histone tail, thereby forming an epigenetic code, which is then interpreted by the cell to allow gene specific regulation of chromatin structure and thereby transcription.

Histone acetylation is most usually associated with the activation of gene transcription, as the modification loosens the interaction of the DNA and the histone octomer by changing the electrostatics. In addition to this physical change, specific proteins recognise and bind to acetylated lysine residues within histones to read the epigenetic code. Bromodomains are small (~110 amino acid) distinct domains within proteins that bind to acetylated lysine residues commonly but not exclusively in the context of histones. There is a family of around 50 proteins known to contain bromodomains, and they have a range of functions within the cell.

The BET family of bromodomain containing proteins comprises 4 proteins (BRD2, BRD3, BRD4 and BRDT) which contain tandem bromodomains capable of binding to two acetylated lysine residues in close proximity, increasing the specificity of the interaction. Numbering from the N-terminal end of each BET protein the tandem bromodomains are typically labelled Binding Domain 1 (BD1) and Binding Domain 2 (BD2) (Chung et al, J Med. Chem., 2011, 54, 3827-3838).

Chan et al. report that BET bromodomain inhibition suppresses transcriptional responses to cytokine-Jak-STAT signalling in a gene-specific manner in human monocytes, which suggests that BET inhibition reduces inflammation partially through suppression of cytokine activity. (Chan et al., Eur. J. Immunol., 2015, 45: 287-297).

Klein et al. report that the bromodomain protein inhibitor I-BET151 suppresses expression of inflammatory genes and matrix degrading enzymes in rheumatoid arthritis synovial fibroblasts, which suggests a therapeutic potential in the targeting of epigenetic reader proteins in rheumatoid arthritis. (Klein et al., Ann. Rheum. Dis., 2014, 0:1-8).

Park-Min et al. report that I-BET151 that targets bromo and extra-terminal (BET) proteins that 'read' chromatin states by binding to acetylated histones, strongly suppresses osteoclastogenesis. (Park-Min et al. Nature Communications, 2014, 5, 5418).

PCT patent application PCT/EP2017/058049 discloses a series dibenzofuran derivatives as BET family bromodomain inhibitors.

SUMMARY OF THE INVENTION

The invention is directed to compounds of formula (I)

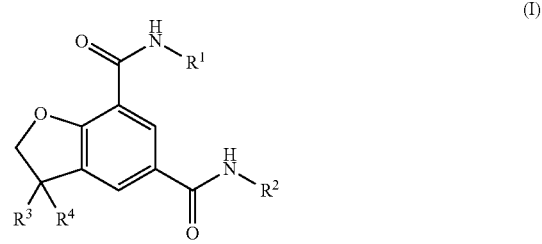

or a salt thereof
wherein:
$R^1$ is —$C_{1-3}$alkyl or cyclopropyl;
$R^2$ is —$C_{0-3}$alkyl-cycloalkyl, wherein the cycloalkyl group is optionally substituted with one, two or three $R^5$ groups which may be the same or different; or
$R^2$ is —$C_{0-4}$alkyl-heterocyclyl or —$(CH_2)_pO$-heterocyclyl wherein each heterocyclyl is optionally substituted by one or two $R^9$ groups which may be the same or different; or
$R^2$ is H, —$CH_3$, —$C_{2-6}$alkyl optionally substituted by up to five fluoro, —$C_{2-6}$alkylOR$^{13}$, —$C_{2-6}$alkylNR$^{11}$R$^{12}$, —$(CH_2)_mSO_2C_{1-3}$alkyl, —$(CH_2)_mSO_2NR^{11}R^{12}$, —$(CH_2)_mC(O)NR^{11}R^{12}$, —$(CH_2)_mCN$, —$(CH_2)_mCO_2R^{13}$, —$(CH_2)_mNHCO_2C_{1-4}$alkyl —$(CH_2)_mNHC(O)C_{1-4}$alkyl or —$(CH_2)_n$heteroaryl, wherein heteroaryl is optionally substituted by one or two $R^{14}$ groups which may be the same or different;
$R^3$ is phenyl optionally substituted with one, two or three R' groups which may be the same or different;
$R^4$ is —$CH_2OR^6$ or —$C_{1-3}$alkyl optionally substituted by up to three fluoro;
each $R^5$ is independently halo, —$C_{0-6}$alkyl-$R^8$, —O—$C_{2-6}$ alkyl-$R^8$, —CN or —$SO_2C_{1-3}$alkyl;
$R^6$ is —H or —$C_{1-3}$alkyl;
each R' is independently -halo, —$C_{1-4}$alkyl, —$C_{0-3}$alkyl-OR$^{10}$, —$C_{0-3}$alkyl-NR$^{15}$R$^{16}$, —$C_{0-3}$alkyl-CONR$^{15}$R$^{16}$, —CN or —$SO_2R^{17}$;
$R^8$ is —H, —OR$^{10a}$, —NR$^{18}$R$^{19}$ or heteroaryl;
each $R^9$ is independently halo, $C_{1-4}$alkyl, cyclopropyl, cyclobutyl, —$CH_2CF_3$, —$CH_2CHF_2$, —$CH_2CH_2F$, —$OCH_2CH_2OR^{13}$, —$C_{0-3}$alkylOR$^{13}$, —$C_{0-3}$alkylNR$^{11}$R$^{12}$, —NHCH$_2$CH$_2$OR$^{13}$, —NHCO$_2$R$^{13}$, oxo, —C(O)R$^{13}$, —C(O)OR$^{13}$ or —C(O)NR$^{11}$R$^{12}$;

$R^{10a}$ is —H, —$C_{1-3}$alkyl, —$C_{2-3}$alkylNR$^{11}$R$^{12}$ or —$C_{2-3}$alkylOH;

$R^{10}$ is —H, —$C_{1-3}$alkyl, —$C_{2-3}$alkylNR$^{15}$R$^{16}$ or —$C_{2-3}$alkylOH;

$R^{11}$ and $R^{12}$ are each independently selected from —H and —$C_{1-3}$alkyl; or $R^{11}$ and $R^{12}$ may join together with the nitrogen to which they are attached, to form a 4 to 7-membered heterocyclyl group optionally substituted by one or two substituents independently selected from —$C_{1-3}$alkyl, —OH and F;

$R^{13}$ is —H or —$C_{1-4}$alkyl;

each $R^{14}$ is independently halo, $C_{1-4}$alkyl, cyclopropyl, cyclobutyl or —OR$^{13}$;

$R^{15}$ and $R^{16}$ are each independently selected from —H and —$C_{1-3}$alkyl; or $R^{15}$ and $R^{16}$ may join together with the nitrogen to which they are attached, to form a 4 to 7-membered heterocyclyl group optionally substituted by one or two substituents independently selected from —$C_{1-3}$alkyl, —OH and F;

$R^{17}$ is —$C_{1-3}$alkyl or —NR$^{15}$R$^{16}$;

$R^{18}$ and $R^{19}$ are each independently selected from —H, —C(O)OC(CH$_3$)$_3$, —$C_{1-6}$alkyl, cycloalkyl, heterocyclyl, —$C_{2-3}$alkylNR$^{13}$COC$_{1-3}$alkyl, —$C_{2-3}$alkylNR$^{15}$R$^{16}$ and —$C_{2-3}$alkyl-O—$C_{1-3}$alkyl wherein the —$C_{1-6}$alkyl and cycloalkyl may be optionally substituted by one, two or three fluoro; or $R^{18}$ and $R^{19}$ may join together with the nitrogen to which they are attached, to form a 4 to 7-membered heterocyclyl group optionally substituted by one or two substituents independently selected from —$C_{1-3}$alkyl, —OH and F;

m is an integer selected from 2, 3 and 4;

p is an integer selected from 2, 3 and 4; and n is an integer selected from 0, 1, 2, 3 and 4.

Compounds of the invention have been shown to be bromodomain inhibitors, in particular BD2 selective and may be useful in the treatment of various diseases or conditions, for example acute or chronic auto-immune and/or inflammatory conditions, for example rheumatoid arthritis and cancer. Accordingly, the invention is further directed to pharmaceutical compositions comprising a compound of formula (I), or a pharmaceutically acceptable salt thereof. The invention is still further directed to methods of treatment of diseases or conditions associated therewith using a compound of formula (I) or a pharmaceutically acceptable salt thereof, or a pharmaceutical composition comprising a compound of formula (I) or a pharmaceutically acceptable salt thereof. The invention is yet further directed towards processes for the preparation of the compounds of the invention.

DETAILED DESCRIPTION OF THE INVENTION

Compounds of formula (I) and salts thereof are referred to herein as "compounds of the invention".

"BD2" refers to Binding Domain 2 of any of the BET family of proteins BRD2, BRD3, BRD4 or BRDT.

"Alkyl" refers to a saturated hydrocarbon chain having the specified number of carbon atoms. For example, the term "$C_{1-6}$alkyl" as used herein refers to a straight or branched alkyl group having from 1 to 6 carbon atoms, for example 1 to 3 carbon atoms. For example the term "$C_{0-3}$alkyl" refers to a straight or branched alkyl group having from 0 (i.e. is absent) to 3 carbon atoms, for example 0 to 2 carbon atoms. Representative branched alkyl groups have one, two or three branches. An alkyl group may form part of a chain, for example, —$C_{0-4}$alkyl-heterocyclyl refers to a straight or branched alkyl chain having from 0 (i.e. absent) to 4 carbon atoms linked to a heterocyclyl. "Alkyl" includes, but is not limited to, methyl, ethyl, n-propyl, n-butyl, iso-butyl, iso-propyl, t-butyl, pentyl and hexyl.

"Cycloalkyl" refers to a saturated hydrocarbon mono or bicyclic ring or a saturated spiro-linked bicyclic hydrocarbon ring, having 3, 4, 5, 6, 7, 8, 9 or 10 member atoms in the ring. Suitable examples of cycloalkyl include, but are not limited to, cyclopropyl, cyclobutyl, cyclopentyl, cyclohexyl, cycloheptanyl, spiro[3.3]heptanyl, bicycle[2,2,1]heptanyl, adamantyl and bicyclo[3.1.0]hexanyl. "$C_{3-7}$cycloalkyl" refers to a saturated hydrocarbon mono or bicyclic ring or a saturated spiro-linked bicyclic hydrocarbon ring, having 3, 4, 5, 6 or 7 member atoms in the ring. Examples of $C_{3-7}$cycloalkyl groups include, but are not limited to, cyclopropyl, cyclobutyl, cyclopentyl, cyclohexyl, cycloheptanyl and bicyclo[3.1.0]hexanyl.

"Enantiomeric excess" (ee) is the excess of one enantiomer over the other expressed as a percentage. In a racemic modification, since both enantiomers are present in equal amounts, the enantiomeric excess is zero (0% ee). However, if one enantiomer were enriched such that it constitutes 95% of the product, then the enantiomeric excess would be 90% ee (the amount of the enriched enantiomer, 95%, minus the amount of the other enantiomer, 5%).

"Enantiomerically enriched" refers to products whose enantiomeric excess (ee) is greater than zero. For example, "enantiomerically enriched" refers to products whose enantiomeric excess is greater than 50% ee, greater than 75% ee, and greater than 90% ee.

"Enantiomerically pure" as used herein refers to products whose enantiomeric excess is 99% or greater.

"Half-life" (or "half-lives") refers to the time required for half of a quantity of a substance to be converted to another chemically distinct species in vitro or in vivo.

"Halo" refers to a halogen radical, for example, fluoro, chloro, bromo, or iodo.

"Heteroaryl" refers to a monocyclic or bicyclic group having 5 or 6 member atoms, including 1, 2 or 3 heteroatoms independently selected from nitrogen, sulphur and oxygen, wherein at least a portion of the group is aromatic. The point of attachment to the rest of the molecule may be by any suitable carbon or nitrogen atom. Examples of "heteroaryl" groups include, but are not limited to, furanyl, thienyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl and triazinyl.

"Heteroatom" refers to a nitrogen, sulfur, or oxygen atom.

"Heterocyclyl" refers to a non-aromatic heterocyclic monocyclic or bicyclic ring system containing 4, 5, 6, 7, 8, 9 or 10 ring member atoms, including one heteroatom and optionally containing a further heteroatom selected from nitrogen, oxygen or sulphur. Examples of "heterocyclyl" groups include, but are not limited to, azetidinyl, oxetanyl, thietanyl, pyrrolidinyl, pyrrolinyl, pyrazolidinyl, pyrazolinyl, imidazolidinyl, imidazolinyl, oxazolinyl, thiazolinyl, tetrahydrofuranyl, dihydrofuranyl, 1,3-dioxolanyl, piperidinyl, piperazinyl, homopiperazinyl, tetrahydropyranyl, dihydropyranyl, tetrahydrothiopyranyl, 1,3-dioxanyl, 1,4-dioxanyl, 1,3-oxathiolanyl, 1,3-oxathianyl, 1,3-dithianyl, 1,4-oxathiolanyl, 1,4-oxathianyl, 1,4-dithianyl, morpholinyl, thiomorpholinyl, hexahydro-1H-1,4-diazepinyl, azabicylo[3.2.1]octyl, azabicylo[3.3.1]nonyl, azabicylo[4.3.0]nonyl, oxabicylo[2.2.1]heptyl, 1,1-dioxidotetrahydro-2H-thiopyranyl, 1,5,9-triazacyclododecyl, 3-oxabicyclo[3.1.0]hexanyl, 3-azabicyclo[3.1.0]hexanyl, (1r,5s)-3-oxabicyclo[3.1.0]

hexanyl and (1r,5s)-3-azabicyclo[3.1.0]hexanyl. "4 to 7-membered heterocyclyl" refers to a non-aromatic heterocyclic monocyclic or bicyclic ring system containing 4, 5, 6 or 7 ring member atoms, including one heteroatom and optionally containing a further heteroatom selected from nitrogen, oxygen or sulphur.

"Member atoms" refers to the atom or atoms that form a chain or ring. Where more than one member atom is present in a chain and within a ring, each member atom is covalently bound to an adjacent member atom in the chain or ring. Atoms that make up a substituent group on a chain or ring are not member atoms in the chain or ring.

"Substituted" in reference to a group indicates that a hydrogen atom attached to a member atom within a group is replaced. It should be understood that the term "substituted" includes the implicit provision that such substitution be in accordance with the permitted valence of the substituted atom and the substituent and that the substitution results in a stable compound (i.e. one that does not spontaneously undergo transformation such as rearrangement, cyclisation, or elimination). In certain embodiments, a single atom may be substituted with more than one substituent as long as such substitution is in accordance with the permitted valence of the atom. Suitable substituents are defined herein for each substituted or optionally substituted group.

"Pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

"Pharmaceutically acceptable excipient" refers to a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of formula (I) or a pharmaceutically acceptable salt thereof when administered to a patient and interactions which would result in pharmaceutical compositions that are not pharmaceutically acceptable are avoided. In addition, each excipient must of course be pharmaceutically acceptable e.g. of sufficiently high purity.

"rac" refers to the racemic mixture of the compounds of formula (I).

Throughout the description and the claims which follow, unless the context requires otherwise, the word "comprise", and variations such as "comprises" and "comprising", will be understood to imply the inclusion of a stated integer or step or group of integers but not to the exclusion of any other integer or step or group of integers or steps.

The compounds of the invention may exist in solid or liquid form. In the solid state, the compounds of the invention may exist in crystalline or non-crystalline form, or as a mixture thereof. For compounds of the invention that are in crystalline form, the skilled artisan will appreciate that pharmaceutically acceptable solvates may be formed wherein solvent molecules are incorporated into the crystalline lattice during crystallization. Solvates may involve non-aqueous solvents such as ethanol, iso-propyl alcohol, N,N-dimethylsulfoxide (DMSO), acetic acid, ethanolamine, and ethyl acetate, or they may involve water as the solvent that is incorporated into the crystalline lattice. Solvates wherein water is the solvent that is incorporated into the crystalline lattice are typically referred to as "hydrates". Hydrates include stoichiometric hydrates as well as compositions containing variable amounts of water. The invention includes all such solvates.

It will be further appreciated that certain compounds of the invention that exist in crystalline form, including the various solvates thereof, may exhibit polymorphism (i.e. the capacity to occur in different crystalline structures). These different crystalline forms are typically known as "polymorphs". The invention includes such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. It will be appreciated that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions. Polymorphic forms of compounds of formula (I) may be characterized and differentiated using a number of conventional analytical techniques, including, but not limited to, X-ray powder diffraction (XRPD) patterns, infrared (IR) spectra, Raman spectra, differential scanning calorimetry (DSC), thermogravimetric analysis (TGA) and solid state nuclear magnetic resonance (SSNMR).

The compounds according to formula (I) contain one or more asymmetric centres (also referred to as a chiral centres) and may, therefore, exist as individual enantiomers, diastereoisomers, or other stereoisomeric forms, or as mixtures thereof. Chiral centres, such as chiral carbon atoms, may also be present in a substituent such as an alkyl group. Where the stereochemistry of a chiral centre present in formula (I), or in any chemical structure illustrated herein, is not specified, the structure is intended to encompass any stereoisomer and all mixtures thereof. Thus, compounds according to formula (I) containing one or more chiral centres may be used as racemic modifications including racemic mixtures and racemates, enantiomerically-enriched mixtures, or as enantiomerically-pure individual stereoisomers. Accordingly, the present invention encompasses all isomers of the compounds of formula (I) whether as individual isomers isolated such as to be substantially free of the other isomer (i.e. pure) or as mixtures (i.e. racemates and racemic mixtures). An individual isomer isolated such as to be substantially free of the other isomer (i.e. pure) may be isolated such that less than 10%, particularly less than about 1%, for example less than about 0.1% of the other isomer is present.

Racemic compounds with a single stereocentre are denoted with either no stereochemistry (single bond) or have the annotation (+/−) or rac. Racemic compounds with two or more stereocentres where relative stereochemistry is known are denoted cis or trans as drawn in the structure. Resolved single enantiomers with unknown absolute stereochemistry but known relative stereochemistry are referred to with (R* or S*) with the appropriate relative stereochemistry depicted.

Where the absolute stereochemistry is known and the compound is a single enantiomer, the bold or hashed wedges symbols ( ▬ / ɪɪɪɪɪɪ ) are used as appropriate.

Individual stereoisomers of a compound according to formula (I) which contain one or more asymmetric centres may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. It will be appreciated that where the desired stereoisomer is converted into another chemical entity by one of the separation procedures described above, a further step is required to liberate the desired form. Alternatively, specific stereoisomers may be synthesised by asymmetric synthesis using optically active reagents, substrates, catalysts or solvents, or by converting one enantiomer to the other by asymmetric transformation.

It will be appreciated that, for compounds of formula (I) tautomers may be observed. Any comment relating to the biological activity of a tautomer should be taken to include both tautomers.

It is to be understood that the references herein to compounds of formula (I) and salts thereof covers the compounds of formula (I) as free bases, or as salts thereof, for example as pharmaceutically acceptable salts thereof. Thus, in one embodiment, the invention is directed to compounds of formula (I) as the free base. In another embodiment, the invention is directed to compounds of formula (I) and salts thereof. In a further embodiment, the invention is directed to compounds of formula (I) and pharmaceutically acceptable salts thereof.

Because of their potential use in medicine, salts of the compounds of formula (I) are desirably pharmaceutically acceptable. Suitable pharmaceutically acceptable salts can include acid addition salts or base addition salts. For a review of suitable pharmaceutically acceptable salts see Berge et al., *J. Pharm. Sci.*, 66:1-19, (1977). Typically, a pharmaceutically acceptable salt may be readily prepared by using a desired acid or base as appropriate. The resultant salt may precipitate from solution and be collected by filtration or may be recovered by evaporation of the solvent.

A pharmaceutically acceptable acid addition salt can be formed by reaction of a compound of formula (I) with a suitable inorganic or organic acid (such as hydrobromic, hydrochloric, sulphuric, nitric, phosphoric, succinic, maleic, acetic, propionic, fumaric, citric, tartaric, lactic, benzoic, salicylic, aspartic, p-toluenesulphonic, benzenesulphonic, methanesulphonic, ethanesulphonic, naphthalenesulphonic such as 2-naphthalenesulphonic, or hexanoic acid), optionally in a suitable solvent such as an organic solvent, to give the salt which is usually isolated for example by crystallisation and filtration or by evaporation followed by trituration. A pharmaceutically acceptable acid addition salt of a compound of formula (I) can comprise or be for example a hydrobromide, hydrochloride, sulfate, nitrate, phosphate, succinate, maleate, acetate, propionate, fumarate, citrate, tartrate, lactate, benzoate, salicylate, glutamate, aspartate, p-toluenesulphonate, benzenesulphonate, methanesulphonate, ethanesulphonate, naphthalenesulphonate (e.g. 2-naphthalenesulphonate) or hexanoate salt.

Other non-pharmaceutically acceptable salts, e.g. formates or trifluoroacetates, may be used, for example in the isolation of the compounds of formula (I), and are included within the scope of this invention.

The invention includes within its scope all possible stoichiometric and non-stoichiometric forms of the salts of the compounds of formula (I).

It will be appreciated from the foregoing that included within the scope of the invention are solvates, isomers and polymorphic forms of the compounds of formula (I) and salts thereof.

The present invention also includes isotopically-labeled compounds or a pharmaceutically acceptable salt thereof, which are identical to those recited in Formula (I) above, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulfur, fluorine, chlorine, and iodine, such as $^2$H, $^3$H, $^{11}$C, $^{13}$C, $^{14}$C, $^{15}$N, $^{17}$O, $^{18}$O, $^{31}$P, $^{32}$P, $^{35}$S, $^{18}$F, $^{36}$Cl, $^{123}$I, and $^{125}$I.

STATEMENT OF THE INVENTION

In a first aspect there are provided compounds of formula (I):

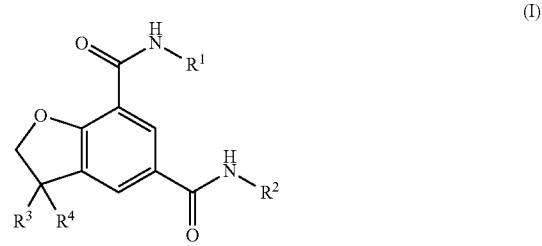

or a salt thereof
wherein:
$R^1$ is —$C_{1-3}$alkyl or cyclopropyl;
$R^2$ is —$C_{0-3}$alkyl-cycloalkyl, wherein the cycloalkyl group is optionally substituted with one, two or three $R^5$ groups which may be the same or different;
$R^2$ is —$C_{0-4}$alkyl-heterocyclyl or —$(CH_2)_p$O-heterocyclyl wherein each heterocyclyl is optionally substituted by one or two $R^9$ groups which may be the same or different; or
$R^2$ is H, —$CH_3$, $C_{2-6}$alkyl optionally substituted by up to five fluoro, —$C_{2-6}$alkylOR$^{13}$, —$C_{2-6}$alkylNR$^{11}$R$^{12}$, —$(CH_2)_mSO_2C_{1-3}$alkyl, —$(CH_2)_mSO_2NR^{11}R^{12}$, —$(CH_2)_mC(O)NR^{11}R^{12}$, —$(CH_2)_mCN$, —$(CH_2)_mCO_2R^{13}$, —$(CH_2)_mNHCO_2C_{1-4}$alkyl-$(CH_2)_mNHC(O)C_{1-4}$alkyl or —$(CH_2)_n$heteroaryl, wherein heteroaryl is optionally substituted by one or two $R^{14}$ groups which may be the same or different;
$R^3$ is phenyl optionally substituted with one, two or three $R^7$ groups which may be the same or different;
$R^4$ is —$CH_2OR^6$ or —$C_{1-3}$alkyl optionally substituted by up to three fluoro;
each $R^5$ is independently halo, —$C_{0-6}$alkyl-$R^8$, —O—$C_{2-6}$ alkyl-$R^8$, —CN or —$SO_2C_{1-3}$alkyl;
$R^6$ is —H or $C_{1-3}$alkyl;
each $R^7$ is independently -halo, —$C_{1-4}$alkyl, —$C_{0-3}$alkyl-OR$^{10}$, —$C_{0-3}$alkyl-NR$^{15}$R$^{16}$, —$C_{0-3}$alkyl-CONR$^{15}$R$^{16}$, —CN or —$SO_2R^{17}$;
$R^8$ is —H, —OR$^{10a}$, —NR$^{18}$R$^{19}$ or heteroaryl;
each $R^9$ is independently halo, $C_{1-4}$alkyl, cyclopropyl, cyclobutyl, —$CH_2CF_3$, —$CH_2CHF_2$, —$CH_2CH_2F$, —$OCH_2CH_2OR^{13}$, —$C_{0-3}$alkylOR$^{13}$, —$C_{0-3}$alkylNR$^{11}$R$^{12}$, —NHCH$_2$CH$_2$OR$^{13}$, —NHCO$_2$R$^{13}$, oxo, —C(O)R$^{13}$, —C(O)OR$^{13}$ or —C(O)NR$^{11}$R$^{12}$;

$R^{10a}$ is —H, —$C_{1-3}$alkyl, —$C_{2-3}$alkylN$R^{11}R^{12}$ or —$C_{2-3}$alkylOH;

$R^{10}$ is —H, —$C_{1-3}$alkyl, —$C_{2-3}$alkylN$R^{15}R^{16}$ or —$C_{2-3}$alkylOH;

$R^{11}$ and $R^{12}$ are each independently selected from —H and —$C_{1-3}$alkyl; or $R^{11}$ and $R^{12}$ may join together with the nitrogen to which they are attached, to form a 4 to 7-membered heterocyclyl group optionally substituted by one or two substituents independently selected from —$C_{1-3}$alkyl, —OH and F;

$R^{13}$ is —H or —$C_{1-4}$alkyl;

each $R^{14}$ is independently halo, $C_{1-4}$alkyl, cyclopropyl, cyclobutyl or —$OR^{13}$;

$R^{15}$ and $R^{16}$ are each independently selected from —H and —$C_{1-3}$alkyl; or $R^{15}$ and $R^{16}$ may join together with the nitrogen to which they are attached, to form a 4 to 7-membered heterocyclyl group optionally substituted by one or two substituents independently selected from —$C_{1-3}$alkyl, —OH and F;

$R^{17}$ is —$C_{1-3}$alkyl or —$NR^{15}R^{16}$;

$R^{18}$ and $R^{19}$ are each independently selected from —H, —C(O)OC(CH$_3$)$_3$, —$C_{1-6}$alkyl, cycloalkyl, heterocyclyl, —$C_{2-3}$alkylN$R^{13}$CO$C_{1-3}$alkyl, —$C_{2-3}$alkylN$R^{15}R^{16}$ and —$C_{2-3}$alkyl-O—$C_{1-3}$alkyl wherein the —$C_{1-6}$alkyl and cycloalkyl may be optionally substituted by one, two or three fluoro; or $R^{18}$ and $R^{19}$ may join together with the nitrogen to which they are attached, to form a 4 to 7-membered heterocyclyl group optionally substituted by one or two substituents independently selected from —$C_{1-3}$alkyl, —OH and F;

m is an integer selected from 2, 3 and 4;

p is an integer selected from 2, 3 and 4; and n is an integer selected from 0, 1, 2, 3 and 4.

In one embodiment $R^1$ is methyl, ethyl, propyl, iso-propyl or cyclopropyl. In another embodiment $R^1$ is methyl.

In one embodiment $R^2$ is —$C_{0-3}$alkyl-cycloalkyl, wherein the cycloalkyl group is optionally substituted with one, two or three $R^5$ groups which may be the same or different. In one embodiment $R^2$ is a —$C_{0-3}$alkyl-$C_{3-7}$cycloalkyl group, wherein the $C_{3-7}$cycloalkyl group is selected from the group consisting of cyclopropyl, cyclobutyl, cyclohexyl or bicyclo[3.1.0]hexanyl said groups being optionally substituted with one, two or three $R^5$ groups which may be the same or different. In another embodiment $R^2$ is cyclopropyl, cyclobutyl, cyclohexyl or bicyclo[3.1.0]hexanyl optionally substituted with one, two or three $R^5$ groups which may be the same or different. In another embodiment $R^2$ is cyclopropyl, cyclobutyl, cyclohexyl or bicyclo[3.1.0]hexanyl optionally substituted with one $R^5$ group selected from methyl, fluoro and —OH. In a particular embodiment $R^2$ is a cyclopropyl optionally substituted by one methyl group. In another particular embodiment $R^2$ is a cyclohexyl group optionally substituted with a $C_{0-6}$alkyl-$R^8$ group such as a —CH$_2$OMe group. In another particular embodiment $R^2$ is a cyclohexyl group optionally substituted with a OH group. In another particular embodiment $R^2$ is a bicyclo[3.1.0]hexanyl optionally substituted by one OH group. In another particular embodiment $R^2$ is a bicyclo[3.1.0]hexanyl optionally substituted by one or two fluoro groups In one embodiment $R^5$ is —$C_{0-6}$alkyl-$R^8$. In another embodiment $R^5$ is methyl or —OH.

In one embodiment $R^2$ is —$C_{0-4}$alkyl-heterocyclyl or —(CH$_2$)$_p$O-heterocyclyl wherein each heterocyclyl is optionally substituted by one or two $R^9$ groups which may be the same or different. In another embodiment $R^2$ is —$C_{0-4}$alkyl-heterocyclyl wherein the heterocyclyl is optionally substituted by one or two $R^9$ groups which may be the same or different. In another embodiment $R^2$ is —$C_{0-4}$alkyl-heterocyclyl which is -heterocyclyl, —CH$_2$CH$_2$-heterocyclyl or —CH$_2$CH$_2$CH$_2$-heterocyclyl. In another embodiment $R^2$ is —$C_{0-4}$alkyl-heterocyclyl wherein the heterocyclyl is selected from oxetanyl, tetrahydrofuranyl, tetrahydro-2H-pyranyl, morpholinyl, piperidinyl, piperazinyl, (1r,5s)-3-oxabicyclo[3.1.0]hexanyl and (1r,5s)-3-azabicyclo[3.1.0]hexanyl optionally substituted by one or two $R^9$ groups which may be the same or different. In another embodiment $R^2$ is —$C_{0-4}$alkyl-heterocyclyl wherein the heterocyclyl is selected from oxetanyl, tetrahydrofuranyl, tetrahydro-2H-pyranyl, morpholinyl, piperidinyl, piperazinyl, (1r,5s)-3-oxabicyclo[3.1.0]hexanyl and (1r,5s)-3-azabicyclo[3.1.0]hexanyl optionally substituted by one or two $R^9$ groups selected from methyl, —C(O)CH$_3$, —NH$_2$ and fluoro. In a further embodiment $R^2$ is —$C_{0-4}$alkyl-heterocyclyl wherein heterocyclyl, optionally substituted by one or two $R^9$ groups, is:

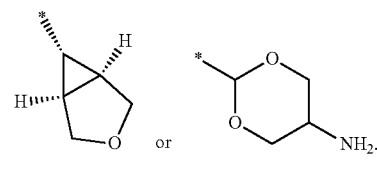

*denotes point of attachment

In one embodiment p is 2 or 3.

In one embodiment $R^2$ is —H, —CH$_3$, $C_{2-6}$alkyl optionally substituted by up to five fluoro, —$C_{2-6}$alkylO$R^{13}$, —$C_{2-6}$alkylN$R^{11}R^{12}$, —(CH$_2$)$_m$SO$_2$$C_{1-3}$alkyl, —(CH$_2$)$_m$SO$_2$N$R^{11}R^{12}$, —(CH$_2$)$_m$C(O)N$R^{11}R^{12}$, —(CH$_2$)$_m$CN, —(CH$_2$)$_m$CO$_2$$R^{13}$, —(CH$_2$)$_m$NHCO$_2$C(CH$_3$)$_3$ or —(CH$_2$)$_n$heteroaryl wherein heteroaryl is optionally substituted by one or two $R^{14}$ groups which may be the same or different. In another embodiment $R^2$ is —H, —CH$_3$, $C_{2-6}$alkyl, —$C_{2-6}$alkylO$R^{13}$, —$C_{2-6}$alkylN$R^{11}R^{12}$ or —(CH$_2$)$_n$heteroaryl. In a further embodiment $R^2$ is —H, methyl, ethyl, propyl, —CH$_2$CH$_2$OH, —CH$_2$CH$_2$CH$_2$OH, —CH$_2$CH(CH$_3$)OH, —CH$_2$CH$_2$OCH$_3$, —CH$_2$CH$_2$CH$_2$OCH$_3$, —CH$_2$CH$_2$N(CH$_3$)$_2$, —CH$_2$CH$_2$CH$_2$N(CH$_3$)$_2$, —CH$_2$CHF$_2$ or —CH$_2$CH$_2$pyridinyl. In another embodiment $R^2$ is —(CH$_2$)$_m$ NHC(O)$C_{1-4}$alkyl such as —(CH$_2$)$_3$NHC(O)Me. In another embodiment $R^2$ is —$C_{2-6}$alkylN$R^{11}R^{12}$ such as —(CH$_2$)$_3$NH$_2$.

In another embodiment $R^2$ is —(CH$_2$)$_n$heteroaryl wherein heteroaryl is selected from the group consisting of furanyl, thienyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl and triazinyl said groups being optionally substituted by one or two $R^{14}$ groups which may be the same or different. In another embodiment there is provided compounds of formula (I) in which $R^2$ is —(CH$_2$)$_n$heteroaryl wherein the heteroaryl is pyrazolyl optionally substituted by $C_{1-4}$alkyl.

In one embodiment n is 0, 2 or 3. In one embodiment n is 0. In another embodiment n is 2.

In one embodiment $R^3$ is phenyl optionally substituted by —OCH$_3$ or —OCH$_2$CH$_2$OH. In another embodiment $R^3$ is phenyl.

In one embodiment $R^4$ is methyl, ethyl or —CH$_2$OH.

In one embodiment the compound of formula (I) is a compound of formula (IA)

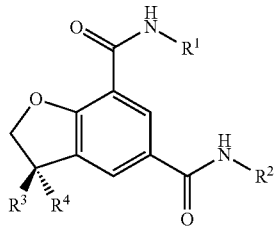

(IA)

or a salt thereof, wherein $R^1$, $R^2$, $R^3$ and $R^4$ are defined according to formula (I).

In another embodiment the compound of formula (I) is a compound of formula (IB)

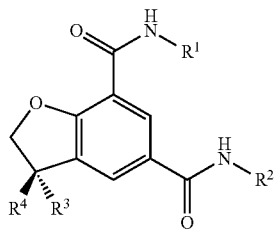

(IB)

or a salt thereof, wherein $R^1$, $R^2$, $R^3$ and $R^4$ are defined according to formula (I).

It is to be understood that the present invention covers all combinations of substituent groups described hereinabove.

Compounds of the invention include the compounds of Examples 1 to 32 and salts thereof.

Compounds of the invention include the compounds of Examples 33 to 65 and salts thereof.

Compounds of the invention include the compounds of Examples 1 to 65 and salts thereof.

In one embodiment the compound of formula (I) is selected from:

(+/−)-$N^5$-((1R,5S,6r)-3-oxabicyclo[3.1.0]hexan-6-yl)-$N^7$,3-dimethyl-3-phenyl-2,3-dihydrobenzofuran-5,7-dicarboxamide;

(S*)-$N^5$-((1R,5S,6r)-3-oxabicyclo[3.1.0]hexan-6-yl)-$N^7$,3-dimethyl-3-phenyl-2,3-dihydrobenzofuran-5,7-dicarboxamide;

(R*)-$N^5$-((1R,5S,6r)-3-oxabicyclo[3.1.0]hexan-6-yl)-$N^7$,3-dimethyl-3-phenyl-2,3-dihydrobenzofuran-5,7-dicarboxamide;

(S*)-$N^5$,$N^7$,3-Trimethyl-3-phenyl-2,3-dihydrobenzofuran-5,7-dicarboxamide;

(S*)-$N^5$-Ethyl-$N^7$,3-dimethyl-3-phenyl-2,3-dihydrobenzofuran-5,7-dicarboxamide;

(S*)-$N^5$-Cyclopropyl-$N^7$,3-dimethyl-3-phenyl-2,3-dihydrobenzofuran-5,7-dicarboxamide;

(S*)-$N^5$-((1r,4s)-4-Hydroxycyclohexyl)-$N^7$,3-dimethyl-3-phenyl-2,3-dihydrobenzofuran-5,7-dicarboxamide;

(S*)-$N^7$,3-Dimethyl-$N^5$-((1S,2S)-2-methylcyclopropyl)-3-phenyl-2,3-dihydrobenzofuran-5,7-dicarboxamide;

(S*)-$N^5$-((1R,3R,5S,6r)-3-Hydroxybicyclo[3.1.0]hexan-6-yl)-$N^7$,3-dimethyl-3-phenyl-2,3-dihydrobenzofuran-5,7-dicarboxamide;

(S*)-$N^5$-((1R,3S,5S,6r)-3-hydroxybicyclo[3.1.0]hexan-6-yl)-$N^7$,3-dimethyl-3-phenyl-2,3-dihydrobenzofuran-5,7-dicarboxamide;

(S*)-$N^5$-(3-((2r,5S)-5-amino-1,3-dioxan-2-yl)propyl)-$N^7$,3-dimethyl-3-phenyl-2,3-dihydrobenzofuran-5,7-dicarboxamide;

(S*)-$N^5$-(2-((2r,5S)-5-amino-1,3-dioxan-2-yl)ethyl)-$N^7$,3-dimethyl-3-phenyl-2,3-dihydrobenzofuran-5,7-dicarboxamide;

(+/−)-$N^5$-((1R,5S,6r)-3-Oxabicyclo[3.1.0]hexan-6-yl)-3-(hydroxymethyl)-$N^7$-methyl-3-phenyl-2,3-dihydrobenzofuran-5,7-dicarboxamide;

(S*)-$N^5$-((1R,5S,6r)-3-oxabicyclo[3.1.0]hexan-6-yl)-3-(hydroxymethyl)-$N^7$-methyl-3-phenyl-2,3-dihydrobenzofuran-5,7-dicarboxamide;

(R*)-$N^5$-((1R,5S,6r)-3-oxabicyclo[3.1.0]hexan-6-yl)-3-(hydroxymethyl)-$N^7$-methyl-3-phenyl-2,3-dihydrobenzofuran-5,7-dicarboxamide;

(S*)-$N^5$-((1R,3R,5S,6r)-3-hydroxybicyclo[3.1.0]hexan-6-yl)-3-(hydroxymethyl)-$N^7$-methyl-3-phenyl-2,3-dihydrobenzofuran-5,7-dicarboxamide;

(S*)-$N^5$-((1R,3S,5S,6r)-3-hydroxybicyclo[3.1.0]hexan-6-yl)-3-(hydroxymethyl)-$N^7$-methyl-3-phenyl-2,3-dihydrobenzofuran-5,7-dicarboxamide;

(+/−)-3-(Hydroxymethyl)-$N^7$-methyl-$N^5$-((1S,2S)-2-methylcyclopropyl)-3-phenyl-2,3-dihydrobenzofuran-5,7-dicarboxamide;

(S*)-3-(Hydroxymethyl)-$N^5$,$N^7$-dimethyl-3-phenyl-2,3-dihydrobenzofuran-5,7-dicarboxamide;

(S*)-$N^5$-Ethyl-3-(hydroxymethyl)-$N^7$-methyl-3-phenyl-2,3-dihydrobenzofuran-5,7-dicarboxamide;

(S*)-$N^5$-Cyclopropyl-3-(hydroxymethyl)-$N^7$-methyl-3-phenyl-2,3-dihydrobenzofuran-5,7-dicarboxamide;

(S*)-$N^5$-((1r,4s)-4-Hydroxycyclohexyl)-3-(hydroxymethyl)-$N^7$-methyl-3-phenyl-2,3-dihydrobenzofuran-5,7-dicarboxamide;

(S*)-3-(Hydroxymethyl)-$N^7$-methyl-$N^5$-((1S,2S)-2-methylcyclopropyl)-3-phenyl-2,3-dihydrobenzofuran-5,7-dicarboxamide;

(S*)-$N^5$-((1R,5S,6r)-3-Oxabicyclo[3.1.0]hexan-6-yl)-3-ethyl-$N^7$-methyl-3-phenyl-2,3-dihydrobenzofuran-5,7-dicarboxamide;

(S*)-3-Ethyl-$N^5$,$N^7$-dimethyl-3-phenyl-2,3-dihydrobenzofuran-5,7-dicarboxamide;

(S*)-$N^5$,3-diethyl-$N^7$-methyl-3-phenyl-2,3-dihydrobenzofuran-5,7-dicarboxamide;

(S*)-$N^5$-Cyclopropyl-3-ethyl-$N^7$-methyl-3-phenyl-2,3-dihydrobenzofuran-5,7-dicarboxamide;

(S*)-3-Ethyl-$N^7$-methyl-$N^5$-((1S,2S)-2-methylcyclopropyl)-3-phenyl-2,3-dihydrobenzofuran-5,7-dicarboxamide;

(S*)-3-Ethyl-$N^5$-((1r,4s)-4-hydroxycyclohexyl)-$N^7$-methyl-3-phenyl-2,3-dihydrobenzofuran-5,7-dicarboxamide;

(S*)-3-Ethyl-$N^5$-((1R,3R,5S,6r)-3-hydroxybicyclo[3.1.0]hexan-6-yl)-$N^7$-methyl-3-phenyl-2,3-dihydrobenzofuran-5,7-dicarboxamide;

(S*)-$N^5$-(2-((2r,5S)-5-amino-1,3-dioxan-2-yl)ethyl)-3-ethyl-$N^7$-methyl-3-phenyl-2,3-dihydrobenzofuran-5,7-dicarboxamide; and (S*)-$N^5$-(3-((2r,5S)-5-Amino-1,3-dioxan-2-yl)propyl)-3-ethyl-$N^7$-methyl-3-phenyl-2,3-dihydrobenzofuran-5,7-dicarboxamide or a salt thereof.

In another embodiment the compound of formula (I) is selected from:

(+/−) 3-ethyl-$N^5$-(3-hydroxypropyl)-$N^7$-methyl-3-phenyl-2,3-dihydrobenzofuran-5,7-dicarboxamide;

N$^5$-((1R,2R)-2-(methoxymethyl)cyclopropyl)-N$^7$,3-dimethyl-3-phenyl-2,3-dihydrobenzofuran-5,7-dicarboxamide;

N$^5$-(2-(1H-pyrazol-4-yl)ethyl)-N$^7$,3-dimethyl-3-phenyl-2,3-dihydrobenzofuran-5,7-dicarboxamide;

3-(hydroxymethyl)-N$^5$-(3-hydroxypropyl)-N$^7$-methyl-3-phenyl-2,3-dihydrobenzofuran-5,7-dicarboxamide;

N$^7$,3-dimethyl-3-phenyl-N$^5$-(1H-pyrazol-4-yl)-2,3-dihydrobenzofuran-5,7-dicarboxamide;

N$^5$-((1R,5S,6r)-3,3-difluorobicyclo[3.1.0]hexan-6-yl)-3-(hydroxymethyl)-N$^7$-methyl-3-phenyl-2,3-dihydrobenzofuran-5,7-dicarboxamide;

N$^5$-((1R,5S,60-3,3-difluorobicyclo[3.1.0]hexan-6-yl)-N$^7$,3-dimethyl-3-phenyl-2,3-dihydrobenzofuran-5,7-dicarboxamide;

N$^5$-(2-(1H-pyrazol-4-yl)ethyl)-3-ethyl-N$^7$-methyl-3-phenyl-2,3-dihydrobenzofuran-5,7-dicarboxamide;

N$^5$-(3-acetamidopropyl)-3-ethyl-N$^7$-methyl-3-phenyl-2,3-dihydrobenzofuran-5,7-dicarboxamide;

3-ethyl-N$^5$-((1R,2R)-2-(methoxymethyl)cyclopropyl)-N$^7$-methyl-3-phenyl-2,3-dihydrobenzofuran-5,7-dicarboxamide;

N$^5$-(3-acetamidopropyl)-3-(hydroxymethyl)-N$^7$-methyl-3-phenyl-2,3-dihydrobenzofuran-5,7-dicarboxamide;

N$^5$-(3-hydroxpropyl)-N$^7$,3-dimethyl-3-phenyl-2,3-dihydrobenzofuran-5,7-dicarboxamide;

3-ethyl-N$^5$-((1S,2S)-2-(methoxymethyl)cyclopropyl)-N$^7$-methyl-3-phenyl-2,3-dihydrobenzofuran-5,7-dicarboxamide;

3-(hydroxymethyl)-N$^5$-((1R,2R)-2-(methoxymethyl)cyclopropyl)-N$^7$-methyl-3-phenyl-2,3-dihydrobenzofuran-5,7-dicarboxamide;

3-ethyl-N$^7$-methyl-3-phenyl-N$^5$-(1H-pyrazol-4-yl)-2,3-dihydrobenzofuran-5,7-dicarboxamide;

3-(hydroxymethyl)-N$^5$-((1S,2S)-2-(methoxymethyl)cyclopropyl)-N$^7$-methyl-3-phenyl-2,3-dihydrobenzofuran-5,7-dicarboxamide;

N$^5$-((1R,5S,6r)-3,3-difluorobicyclo[3.1.0]hexan-6-yl)-3-ethyl-N$^7$-methyl-3-phenyl-2,3-dihydrobenzofuran-5,7-dicarboxamide;

N$^5$-((1S,2S)-2-(methoxymethyl)cyclopropyl)-N$^7$,3-dimethyl-3-phenyl-2,3-dihydrobenzofuran-5,7-dicarboxamide;

N$^5$-(2-(1H-pyrazol-4-yl)ethyl)-3-(hydroxymethyl)-N$^7$-methyl-3-phenyl-2,3-dihydrobenzofuran-5,7-dicarboxamide;

3-(hydroxymethyl)-N$^7$-methyl-3-phenyl-N$^5$-(1H-pyrazol-4-yl)-2,3-dihydrobenzofuran-5,7-dicarboxamide;

N$^5$-(3-acetamidopropyl)-N$^7$,3-dimethyl-3-phenyl-2,3-dihydrobenzofuran-5,7-dicarboxamide;

(+/−) N$^5$-(3-aminopropyl)-3-(hydroxymethyl)-N$^7$-methyl-3-phenyl-2,3-dihydrobenzofuran-5,7-dicarboxamide;

(+/−) N$^7$,3-dimethyl-3-phenyl-N$^5$-(2-(piperidin-4-yl)ethyl)-2,3-dihydrobenzofuran-5,7-dicarboxamide;

(+/−) 3-(hydroxymethyl)-N$^7$-methyl-N$^5$-(2-((S)-morpholin-2-yl)ethyl)-3-phenyl-2,3-dihydrobenzofuran-5,7-dicarboxamide;

(−/+) N$^5$-(3-aminopropyl)-3-ethyl-N$^7$-methyl-3-phenyl-2,3-dihydrobenzofuran-5,7-dicarboxamide;

(+/−) 3-ethyl-N$^7$-methyl-N$^5$-(2-((S)-morpholin-2-yl)ethyl)-3-phenyl-2,3-dihydrobenzofuran-5,7-dicarboxamide;

(+/−) 3-(hydroxymethyl)-N$^7$-methyl-3-phenyl-N$^5$-(2-(piperidin-4-yl)ethyl)-2,3-dihydrobenzofuran-5,7-dicarboxamide;

(+/−) 3-ethyl-N$^7$-methyl-N$^5$-(2-((R)-morpholin-2-yl)ethyl)-3-phenyl-2,3-dihydrobenzofuran-5,7-dicarboxamide;

(+/−) 3-ethyl-N$^7$-methyl-3-phenyl-N$^5$-(2-(piperidin-4-yl)ethyl)-2,3-dihydrobenzofuran-5,7-dicarboxamide;

(+/−) 3-(hydroxymethyl)-N$^7$-methyl-N$^5$-(2-(R)-morpholin-2-yl)ethyl)-3-phenyl-2,3-dihydrobenzofuran-5,7-dicarboxamide;

(+/−) 3-dimethyl-N$^7$-(2-((R)-morpholin-2-yl)ethyl)-3-phenyl-2,3-dihydrobenzofuran-5,7-dicarboxamide;

(+/−) 3-dimethyl-N$_5$-(2-((S)-morpholin-2-yl)ethyl)-3-phenyl-2,3-dihydrobenzofuran-5,7-dicarboxamide; and (+/−) N$^5$-(3-aminopropyl)-N$^7$,3-dimethyl-3-phenyl-2,3-dihydrobenzofuran-5,7-dicarboxamide or a salt thereof.

In another embodiment the compound of formula (I) is selected from:

(+/−)-N$^5$-((1R,5S,6r)-3-oxabicyclo[3.1.0]hexan-6-yl)-N$^7$,3-dimethyl-3-phenyl-2,3-dihydrobenzofuran-5,7-dicarboxamide;

(S*)—N$^5$-((1R,5S,6r)-3-oxabicyclo[3.1.0]hexan-6-yl)-N$^7$,3-dimethyl-3-phenyl-2,3-dihydrobenzofuran-5,7-dicarboxamide;

(S*)—N$^5$-((1R,3R,5S,6r)-3-Hydroxybicyclo[3.1.0]hexan-6-yl)-N$^7$,3-dimethyl-3-phenyl-2,3-dihydrobenzofuran-5,7-dicarboxamide; and (S*)-3-(Hydroxymethyl)-N$^7$-methyl-N$^5$-((1S,2S)-2-methylcyclopropyl)-3-phenyl-2,3-dihydrobenzofuran-5,7-dicarboxamide or a salt thereof.

In a second aspect of the present invention, there is provided a pharmaceutical composition comprising a compound of formula (I) or a pharmaceutically acceptable salt thereof and one or more pharmaceutically acceptable excipients.

In a third aspect of the present invention, there is provided a compound of formula (I), or a pharmaceutically acceptable salt thereof for use in therapy, in particular in the treatment of diseases or conditions for which a bromodomain inhibitor is indicated.

In a fourth aspect of the present invention, there is provided a method of treating diseases or conditions for which a bromodomain inhibitor is indicated in a subject in need thereof which comprises administering a therapeutically effective amount of a compound of formula (I) or a pharmaceutically acceptable salt thereof.

In a fifth aspect of the present invention, there is provided the use of a compound of formula (I), or a pharmaceutically acceptable salt thereof in the manufacture of a medicament for the treatment of diseases or conditions for which a bromodomain inhibitor is indicated.

Statement of Use

The compounds of formula (I) and salts thereof are bromodomain inhibitors, and thus are believed to have potential utility in the treatment of diseases or conditions for which a bromodomain inhibitor is indicated.

Bromodomain inhibitors are believed to be useful in the treatment of a variety of diseases or conditions related to systemic or tissue inflammation, inflammatory responses to infection or hypoxia, cellular activation and proliferation, lipid metabolism, fibrosis and in the prevention and treatment of viral infections.

Bromodomain inhibitors may be useful in the treatment of a wide variety of acute or chronic autoimmune and/or inflammatory conditions such as rheumatoid arthritis, psoriatic arthritis, ankylosing spondylitis, osteoarthritis, acute gout, psoriasis, systemic lupus erythematosus, multiple sclerosis, inflammatory bowel disease (Crohn's disease and ulcerative colitis), asthma, chronic obstructive airways disease, pneumonitis, myocarditis, pericarditis, myositis, eczema, dermatitis (including atopic dermatitis), alopecia, vitiligo, bullous skin diseases, nephritis, vasculitis, hypercholesterolemia, atherosclerosis, Alzheimer's disease, Sjögren's syndrome, sialoadenitis, central retinal vein occlusion, branched retinal vein occlusion, Irvine-Gass syndrome (post cataract and post-surgical), retinitis pigmentosa, pars planitis, birdshot retinochoroidopathy, epiretinal membrane, cystic macular edema, parafoveal telengiectasis, tractional maculopathies, vitreomacular traction syndromes, retinal detachment, neuroretinitis, idiopathic macular edema, retinitis, dry eye (keratoconjunctivitis Sicca), vernal keratoconjunctivitis, atopic keratoconjunctivitis, uveitis (such as anterior uveitis, pan uveitis, posterior uveitis, uveitis-associated macular edema), scleritis, diabetic retinopathy, diabetic macula edema, age-related macular dystrophy, hepatitis, pancreatitis, primary biliary cirrhosis, sclerosing cholangitis, Addison's disease, hypophysitis, thyroiditis, Type I diabetes, Type II diabetes, giant cell arteritis, nephritis including lupus nephritis, vasculitis with organ involvement such as glomerulonephritis, vasculitis including giant cell arteritis, Wegener's granulomatosis, Polyarteritis nodosa, Behcet's disease, Kawasaki disease, Takayasu's Arteritis, pyoderma gangrenosum, vasculitis with organ involvement, acute rejection of transplanted organs and systemic sclerosis.

In one embodiment the acute or chronic autoimmune and/or inflammatory condition is a disorder of lipid metabolism mediated via the regulation of APO-A1 such as hypercholesterolemia, atherosclerosis or Alzheimer's disease.

In another embodiment the acute or chronic autoimmune and/or inflammatory condition is a respiratory disorder such as asthma or chronic obstructive airways disease.

In another embodiment the acute or chronic autoimmune and/or inflammatory condition is a systemic inflammatory disorder such as rheumatoid arthritis, osteoarthritis, acute gout, psoriasis, systemic lupus erythematosus, multiple sclerosis or inflammatory bowel disease (Crohn's disease or Ulcerative colitis).

In another embodiment, the acute or chronic autoimmune and/or inflammatory condition is multiple sclerosis.

In another embodiment, the acute or chronic autoimmune and/or inflammatory condition is Type I diabetes.

In another embodiment, the acute or chronic autoimmune and/or inflammatory condition is rheumatoid arthritis.

Bromodomain inhibitors may be useful in the treatment of depression.

Bromodomain inhibitors may be useful in the treatment of diseases or conditions which involve inflammatory responses to infections with bacteria, viruses, fungi, parasites or their toxins, such as sepsis, acute sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria and SIRS associated with viral infections such as influenza, herpes zoster, herpes simplex and coronavirus. In one embodiment the disease or condition which involves an inflammatory response to an infection with bacteria, a virus, fungi, a parasite or their toxins is acute sepsis.

Bromodomain inhibitors may be useful in the treatment of conditions associated with ischaemia-reperfusion injury such as myocardial infarction, cerebro-vascular ischaemia (stroke), acute coronary syndromes, renal reperfusion injury, organ transplantation, coronary artery bypass grafting, cardio-pulmonary bypass procedures, pulmonary, renal, hepatic, gastro-intestinal or peripheral limb embolism.

Bromodomain inhibitors may be useful in the treatment of cardiovascular diseases such as coronary artery diseases (for example, angina or myocardial infarction), pulmonary arterial hypertension, cerebro-vascular ischaemia (stroke), hypertensive heart disease, rheumatic heart disease, cardiomyopathy, atrial fibrillation, congenital heart disease, endocarditis, aortic aneurysms or peripheral artery disease.

Bromodomain inhibitors may be useful in the treatment of fibrotic conditions such as idiopathic pulmonary fibrosis, pulmonary fibrosis, cystic fibrosis, progressive massive fibrosis, renal fibrosis, liver fibrosis, liver cirrhosis, non-alcoholic steatohepatitis (NASH), non-alcoholic fatty liver disease (NAFLD), post-operative stricture, keloid scar formation, scleroderma (including morphea and systemic sclerosis), cardiac fibrosis, atrial fibrosis, endomyocardial fibrosis, old myocardial infarction, arthrofibrosis, Dupuytren's contracture, mediastinal, myelofibrosis, Peyronie's disease, nephrogenic systemic fibrosis, retroperitoneal fibrosis and adhesive capsulitis.

Bromodomain inhibitors may be useful in the treatment of viral infections such as herpes simplex infections and reactivations, cold sores, herpes zoster infections and reactivations, chickenpox, shingles, human papilloma virus (HPV), human immunodeficiency virus (HIV), cervical neoplasia, adenovirus infections, including acute respiratory disease, poxvirus infections such as cowpox or smallpox, or African swine fever virus. In one embodiment the viral infection is a HPV infection of skin or cervical epithelia. In another embodiment the viral infection is a latent HIV infection.

Bromodomain inhibitors may be useful in the treatment of a wide variety of bone disorders such as osteoporosis, osteopenia, osteoarthritis and ankylosing spondylitis.

Bromodomain inhibitors may be useful in the treatment of cancer, including hematological cancers (such as leukaemia, lymphoma and multiple myeloma), epithelial cancers (including lung, breast or colon carcinomas), midline carcinomas, or mesenchymal, hepatic, renal or neurological tumours.

Bromodomain inhibitors may be useful in the treatment of one or more cancers selected from brain cancer (gliomas), glioblastomas, Bannayan-Zonana syndrome, Cowden disease, Lhermitte-Duclos disease, breast cancer, inflammatory breast cancer, colorectal cancer, Wilm's tumor, Ewing's sarcoma, rhabdomyosarcoma, ependymoma, medulloblastoma, colon cancer, head and neck cancer, kidney cancer, lung cancer, liver cancer, melanoma, squamous cell carcinoma, ovarian cancer, pancreatic cancer, prostate cancer, sarcoma cancer, osteosarcoma, giant cell tumor of bone, thyroid cancer, lymphoblastic T-cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T-cell leukemia, plasmacytoma, immunoblastic large cell leukemia, mantle cell leukemia, multiple myeloma, megakaryoblastic leukemia, acute megakaryocytic leukemia, promyelocytic leukemia, mixed lineage leukaemia, erythroleukemia, malignant lymphoma, Hodgkins lymphoma, non-Hodgkins lymphoma, lymphoblastic T-cell lymphoma, Burkitt's lymphoma, follicular lymphoma, neuroblastoma, bladder cancer, urothelial cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor), NUT-midline carcinoma and testicular cancer.

In one embodiment the cancer is a leukaemia, for example a leukaemia selected from acute monocytic leukemia, acute myelogenous leukemia, chronic myelogenous leukemia, chronic lymphocytic leukemia and mixed lineage leukaemia (MLL). In another embodiment the cancer is NUT-midline carcinoma. In another embodiment the cancer is multiple myeloma. In another embodiment the cancer is a lung cancer such as small cell lung cancer (SCLC). In another embodiment the cancer is a neuroblastoma. In another embodiment the cancer is Burkitt's lymphoma. In another embodiment the cancer is cervical cancer. In another embodiment the cancer is esophageal cancer. In another embodiment the cancer is ovarian cancer. In another embodiment the cancer is breast cancer. In another embodiment the cancer is colorectal cancer. In another embodiment the cancer is prostate cancer. In another embodiment the cancer is castration resistant prostate cancer.

Bromodomain inhibitors may be useful in the treatment of diseases associated with systemic inflammatory response syndrome, such as sepsis, burns, pancreatitis, major trauma, haemorrhage and ischaemia. In this embodiment, the bromodomain inhibitor would be administered at the point of diagnosis to reduce the incidence of: SIRS, the onset of shock, multi-organ dysfunction syndrome, which includes the onset of acute lung injury, ARDS, acute renal, hepatic, cardiac or gastro-intestinal injury and mortality. In another embodiment the bromodomain inhibitor would be administered prior to surgical or other procedures associated with a high risk of sepsis, haemorrhage, extensive tissue damage, SIRS or MODS (multiple organ dysfunction syndrome). In a particular embodiment the disease or condition for which a bromodomain inhibitor is indicated is sepsis, sepsis syndrome, septic shock and endotoxaemia. In another embodiment, the bromodomain inhibitor is indicated for the treatment of acute or chronic pancreatitis. In another embodiment the bromodomain is indicated for the treatment of burns.

The present invention thus provides a compound of formula (I) or a pharmaceutically acceptable salt thereof for use in therapy. The compound of formula (I) or a pharmaceutically salt thereof can be used in the treatment of diseases or conditions for which a bromodomain inhibitor is indicated.

The present invention thus provides a compound of formula (I) or a pharmaceutically acceptable salt thereof for use in the treatment of a disease or condition for which a bromodomain inhibitor is indicated. In one embodiment there is provided a compound of formula (I) or a pharmaceutically acceptable salt thereof for use in the treatment of acute or chronic auto-immune and/or inflammatory conditions. In one embodiment there is provided a compound of formula (I) or a pharmaceutically acceptable salt thereof for use in the treatment of rheumatoid arthritis. In another embodiment there is provided a compound of formula (I) or a pharmaceutically acceptable salt thereof for use in the treatment of diseases or conditions which involve inflammatory responses to infections with bacteria, viruses, fungi, parasites or their toxins. In another embodiment there is provided a compound of formula (I) or a pharmaceutically acceptable salt thereof for use in the treatment of conditions associated with ischaemia-reperfusion injury. In another embodiment there is provided a compound of formula (I) or a pharmaceutically acceptable salt thereof for use in the treatment of cardiovascular diseases. In another embodiment there is provided a compound of formula (I) or a pharmaceutically acceptable salt thereof for use in the treatment of fibrotic conditions. In another embodiment there is provided a compound of formula (I) or a pharmaceutically acceptable salt thereof for use in the treatment of viral infections. In another embodiment there is provided a compound of formula (I) or a pharmaceutically acceptable salt thereof for use in the treatment of bone disorders. In another embodiment there is provided a compound of formula (I) or a pharmaceutically acceptable salt thereof for use in the treatment of cancer. In a further embodiment there is provided a compound of formula (I) or a pharmaceutically acceptable salt thereof for use in the treatment of diseases associated with systemic inflammatory response syndrome.

Also provided is the use of a compound of formula (I) or a pharmaceutically acceptable salt thereof in the manufacture of a medicament for the treatment of diseases or conditions for which a bromodomain inhibitor is indicated. In one embodiment there is provided the use of a compound of formula (I) or a pharmaceutically acceptable salt thereof in the manufacture of a medicament for the treatment of acute or chronic auto-immune and/or inflammatory conditions. In one embodiment there is provided the use of a compound of formula (I) or a pharmaceutically acceptable salt thereof in the manufacture of a medicament for the treatment of rheumatoid arthritis. In another embodiment there is provided the use of a compound of formula (I) or a pharmaceutically acceptable salt thereof in the manufacture of a medicament for the treatment of diseases or conditions which involve inflammatory responses to infections with bacteria, viruses, fungi, parasites or their toxins. In another embodiment there is provided the use of a compound of formula (I) or a pharmaceutically acceptable salt thereof in the manufacture of a medicament for the treatment of conditions associated with ischaemia-reperfusion injury. In another embodiment there is provided the use of a compound of formula (I) or a pharmaceutically acceptable salt thereof in the manufacture of a medicament for the treatment of cardiovascular diseases. In another embodiment there is provided the use of a compound of formula (I) or a pharmaceutically acceptable salt thereof in the manufacture of a medicament for the treatment of fibrotic conditions. In another embodiment there is provided the use of a compound of formula (I) or a pharmaceutically acceptable salt thereof in the manufacture of a medicament for the treatment of viral infections. In another embodiment there is provided the use of a compound of formula (I) or a pharmaceutically acceptable salt thereof in the manufacture of a medicament for the treatment of cancer. In a further embodiment there is provided the use of a compound of formula (I) or a pharmaceutically acceptable salt thereof in the manufacture of a medicament for the treatment of diseases associated with systemic inflammatory response syndrome.

Also provided is a method of treating diseases or conditions for which a bromodomain inhibitor is indicated in a subject in need thereof which comprises administering a therapeutically effective amount of compound of formula (I) or a pharmaceutically acceptable salt thereof. In one embodiment there is provided a method of treating acute or chronic auto-immune and/or inflammatory conditions in a subject in need thereof which comprises administering a therapeutically effective amount of a compound of formula (I) or a pharmaceutically acceptable salt thereof. In one embodiment there is provided a method of treating rheumatoid arthritis in a subject in need thereof which comprises administering a therapeutically effective amount of a compound of formula (I) or a pharmaceutically acceptable salt thereof. In another embodiment there is provided a method of treating diseases or conditions which involve inflammatory responses to infections with bacteria, viruses, fungi, parasites or their toxins in a subject in need thereof which comprises administering a therapeutically effective amount of a compound of formula (I) or a pharmaceutically acceptable salt thereof. In another embodiment there is provided a method of treating conditions associated with ischaemia-reperfusion injury in a subject in need thereof which comprises administering a therapeutically effective amount of a compound of formula (I) or a pharmaceutically acceptable salt thereof. In another embodiment there is provided a method of treating cardiovascular diseases in a subject in need thereof which comprises administering a therapeutically effective amount of a compound of formula (I) or a pharmaceutically acceptable salt thereof. In another embodiment there is provided a method of treating fibrotic conditions in a subject in need thereof which comprises administering a therapeutically effective amount of a compound of formula (I) or a pharmaceutically acceptable salt thereof. In another embodiment there is provided a method of treating viral infections in a subject in need thereof which comprises administering a therapeutically effective amount of a compound of formula (I) or a pharmaceutically acceptable salt thereof. In another embodiment there is provided a method of treating cancer in a subject in need thereof which comprises administering a therapeutically effective amount of a compound of formula (I) or a pharmaceutically acceptable salt thereof. In a further embodiment there is provided a method of treating diseases associated with systemic inflammatory response syndrome in a subject in need thereof which comprises administering a therapeutically effective amount of a compound of formula (I) or a pharmaceutically acceptable salt thereof.

Suitably the subject in need thereof is a mammal, particularly a human.

The invention further provides for a method for inhibiting a bromodomain containing protein which comprises contacting the bromodomain containing protein with a compound of formula (I) or a pharmaceutically acceptable salt thereof.

As used herein the reference to the "treatment" of a particular disease or condition includes the prevention or prophylaxis of such a disease or condition.

Pharmaceutical Compositions/Routes of Administration/Dosages

Compositions

While it is possible that for use in therapy, a compound of formula (I) as well as pharmaceutically acceptable salts thereof may be administered as the raw chemical, it is common to present the active ingredient as a pharmaceutical composition. The compounds of formula (I) and pharmaceutically acceptable salts thereof will normally, but not necessarily, be formulated into pharmaceutical compositions prior to administration to a patient. Accordingly, in another aspect there is provided a pharmaceutical composition comprising a compound of formula (I), or a pharmaceutically acceptable salt thereof, and one or more pharmaceutically acceptable excipients. The compounds of formula (I) and pharmaceutically acceptable salts are as described above. The excipient(s) must be acceptable in the sense of being compatible with the other ingredients of the composition and not deleterious to the recipient thereof. In accordance with another aspect of the invention there is also provided a process for the preparation of a pharmaceutical composition including admixing a compound of formula (I), or a pharmaceutically acceptable salt thereof, with one or more pharmaceutically acceptable excipients. The pharmaceutical composition can be used in the treatment of any of the conditions described herein.

In a further aspect the invention is directed to pharmaceutical compositions for the treatment or prophylaxis of a disease or condition for which a bromodomain inhibitor is indicated comprising a compound of formula (I) or a pharmaceutically acceptable salt thereof.

Since the compounds of formula (I) are intended for use in pharmaceutical compositions it will be readily understood that they are each preferably provided in substantially pure form, for example, at least 85% pure, especially at least 98% pure (% in a weight for weight basis).

Pharmaceutical compositions may be presented in unit dose forms containing a predetermined amount of active ingredient per unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose (for administration more than once a day), as herein above recited, or an appropriate fraction thereof, of an active ingredient.

Pharmaceutical compositions may be adapted for administration by any appropriate route, for example by the oral (including buccal or sublingual), rectal, inhaled, intranasal, topical (including buccal, sublingual or transdermal), ocular (including topical, intraocular, subconjunctival, episcleral, sub-Tenon), vaginal or parenteral (including subcutaneous, intramuscular, intravenous or intradermal) route. Such compositions may be prepared by any method known in the art of pharmacy, for example by bringing into association the active ingredient with the carrier(s) or excipient(s).

The pharmaceutical compositions of the invention may be prepared and packaged in bulk form wherein a safe and effective amount of a compound of formula (I) or a pharmaceutically acceptable salt thereof can be extracted and then given to the patient such as with powders or syrups. Alternatively, the pharmaceutical compositions of the invention may be prepared and packaged in unit dosage form wherein each physically discrete unit contains a compound of formula (I) or a pharmaceutically acceptable salt thereof. When prepared in unit dosage form, the pharmaceutical compositions of the invention typically may contain, for example, from 0.25 mg to 1 g, or from 0.5 mg to 500 mg, or from 1 mg to 100 mg, of a compound of formula (I) or a pharmaceutically acceptable salt thereof.

The pharmaceutical compositions of the invention typically contain one compound of formula (I) or a pharmaceutically acceptable salt thereof.

The compound of formula (I) or a pharmaceutically acceptable salt thereof and the pharmaceutically acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols, solutions, and dry powders; and (6) topical administration such as creams, ointments, lotions, solutions, pastes, sprays, foams, and gels.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting of the compound or compounds of formula (I) or pharmaceutically acceptable salts thereof once administered to the subject from one organ, or portion of the body, to another organ, or portion of the body. Certain pharmaceutically acceptable excipients may be chosen for their ability to enhance subject compliance.

Suitable pharmaceutically-acceptable excipients include the following types of excipients: carriers, diluents, fillers, binders, disintegrants, lubricants, glidants, granulating agents, coating agents, wetting agents, solvents, co-solvents, suspending agents, emulsifiers, sweetners, flavouring agents, flavour-masking agents, colouring agents, anti-caking agents, humectants, chelating agents, plasticisers, viscosity increasing agents, antioxidants, preservatives, stabilisers, surfactants, and buffering agents. The skilled artisan will appreciate that certain pharmaceutically-acceptable excipients may serve more than one function and may serve alternative functions depending on how much of the excipient is present in the formulation and what other excipients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (*Mack Publishing Company*), *The Handbook of Pharmaceutical Additives* (*Gower Publishing Limited*), and *The Handbook of Pharmaceutical Excipients* (*the American Pharmaceutical Association and the Pharmaceutical Press*).

The pharmaceutical compositions of the invention are prepared using techniques and methods known to those skilled in the art. Some of the methods commonly used in the art are described in *Remington's Pharmaceutical Sciences* (*Mack Publishing Company*).

Accordingly, in another aspect the invention is directed to process for the preparation of a pharmaceutical composition comprising a compound of formula (I) or a pharmaceutically acceptable salt thereof and one or more pharmaceutically-acceptable excipients which comprises mixing the ingredients. A pharmaceutical composition comprising a compound of formula (I) or a pharmaceutically acceptable salt thereof may be prepared by, for example, admixture at ambient temperature and atmospheric pressure.

In one embodiment the pharmaceutical composition is adapted for parenteral administration, particularly intravenous administration.

In one embodiment the pharmaceutical composition is adapted for oral administration.

In one embodiment the pharmaceutical composition is adapted for topical administration.

Pharmaceutical compositions adapted for parenteral administration include aqueous and non-aqueous sterile injection solutions (which may contain anti-oxidants, buffers, bacteriostats and solutes which render the composition isotonic with the blood of the intended recipient) and aqueous and non-aqueous sterile suspensions (which may include suspending agents and thickening agents). The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders suitable for incorporating into tablets or capsules may be prepared by reducing the compound to a suitable fine size (e.g. by micronisation) and mixing with a similarly prepared pharmaceutical carrier such as an edible carbohydrate, for example, starch or mannitol. Flavoring, preservative, dispersing and coloring agent can also be present.

Capsules may be made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, glidants, lubricants, sweetening agents, flavours, disintegrating agents (disintegrants) and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrants include starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of formula (I) and pharmaceutically acceptable salts thereof can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Compositions for oral administration may be designed to provide a modified release profile so as to sustain or otherwise control the release of the therapeutically active agent.

Where appropriate, dosage unit compositions for oral administration can be microencapsulated. The composition may be prepared to prolong or sustain the release as for example by coating or embedding particulate material in polymers, wax or the like.

For compositions suitable and/or adapted for oral administration, the compound of formula (I) or a pharmaceutically acceptable salt thereof, may be in a particle-size-reduced form e.g. obtained by micronisation. The preferable particle size of the size-reduced (e.g. micronised) compound or salt is defined by a $D_{50}$ value of about 0.5 to about 10 microns (for example as measured using laser diffraction).

The compounds of formula (I) and pharmaceutically acceptable salts thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Pharmaceutical compositions adapted for topical administration may be formulated as ointments, creams, suspensions, emulsions, lotions, powders, solutions, pastes, gels, foams, sprays, aerosols or oils. Such pharmaceutical compositions may include conventional additives which include, but are not limited to, preservatives, solvents to assist drug penetration, co-solvents, emollients, propellants, viscosity modifying agents (gelling agents), surfactants and carriers. In one embodiment there is provided a pharmaceutical composition adapted for topical administration which comprises between 0.01-10%, or between 0.01-1% of the compound of formula (I), or a pharmaceutically acceptable salt thereof, by weight of the composition.

For treatments of the eye or other external tissues, for example mouth and skin, the compositions are preferably applied as a topical ointment, cream, gel, spray or foam. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical compositions adapted for topical administrations to the eye include eye drops wherein the active ingredient is dissolved or suspended in a suitable carrier, especially an aqueous solvent. Compositions to be administered to the eye will have ophthalmically compatible pH and osmolality. One or more ophthalmically acceptable pH adjusting agents and/or buffering agents can be included in a composition of the invention, including acids such as acetic, boric, citric, lactic, phosphoric and hydrochloric acids; bases such as sodium hydroxide, sodium phosphate, sodium borate, sodium citrate, sodium acetate, and sodium lactate; and buffers such as citrate/dextrose, sodium bicarbonate and ammonium chloride. Such acids, bases, and buffers can be included in an amount required to maintain pH of the composition in an ophthalmically acceptable range. One or more ophthalmically acceptable salts can be included in the composition in an amount sufficient to bring osmolality of the composition into an ophthalmically acceptable range. Such salts include those having sodium, potassium or ammonium cations and chloride, citrate, ascorbate, borate, phosphate, bicarbonate, sulfate, thiosulfate or bisulfite anions.

The ocular delivery device may be designed for the controlled release of one or more therapeutic agents with multiple defined release rates and sustained dose kinetics and permeability. Controlled release may be obtained through the design of polymeric matrices incorporating different choices and properties of biodegradable/bioerodable polymers (e.g. poly(ethylene vinyl) acetate (EVA), superhydrolyzed PVA), hydroxyalkyl cellulose (HPC), methylcellulose (MC), hydroxypropyl methyl cellulose (HPMC), polycaprolactone, poly(glycolic) acid, poly(lactic) acid, polyanhydride, of polymer molecular weights, polymer crystallinity, copolymer ratios, processing conditions, surface finish, geometry, excipient addition and polymeric coatings that will enhance drug diffusion, erosion, dissolution and osmosis.

Pharmaceutical compositions for ocular delivery also include in situ gellable aqueous composition. Such a composition comprises a gelling agent in a concentration effective to promote gelling upon contact with the eye or with lacrimal fluid. Suitable gelling agents include but are not limited to thermosetting polymers. The term "in situ gellable" as used herein is includes not only liquids of low viscosity that form gels upon contact with the eye or with lacrimal fluid, but also includes more viscous liquids such as semi-fluid and thixotropic gels that exhibit substantially increased viscosity or gel stiffness upon administration to the eye. See, for example, Ludwig (2005) *Adv. Drug Deliv. Rev.* 3; 57:1595-639, herein incorporated by reference for purposes of its teachings of examples of polymers for use in ocular drug delivery.

Dosage forms for nasal or inhaled administration may conveniently be formulated as aerosols, solutions, suspensions, gels or dry powders.

For compositions suitable and/or adapted for inhaled administration, it is preferred that the compound of formula (I) or a pharmaceutically acceptable salt thereof, is in a particle-size-reduced form e.g. obtained by micronisation. The preferable particle size of the size-reduced (e.g. micronised) compound or salt is defined by a $D_{50}$ value of about 0.5 to about 10 microns (for example as measured using laser diffraction).

Aerosol formulations, e.g. for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g. co-solvents and/or surfactants to improve the dispersion characteristics and homogeneity of suspension formulations. Solution formulations may also require the addition of co-solvents such as ethanol.

For pharmaceutical compositions suitable and/or adapted for inhaled administration, the pharmaceutical composition may be a dry powder inhalable composition. Such a composition can comprise a powder base such as lactose, glucose, trehalose, mannitol or starch, the compound of formula (I) or a pharmaceutically acceptable salt thereof (preferably in particle-size-reduced form, e.g. in micronised form), and optionally a performance modifier such as L-leucine or another amino acid and/or metal salt of stearic acid such as magnesium or calcium stearate. Preferably, the dry powder inhalable composition comprises a dry powder blend of lactose e.g. lactose monohydrate and the compound of formula (I) or salt thereof. Such compositions can be administered to the patient using a suitable device such as the DISKUS® device, marketed by GlaxoSmithKline which is for example described in GB 2242134 A.

The compounds of formula (I) and pharmaceutically acceptable salts thereof may be formulated as a fluid formulation for delivery from a fluid dispenser, for example a fluid dispenser having a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in International Patent Application WO-A-2005/044354.

A therapeutically effective amount of a compound of formula (I) or a pharmaceutically acceptable salt thereof, will depend upon a number of factors including, for example, the age and weight of the patient, the precise condition requiring treatment and its severity, the nature of the formulation, and the route of administration, and will ultimately be at the discretion of the attendant physician or veterinarian. In the pharmaceutical composition, each dosage unit for oral or parenteral administration preferably contains from 0.01 mg to 3000 mg, more preferably 0.5 mg to 1000 mg, of a compound of formula (I) or a pharmaceutically acceptable salt thereof, calculated as the free base. Each dosage unit for nasal or inhaled administration preferably contains from 0.001 mg to 50 mg, more preferably 0.01 mg to 5 mg, of a compound of the formula (I) or a pharmaceutically acceptable salt thereof, calculated as the free base.

The pharmaceutically acceptable compounds of formula (I) and pharmaceutically acceptable salts thereof, can be administered in a daily dose (for an adult patient) of, for example, an oral or parenteral dose of 0.01 mg to 3000 mg per day, 0.5 mg to 1000 mg per day or 100 mg to 2500 mg per day, or a nasal or inhaled dose of 0.001 mg to 50 mg per day or 0.01 mg to 5 mg per day, of the compound of the formula (I) or a pharmaceutically acceptable salt thereof, calculated as the free base. This amount may be given in a single dose per day or more usually in a number (such as two, three, four, five or six) of sub-doses per day such that the total daily dose is the same. An effective amount of a salt thereof, may be determined as a proportion of the effective amount of the compound of formula (I) per se.

The compounds of formula (I) and pharmaceutically acceptable salts thereof may be employed alone or in combination with other therapeutic agents. Combination therapies according to the present invention thus comprise the administration of at least one compound of formula (I) or a pharmaceutically acceptable salt thereof, and the use of at least one other therapeutically active agent. The compound(s) of formula (I) and pharmaceutically acceptable salts thereof, and the other therapeutically active agent(s) may be administered together in a single pharmaceutical composition or separately and, when administered separately this may occur simultaneously or sequentially in any order. The amounts of the compound(s) of formula (I) and pharmaceutically acceptable salts thereof, and the other therapeutically active agent(s) and the relative timings of administration will be selected in order to achieve the desired combined therapeutic effect. Thus in a further aspect, there is provided a combination comprising a compound of formula (I) or a pharmaceutically acceptable salt thereof, together with one or more other therapeutically active agents.

Thus in one aspect, the compound of formula (I) or a pharmaceutically acceptable salt thereof, and pharmaceutical compositions comprising a compound of formula (I) or a pharmaceutically acceptable salt thereof, according to the invention may be used in combination with or include one or more other therapeutic agents, for example selected from antibiotics, anti-virals, glucocorticosteroids, muscarinic antagonists, beta-2 agonists and Vitamin D3 analogues. In a further embodiment a compound of formula (I) or a pharmaceutically acceptable salt thereof may be used in combination with a further therapeutic agent which is suitable for the treatment of cancer. Examples of such further therapeutic agents are described in Cancer Principles and Practice of Oncology by V. T. Devita and S. Hellman (editors), $6^{th}$ edition (2001), Lippincott Williams & Wilkins Publishers. A person of ordinary skill in the art would be able to discern which combinations of agents would be useful based on the particular characteristics of the drugs and the cancer involved. Further therapeutic agents to be used in combination with the compound of formula (I) or a pharmaceutically acceptable salt thereof include, but are not limited to, anti-microtubule agents (such as diterpenoids and vinca alkaloids); platinum coordination complexes; alkylating agents (such as nitrogen mustards, oxazaphosphorines, alkylsulphonates, nitrosoureas, and triazenes); antibiotic agents (such as anthracyclins, actinomycins and bleomycins); topoisomerase II inhibitors (such as epipodophyllotoxins); antimetabolites (such as purine and pyrimidine analogues and anti-folate compounds); topoisomerase I inhibitors (such as camptothecins; hormones and hormonal analogues); signal transduction pathway inhibitors (such as tyropsine receptor inhibitors); non-receptor tyrosine kinase angiogenesis inhibitors; immunotherapeutic agents (such as PD-1 inhibitors including nivolumab and pembrolizumab, and CTLA-4 inhibitors, including ipilimumab); proapoptotic agents; epigenetic or transcriptional modulators (such as histone deacetylase inhibitors) and cell cycle signaling inhibitors.

It will be appreciated that when the compound of formula (I) or a pharmaceutically acceptable salt thereof, is administered in combination with other therapeutic agents normally administered by the inhaled, intravenous, oral or intranasal route, that the resultant pharmaceutical composition may be administered by the same routes. Alternatively the individual components of the composition may be administered by different routes.

One embodiment of the invention encompasses combinations comprising one or two other therapeutic agents.

It will be clear to a person skilled in the art that, where appropriate, the other therapeutic agent(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic agent. It will be clear also that, where appropriate, the therapeutic agents may be used in optically pure form.

The combinations referred to above may conveniently be presented for use in the form of a pharmaceutical composition and thus pharmaceutical compositions comprising a combination as defined above together with a pharmaceutically acceptable excipient represent a further aspect of the invention.

Synthetic Routes

The compounds of the invention may be made by a variety of methods, including standard chemistry. Any previously defined variable will continue to have the previously defined meaning unless otherwise indicated. Illustrative general synthetic methods are set out in the following schemes, and can be readily adapted to prepare other compounds of the invention. Specific compounds of the invention are prepared in the Examples section.

Compounds of formula (I) may be prepared as described in Scheme 1 below:

Scheme 1

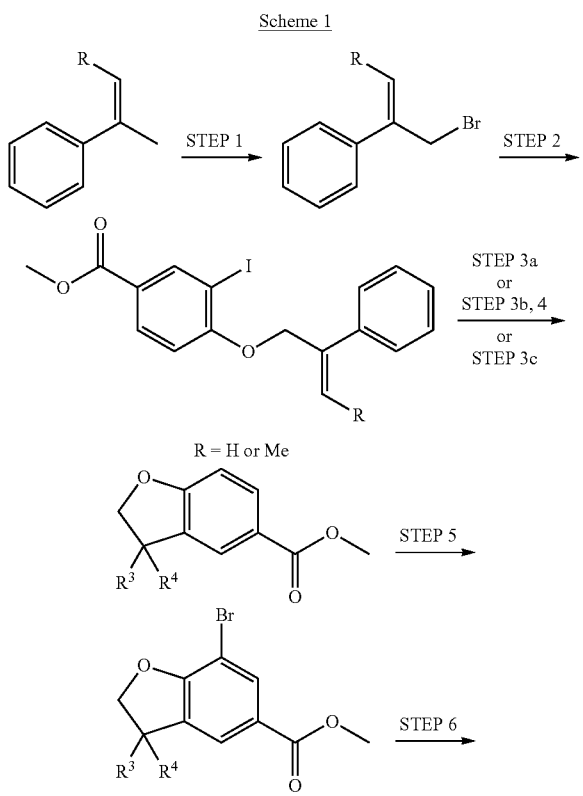

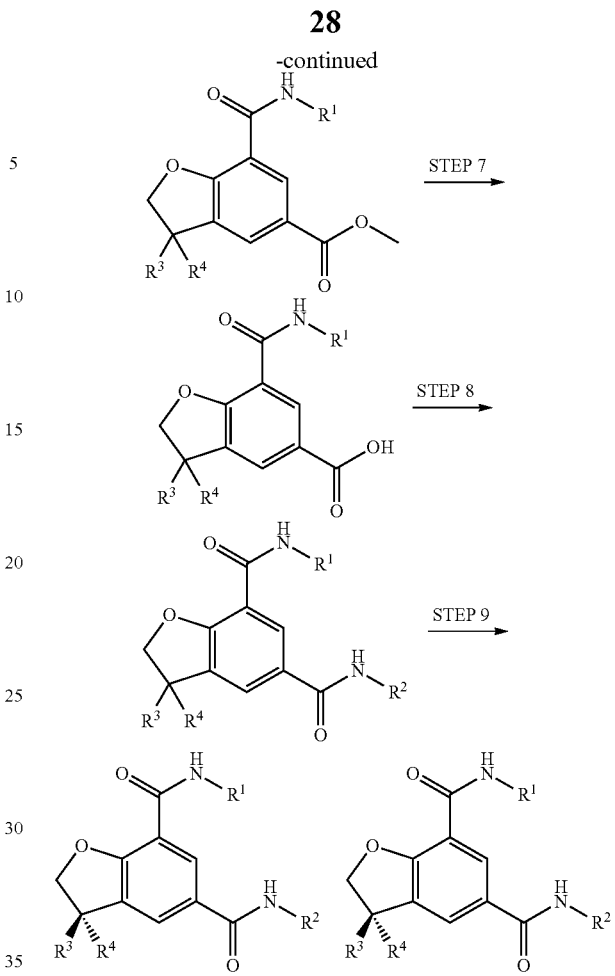

In respect of the steps shown in Scheme 1 above the following reaction conditions may be utilised to access Compounds of Formula (I) wherein $R^4$ is methyl:

Step 1: is a bromination which can be carried out using a suitable brominating agent such as NBS, in the presence of a suitable acid catalyst, such as tosic acid, in a suitable solvent such as THF, at a suitable temperature such as 100° C.

Step 2: is an alkylation of methyl 4-hydroxy-3-iodobenzoate and may be carried out, in the presence of a suitable base, such as potassium carbonate, in a suitable solvant such as acetone, at a suitable temperature, such as reflux temperature.

Step 3a: is a cyclisation and can be carried out using an appropriate palladium catalyst, such as $PdCl_2(MeCN)_2$, in the presence of a reducing agent, such as formic acid, in the presence of a base, such as 1,2,2,6,6-pentamethylpiperidine in a suitable solvent such as DMF, at an appropriate temperature such as 50° C.

Step 3b: is a cyclisation and can be carried out using an appropriate palladium catalyst, such as palladium acetate, optionally in the presence of a suitable ligand, such as triphenylphosphine, in the presence of a base, such as silver carbonate, in an adequate solvent such as DMF, at an appropriate temperature such as 80° C.

Step 3c: is a tandem cyclisation-borylation-oxidation and can be carried out using an appropriate palladium catalyst, such as Xphos Pd G2, in the presence of a borylating reagent, such as bis(pinacolato)diboron, in the presence of a base, such as potassium acetate, in a suitable solvent such as EtOH, at an appropriate temperature such as 100° C.

Step 4: is a hydrogenation and can be carried out using an appropriate catalyst, such as a palladium catalyst, such as 5% Pd/C under a hydrogen atmosphere, in a suitable solvent, such as EtOH, at an appropriate temperature, such as room temperature Step 5: is a bromination which can be carried out using a suitable brominating agent such as bromine or NBS, in a suitable solvent such as dichloromethane, at a suitable temperature such as room temperature.

Step 6: is an aminocarbonylation and can be carried out using an appropriate carbon monoxide source, such as dicobalt octacarbonyl, in the presence of a suitable primary amine of formula $R^1NH_2$, using an appropriate catalyst, such as palladium(II) acetate, optionally in the presence of a suitable ligand, such as xantphos, in the presence of a suitable tertiary amine such as DMAP, in a suitable solvent such as 1,4-dioxane, at a suitable temperature such as between 90° C. and 100° C., optionally under microwave irradiation.

Step 7: is a saponification and can be carried out using an appropriate hydroxide salt such as lithium hydroxide, in an adequate solvent such as a mixture of THF or 1,4-dioxane and water, at an appropriate temperature such as room temperature.

Step 8: is an amide formation reaction which can be carried out using an appropriate activating agent such as HATU, in the presence of an adequate base, such as a trialkylamine (for example triethylamine or diisopropylethylamine) or pyridine, and using the appropriate primary amine $R^2NH_2$, in an appropriate solvent such as dichloromethane or DMF, at an adequate temperature such as room temperature.

Step 9: is a an optional separation of isomers, which can be carried out using the appropriate chromatographic system (solid or liquid phase). This step can be performed as the last step of the synthesis of compounds of Formula (I) but can also be performed at earlier stages in the process. It should also be understood that the products from such separation steps can be obtained by method known to one skilled in the art, such as purification by chromatography on a chiral column, into single enantiomers.

EXAMPLES

General Methods
General Experimental Details
All temperatures referred to are in ° C.
As used herein the symbols and conventions used in these processes, schemes and examples are consistent with those used in the contemporary scientific literature, for example, the Journal of the American Chemical Society. Unless otherwise noted, all starting materials were obtained from commercial suppliers and used without further purification. Specifically, the following abbreviations may be used in the examples and throughout the specification:

ABBREVIATIONS

BOC/Boc tert-butyloxycarbonyl
$Boc_2O$ di-tert-butyl dicarbonate
$CHCl_3$ chloroform
Cobalt carbonyl dicobalt octacarbonyl
CV column volume
DMSO-$d_6$ deuterated dimethylsulfoxide
DCM dichloromethane
DIPEA diisopropylethylamine
DMAP 4-dimethylaminopyridine
DMF dimethylformamide
DMSO dimethylsulfoxide
DMSO-$d_6$ deuterated dimethylsulfoxide
DPPA diphenylphosphoryl azide
$Et_3N$ triethylamine
$Et_2O$ diethyl ether
EtOAc ethyl acetate
EtOH ethanol
h hour(s)
HATU O-(7-azabenzotriazol-1-yl)-N,N,N',N'-tetramethyluronium hexafluorophosphate
HCl hydrochloric acid
IPA isopropyl alcohol
$K_2CO_3$ potassium carbonate
KI potassium iodide
KOH potassium hydroxide
LCMS liquid chromatography mass spectrometry
LiOH lithium hydroxide
M molar (concentration)
MDAP mass directed autoprep
MeCN acetonitrile
MeOH methanol
$MgSO_4$ magnesium sulphate
min minute(s)
MsCl methanesulfonyl chloride
MTBE methyl tert-butyl ether
N normal (concentration)
$N_2$ nitrogen
$Na_2CO_3$ sodium carbonate
NaH sodium hydride
NaOH sodium hydroxide
$Na_2SO_4$ sodium sulphate
NBS N-bromosuccinimide
$NEt_3$ triethylamine
NUT nuclear protein in testis
Pd/C palladium on carbon
$PPh_3$ triphenylphosphine
Rt retention time
rt room temperature
sat saturated
$SiO_2$ silicon dioxide
SNAP Biotage (silica) flash chromatography cartridge
SP4 Biotage Flash purification system
SPE solid phase extraction
TBME tert-butyl methyl ether
TFA trifluoroacetic acid
THF tetrahydrofuran
TMSCl/TMS-Cl trimethylsilyl chloride
TLC thin layer chromatography
Ts tosyl
UPLC ultra performance liquid chromatography
XantPhos 1,1'-(9,9-dimethyl-9H-xanthene-4,5-diyl)bis[1,1-diphenylphosphine The names of the following compounds have been obtained using the compound naming programme "ACD Name Pro 6.02" or using the naming functionality of ChemDraw Ultra 12.0.

LCMS Methodology
Formic Method
LC Conditions
The UPLC analysis was conducted on an Acquity UPLC CSH C18 column (50 mm×2.1 mm, i.d. 1.7 μm packing diameter) at 40° C.
The solvents employed were:
A=0.1% v/v solution of formic acid in water
B=0.1% v/v solution of formic acid in acetonitrile The gradient employed was:

| Time (min) | Flow rate (mL/min) | % A | % B |
|---|---|---|---|
| 0 | 1 | 97 | 3 |
| 1.5 | 1 | 5 | 95 |
| 1.9 | 1 | 5 | 95 |
| 2.0 | 1 | 97 | 3 |

The UV detection was a summed signal from wavelength of 210 nm to 350 nm.
MS Conditions
MS: Waters ZQ
Ionisation mode: Alternate-scan positive and negative electrospray
Scan range: 100 to 1000 AMU
Scan time: 0.27 sec
Inter scan delay: 0.10 sec
High pH Method
LC Conditions
The UPLC analysis was conducted on an Acquity UPLC CSH C18 column (50 mm×2.1 mm, i.d. 1.7 µm packing diameter) at 40° C.
The solvents employed were:
A=10 mM ammonium hydrogen carbonate in water adjusted to pH10 with ammonia solution
B=acetonitrile
The gradient employed was:

| Time (min) | Flow rate (mL/min) | % A | % B |
|---|---|---|---|
| 0 | 1 | 97 | 3 |
| 0.05 | 1 | 97 | 3 |
| 1.5 | 1 | 5 | 95 |
| 1.9 | 1 | 5 | 95 |
| 2.0 | 1 | 97 | 3 |

The UV detection was a summed signal from wavelength of 210 nm to 350 nm.
MS Conditions
MS: Waters ZQ
Ionisation mode: Alternate-scan positive and negative electrospray
Scan range: 100 to 1000 AMU
Scan time: 0.27 sec
Inter scan delay: 0.10 sec
TFA Method
LC Conditions
The UPLC analysis was conducted on an Acquity UPLC CSH C18 column (50 mm×2.1 mm, i.d. 1.7 µm packing diameter) at 40° C.
The solvents employed were:
A=0.1% v/v solution of trifluoroacetic acid in water
B=0.1% v/v solution of trifluoroacetic acid in acetonitrile
The gradient employed was:

| Time (min) | Flow rate (mL/min) | % A | % B |
|---|---|---|---|
| 0 | 1 | 95 | 5 |
| 1.5 | 1 | 5 | 95 |
| 1.9 | 1 | 5 | 95 |
| 2.0 | 1 | 95 | 5 |

The UV detection was a summed signal from wavelength of 210 nm to 350 nm.
MS Conditions
MS Waters: ZQ
Ionisation mode: Alternate-scan positive and negative electrospray
Scan range: 100 to 1000 AMU
Scan time: 0.27 sec
Inter scan delay: 0.10 sec
General MDAP Purification Methods
Listed below are examples of mass-directed autopreparative chromatography (MDAP) methods that have been used or may be used in compound purification.
MDAP (High pH).
The HPLC analysis was conducted on an Xselect CSH C18 column (150 mm×30 mm i.d. 5 µm packing diameter) at ambient temperature, eluting with 10 mM ammonium bicarbonate in water adjusted to pH 10 with ammonia solution (Solvent A) and acetonitrile (Solvent B) using an elution gradient of between 0 and 100% Solvent B over 15 or 25 minutes.
The UV detection was an averaged signal from wavelength of 210 nm to 350 nm. The mass spectra were recorded on a Waters ZQ Mass Spectrometer using alternate-scan positive and negative electrospray. Ionisation data was rounded to the nearest integer.
MDAP (Formic).
The HPLC analysis was conducted on an Xselect CSH C18 column (150 mm×30 mm i.d. 5 µm packing diameter) at ambient temperature, eluting with 0.1% formic acid in water (Solvent A) and 0.1% formic acid in acetonitrile (Solvent B) using an elution gradient of between 0 and 100% solvent B over 15 or 25 minutes.
The UV detection was an averaged signal from wavelength of 210 nm to 350 nm. The mass spectra were recorded on a Waters ZQ Mass Spectrometer using alternate-scan positive and negative electrospray. Ionisation data was rounded to the nearest integer.
MDAP (TFA). The HPLC analysis was conducted on an Xselect CSH C18 column (150 mm×30 mm i.d. 5 µm packing diameter) at ambient temperature, eluting with 0.1% v/v solution of trifluoroacetic acid in water (Solvent A) and 0.1% v/v solution of trifluoroacetic acid in acetonitrile (Solvent B) using an elution gradient of between 0 and 100% solvent B over 15 or 25 minutes.
The UV detection was an averaged signal from wavelength of 210 nm to 350 nm. The mass spectra were recorded on a Waters ZQ Mass Spectrometer using alternate-scan positive and negative electrospray. Ionisation data was rounded to the nearest integer.

Intermediate 1: (3-Bromoprop-1-en-2-yl)benzene

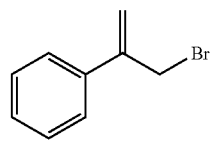

Prop-1-en-2-ylbenzene (5.50 mL, 42.3 mmol) was dissolved in THF (100 mL) at rt under $N_2$. To the resulting solution was added NBS (7.91 g, 44.4 mmol) and tosic acid (0.805 g, 4.23 mmol) and the solution was refluxed at 100° C. for 4 h. The reaction was cooled to rt, taken up in $Et_2O$ and washed with water. The organic layer was passed through a hydrophobic frit and concentrated in vacuo to afford (3-bromoprop-1-en-2-yl)benzene (7.15 g, 36.3 mmol, 86% yield) as a yellow oil.

LCMS (method Formic): Retention time 1.21, [M+H]$^+$= poor ionisation $^1$H NMR (DMSO-d$_6$, 400 MHz): δ (ppm) 7.53-7.59 (m, 2H), 7.32-7.41 (m, 3H), 5.62 (d, J=0.7 Hz, 1H), 5.58 (d, J=0.7 Hz, 1H), 4.64 (s, 2H)

Intermediate 2: Methyl 3-iodo-4-((2-phenylallyl)oxy)benzoate

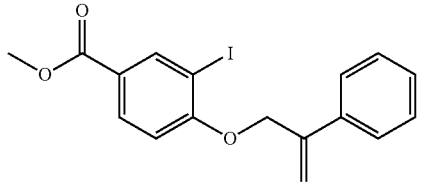 [SMILES: C=C(COc1ccc(C(=O)OC)cc1I)c1ccccc1]

Methyl 4-hydroxy-3-iodobenzoate (1.0 g, 3.6 mmol, available from commercial suppliers such as Sigma Aldrich), (3-bromoprop-1-en-2-yl)benzene (1.42 g, 7.19 mmol) and K$_2$CO$_3$ (1.491 g, 10.79 mmol) were dissolved in acetone (50 mL) and heated to 80° C. for 1 h under N$_2$. The reaction was allowed to cool before quenching with sat. NaHCO$_3$(aq) and extracting with DCM. The combined organics were passed through a hydrophobic frit and concentrated in vacuo to afford the crude product which was purified by silica gel column chromatography eluting with 0-30% EtOAc:cyclohexane, the appropriate fractions were collected and concentrated to afford methyl 3-iodo-4-((2-phenylalkyl)oxy)benzoate (1.36 g, 3.45 mmol, 96% yield) as a yellow solid.

LCMS (method Formic): Retention time 1.47, [M+H]$^+$= 395

Intermediate 3: (+/−)-Methyl 3-methyl-3-phenyl-2,3-dihydrobenzofuran-5-carboxylate

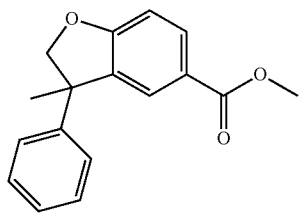 [SMILES: COC(=O)c1ccc2c(c1)C(C)(c1ccccc1)CO2]

Methyl 3-iodo-4-((2-phenylalkyl)oxy)benzoate (50.0 mg, 0.127 mmol) and PdCl$_2$(MeCN)$_2$ (3.3 mg, 0.013 mmol) were dissolved in DMF (5 mL) at rt under N$_2$. 1,2,2,6,6-Pentamethylpiperidine (0.138 mL, 0.761 mmol) was added followed by formic acid (0.019 mL, 0.51 mmol) and the reaction was heated to 50° C. for 2 h. The reaction was allowed to cool and diluted with Et$_2$O, the organic phase was washed with water and the aqueous was then extracted with EtOAc. The combined organics were passed through a hydrophobic frit and concentrated in vacuo to afford the crude product which was purified by MDAP (Formic method) to afford (+/−)-methyl 3-methyl-3-phenyl-2,3-dihydrobenzofuran-5-carboxylate (23 mg, 0.086 mmol, 68% yield) as a colourless gum.

LCMS (method Formic): Retention time 1.29, [M+H]$^+$= 269

Intermediate 4: (+/−)-Methyl 7-bromo-3-methyl-3-phenyl-2,3-dihydrobenzofuran-5-carboxylate

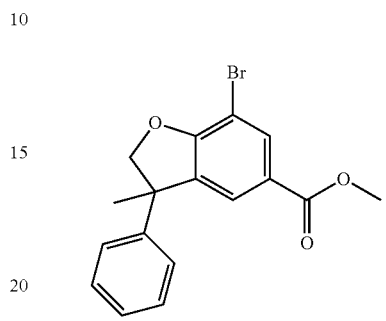

Bromine (0.134 mL, 2.61 mmol) was added to (+/−)-methyl 3-methyl-3-phenyl-2,3-dihydrobenzofuran-5-carboxylate (140 mg, 0.522 mmol) in DCM (5 mL) at rt under N$_2$. The resulting solution was stirred at rt for 1 h. The reaction was quenched with sat. sodium thiosulfate (aq) and sodium hydrosulfite was added until the reaction turned colourless. The reaction was then extracted with DCM. The organics were passed through a hydrophobic frit and concentrated in vacuo to afford (+/−)-methyl 7-bromo-3-methyl-3-phenyl-2,3-dihydrobenzofuran-5-carboxylate (172 mg, 0.495 mmol, 95% yield) as a colourless gum.

LCMS (method Formic): Retention time 1.40, [M+H]$^+$= 347, 349

Intermediate 5: (+/−)-Methyl 3-methyl-7-(methylcarbamoyl)-3-phenyl-2,3-dihydrobenzofuran-5-carboxylate

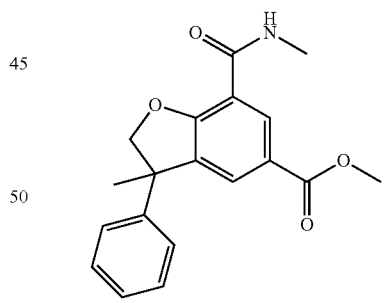

Methanamine hydrochloride (54.4 mg, 0.806 mmol), (+/−) methyl 7-bromo-3-methyl-3-phenyl-2,3-dihydrobenzofuran-5-carboxylate (140 mg, 0.403 mmol), palladium(II) acetate (45.3 mg, 0.202 mmol), xantphos (117 mg, 0.202 mmol) DMAP (222 mg, 1.81 mmol), and cobalt carbonyl (138 mg, 0.403 mmol) were dissolved in 1,4-dioxane (10 mL) and the reaction was irradiated in a biotage microwave at 100° C. for 4 h. The reaction was cooled to room temperature, diluted with water and extracted with EtOAc and Et$_2$O. The combined organics were passed through a hydrophobic frit and concentrated in vacuo to afford the crude product which was purified by silica gel column chromatography eluting with a gradient of 0-70% EtOAc:cyclohexane to afford, after concentration of the appropriate fractions, (+/−)-methyl 3-methyl-7-(methylcarbamoyl)-3-phenyl-2,3-dihydrobenzofuran-5-carboxylate (79 mg, 0.24 mmol, 60% yield) as a white solid.

LCMS (method Formic): Retention time 1.09, [M+H]$^+$=326

Intermediate 6: (+/−)-3-Methyl-7-(methylcarbamoyl)-3-phenyl-2,3-dihydrobenzofuran-5-carboxylic acid

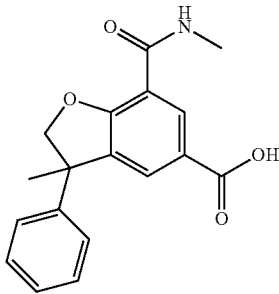 [SMILES: CNC(=O)c1cc(C(=O)O)cc2c1OCC2(C)c1ccccc1]

LiOH (10.3 mg, 0.430 mmol) and (+/−)-methyl 3-methyl-7-(methylcarbamoyl)-3-phenyl-2,3-dihydrobenzofuran-5-carboxylate (70 mg, 0.21 mmol) were dissolved in THF (2 mL) and water (2 mL). The resulting solution was heated to 50° C. and stirred for 2 h. The reaction was allowed to cool before being acidified with 2M HCl (aq) and extracted with EtOAc. The organics were passed through a hydrophobic frit and concentrated in vacuo to afford (+/−)-3-methyl-7-(methylcarbamoyl)-3-phenyl-2,3-dihydrobenzofuran-5-carboxylic acid (64 mg, 0.21 mmol, 96% yield) as a white solid.

LCMS (method Formic): Retention time 0.94, [M+H]$^+$=312

Intermediate 7: Methyl (S*)-3-methyl-7-(methylcarbamoyl)-3-phenyl-2,3-dihydrobenzofuran-5-carboxylate

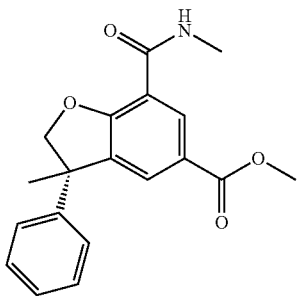 [SMILES: CNC(=O)c1cc(C(=O)OC)cc2c1OC[C@@]2(C)c1ccccc1]

(+/−)-Methyl 3-methyl-7-(methylcarbamoyl)-3-phenyl-2,3-dihydrobenzofuran-5-carboxylate (2192 mg) was submitted for chiral HPLC purification.

Analytical method: 20 μL injected on column. Elution: 50% MeOH in IPA, flow rate=1.0 mL/min, wavelength=215 nm. Column Chiralpak AS-H 250×4.6 mm (5 micron).

Preparative method: 2192 mg dissolved in 110 mL MeOH. Injections: 2.8 mL injected onto the column. Elution: 50% EtOH in heptane, flow rate=20 mL/min, wavelength=215 nm. Column Chiralpak AS-H 250×30 mm (5 μm).

Fractions from 8.5-10.5 min were collected and concentrated to give methyl (S*)-3-methyl-7-(methylcarbamoyl)-3-phenyl-2,3-dihydrobenzofuran-5-carboxylate (993 mg, 3.05 mmol, 45% yield) as a white solid LCMS (method Formic): Retention time 1.09 min, [M+H]$^+$=326

Intermediate 8: (S*)-3-Methyl-7-(methylcarbamoyl)-3-phenyl-2,3-dihydrobenzofuran-5-carboxylic acid

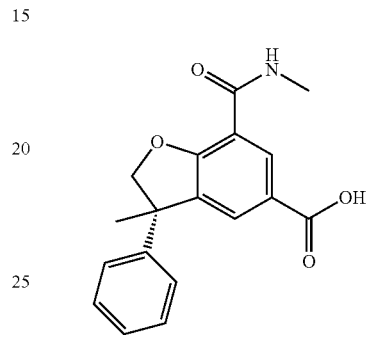

Methyl (S*)-3-methyl-7-(methylcarbamoyl)-3-phenyl-2,3-dihydrobenzofuran-5-carboxylate (993 mg, 3.05 mmol) was taken up in THF (15 mL) and MeOH (15 mL). 1 M LiOH in water (6.10 mL, 6.10 mmol) was added, and the reaction stirred at 50° C. for 3 h. The reaction was cooled to room temperature and concentrated in vacuo and the residue was taken up in water and acidified with 2 M HCl (aq). EtOAc was added, however the precipitate did not fully dissolve so the mixture was filtered to isolate a grey solid which was dried in the vacuum oven to yield batch A (682 mg).

The filtrate was separated and the organic phase was dried with Na$_2$SO$_4$, filtered and concentrated in vacuo to yield batch B as a cream solid (205 mg). Batches A and B were combined to give (S*)-3-methyl-7-(methylcarbamoyl)-3-phenyl-2,3-dihydrobenzofuran-5-carboxylic acid (885 mg, 2.70 mmol, 88% yield, purity=95%) as a grey solid.

LCMS (method Formic): Retention time 0.94, [M+H]$^+$=312

Intermediate 9: (S*)—N$^5$-(4,4-Diethoxybutyl)-N$^7$,3-dimethyl-3-phenyl-2,3-dihydrobenzofuran-5,7-dicarboxamide

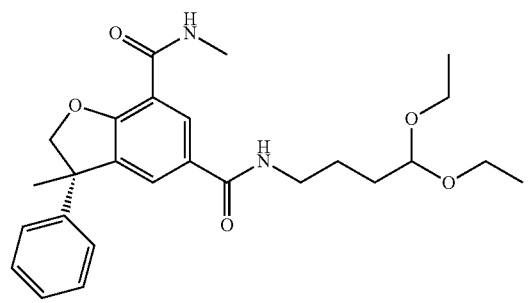 [SMILES: CCOC(CCCNC(=O)c1cc(C(=O)NC)c2c(c1)[C@](C)(c1ccccc1)CO2)OCC]

To a solution of (S*)-3-methyl-7-(methylcarbamoyl)-3-phenyl-2,3-dihydrobenzofuran-5-carboxylic acid (158 mg, 0.507 mmol) in DMF (1.5 mL) was added sequentially HATU (289 mg, 0.761 mmol) and DIPEA (0.222 mL, 1.27 mmol). The reaction was stirred for 1 min then 4,4-diethoxybutan-1-amine (0.096 mL, 0.56 mmol) was added. The reaction was stirred for 1 h. Sat. LiCl (aq) and EtOAc were added and the layers separated. The aqueous layer was extracted with further EtOAc. The organic layers were combined, back extracted with sat. LiCl (aq) and water and filtered through a cartridge fitted with a hydrophobic frit. The filtrate was evaporated in vacuo to give a dark oil. This oil was purified using silica gel column chromatography eluting with a gradient of 50-100% EtOAc:cyclohexane and the appropriate fractions collected and concentrated in vacuo to afford (S*)—$N^5$-(4,4-diethoxybutyl)-$N^7$,3-dimethyl-3-phenyl-2,3-dihydrobenzofuran-5,7-dicarboxamide (230 mg, 0.506 mmol, 100% yield) as a yellow solid LCMS (method Formic): Retention time 1.09, [M+H]$^-$=499 (formate)

Intermediate 10: (S*)—$N^5$-(3-((2r,5S)-5-(1,3-Dioxoisoindolin-2-yl)-1,3-dioxan-2-yl)propyl)-$N^7$,3-dimethyl-3-phenyl-2,3-dihydrobenzofuran-5,7-dicarboxamide

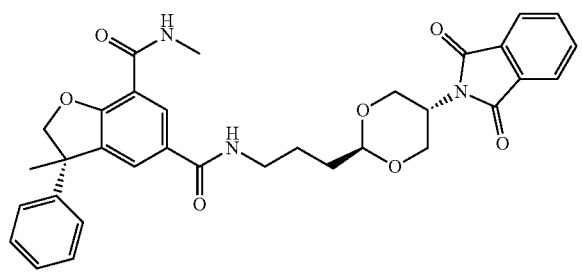 [SMILES: CNC(=O)c1cc(C(=O)NCCC[C@H]2OC[C@H](N3C(=O)c4ccccc4C3=O)CO2)cc2c1OC[C@@]2(C)c1ccccc1]

To a solution of (S*)—$N^5$-(4,4-diethoxybutyl)-$N^7$,3-dimethyl-3-phenyl-2,3-dihydrobenzofuran-5,7-dicarboxamide (230 mg, 0.506 mmol) in toluene (4 mL) was added 2-(1,3-dihydroxypropan-2-yl)isoindoline-1,3-dione (available from commercial suppliers such as Apollo scientific, 112 mg, 0.506 mmol) and p-toluenesulfonic acid monohydrate (19.2 mg, 0.101 mmol). The resulting suspension was stirred at 90° C. under $N_2$ for 2 h. The reaction mixture was allowed to cool to rt and was partitioned between EtOAc and sat. $NaHCO_3$(aq) and the layers separated. The aqueous phase was extracted with further EtOAc and the organic phases were combined, dried ($Na_2SO_4$) and filtered through a hydrophobic frit. The filtrate was evaporated in vacuo to give a yellow oil. This oil was purified uding silica gel column chromatography eluting with a gradient of 30-100% EtOAc:cyclohexane and the appropriate fractions collected and concentrated in vacuo, to afford (S*)—$N^5$-(3-((2r,5S)-5-(1,3-dioxoisoindolin-2-yl)-1,3-dioxan-2-yl)propyl)-$N^7$,3-dimethyl-3-phenyl-2,3-dihydrobenzofuran-5,7-dicarboxamide (59 mg, 0.10 mmol, 20% yield) as a clear gum.

LCMS (method Formic): Retention time 1.14, [M+H]$^+$=584

Intermediate 11: (S*)—$N^5$-(3,3-Diethoxypropyl)-$N^7$,3-dimethyl-3-phenyl-2,3-dihydrobenzofuran-5,7-dicarboxamide

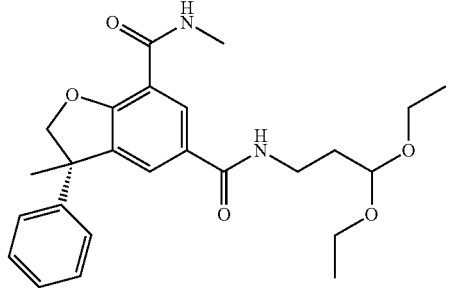 [SMILES: CCOC(CCNC(=O)c1cc(C(=O)NC)c2c(c1)[C@](C)(c1ccccc1)CO2)OCC]

To a solution of (S*)-3-methyl-7-(methylcarbamoyl)-3-phenyl-2,3-dihydrobenzofuran-5-carboxylic acid (100 mg, 0.321 mmol) in DMF (1 mL) was added sequentially HATU (183 mg, 0.482 mmol) and DIPEA (0.140 mL, 0.803 mmol). The reaction was stirred for 1 min then 3,3-diethoxypropan-1-amine (0.057 mL, 0.35 mmol) was added. The reaction was stirred for 1 h. Sat. LiCl (aq) and EtOAc were added and the layers separated. The aqueous layer was extracted with further EtOAc and the organic layers were combined, back extracted with sat. LiCl (aq) and water and filtered through a cartridge fitted with a hydrophobic frit. The filtrate was evaporated in vacuo to give a dark oil. This oil was purified using silica gel column chromatography eluting with a gradient of 60-100% EtOAc:cyclohexane and the appropriate fractions collected and concentrated in vacuo to afford (S*)—$N^5$-(3,3-diethoxypropyl)-$N^7$,3-dimethyl-3-phenyl-2,3-dihydrobenzofuran-5,7-dicarboxamide (141 mg, 0.320 mmol, 100% yield) as a yellow solid LCMS (method Formic): Retention time 1.08, [M+H]$^-$= poor ionisation Intermediate 12: (S*)—$N^5$-(2-((2r,5S)-5-(1,3-dioxoisoindolin-2-yl)-1,3-dioxan-2-yl)ethyl)-$N^7$,3-dimethyl-3-phenyl-2,3-dihydrobenzofuran-5,7-dicarboxamide

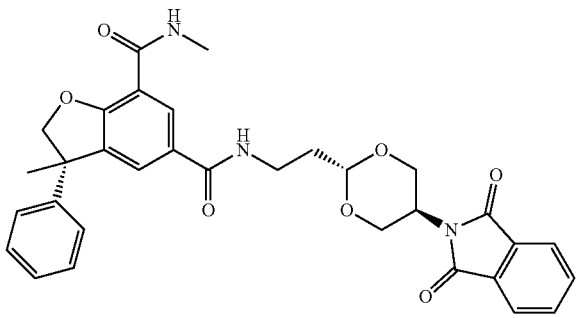 [SMILES: CNC(=O)c1cc(C(=O)NCC[C@H]2OC[C@H](N3C(=O)c4ccccc4C3=O)CO2)cc2c1OC[C@@]2(C)c1ccccc1]

To a solution of (S*)—$N^5$-(3,3-diethoxypropyl)-$N^7$,3-dimethyl-3-phenyl-2,3-dihydrobenzofuran-5,7-dicarboxamide (141 mg, 0.320 mmol) in toluene (3 mL) was added 2-(1,3-dihydroxypropan-2-yl)isoindoline-1,3-dione (available from commercial suppliers such as Apollo scientific, 70.8 mg, 0.320 mmol) and p-toluenesulfonic acid monohydrate (12 mg, 0.064 mmol). The resulting suspension was stirred at 90° C. under N₂ for 2 h. The reaction mixture was allowed to cool to rt and was partitioned between EtOAc and sat. NaHCO₃(aq) and the layers separated. The aqueous phase was extracted with further EtOAc and the organic phases were combined, dried (Na₂SO₄) and filtered through a hydrophobic frit. The filtrate was evaporated in vacuo to give a yellow oil. This oil was purified using silica gel column chromatography eluting with a gradient of 50-100% EtOAc:cyclohexane and the appropriate fractions collected and concentrated in vacuo to afford (S*)—N⁵-(2-((2r,5S)-5-(1,3-dioxoisoindolin-2-yl)-1,3-dioxan-2-yl)ethyl)-N⁷,3-dimethyl-3-phenyl-2,3-dihydrobenzofuran-5,7-dicarboxamide (135 mg, 0.237 mmol, 74% yield) as a white foam.

LCMS (method Formic): Retention time 1.12, [M+H]⁺= 570

Intermediate 13: (+/−)-Methyl 3-(hydroxymethyl)-3-phenyl-2,3-dihydrobenzofuran-5-carboxylate

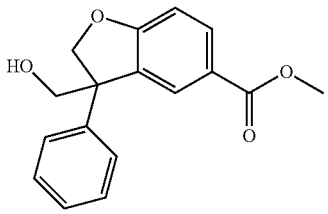 [SMILES: COC(=O)c1ccc2c(c1)C(CO)(c1ccccc1)CO2]

Methyl 3-iodo-4-((2-phenylalkyl)oxy)benzoate (500 mg, 1.27 mmol), bis(pinacolato)diboron (644 mg, 2.54 mmol), potassium acetate (373 mg, 3.81 mmol) and XPhos Pd G2 (100 mg, 0.127 mmol) were dissolved in EtOH (20 mL) at rt under N₂. The resulting solution was heated to 100° C. and stirred for 3 h. The reaction was allowed to cool to 0° C. before 2M NaOH (aq) (1.27 mL, 2.54 mmol) and H₂O₂ (1.110 mL, 12.68 mmol, 35% wt.) were added sequentially and the resulting solution stirred at 0° C. for 10 min. The reaction was quenched by the addition of sat. sodium thiosulfate (aq) and extracted with DCM. The organics were passed through a hydrophobic frit and concentrated in vacuo to afford the crude product, which was purified using silica gel column chromatography eluting with a gradient of 0-50% EtOAc:cyclohexane and the appropriate fractions collected and concentrated in vacuo to afford (+/−)-methyl 3-(hydroxymethyl)-3-phenyl-2,3-dihydrobenzofuran-5-carboxylate (199 mg, 0.702 mmol, 55% yield) as a brown gum.

LCMS (method Formic): Retention time 1.03, [M+H]⁺= 285

Intermediate 14: (+/−)-Methyl 7-bromo-3-(hydroxymethyl)-3-phenyl-2,3-dihydrobenzofuran-5-carboxylate

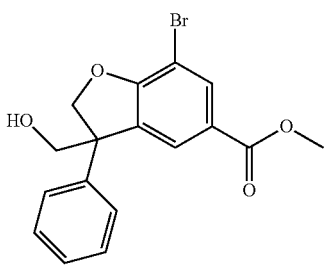 [SMILES: COC(=O)c1cc(Br)c2c(c1)C(CO)(c1ccccc1)CO2]

Bromine (0.163 mL, 3.17 mmol) was added to (+/−)-methyl 3-(hydroxymethyl)-3-phenyl-2,3-dihydrobenzofuran-5-carboxylate (180 mg, 0.633 mmol) in DCM (5 mL) at rt under N₂. The resulting solution was stirred at rt for 1 h. The reaction was quenched with sat. sodium thiosulfate (aq) and sodium hydrosulfite was added until the reaction turned colourless. The reaction was then extracted with DCM. The organics were passed through a hydrophobic frit and concentrated in vacuo to afford (+/−)-methyl 7-bromo-3-(hydroxymethyl)-3-phenyl-2,3-dihydrobenzofuran-5-carboxylate (220 mg, 0.606 mmol, 96% yield) as a colourless gum.

LCMS (method Formic): Retention time 1.18, [M+H]⁺= 363, 365

Intermediate 15: (+/−)-Methyl 3-(hydroxymethyl)-7-(methylcarbamoyl)-3-phenyl-2,3-dihydrobenzofuran-5-carboxylate

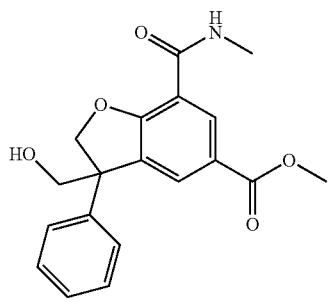 [SMILES: CNC(=O)c1cc(C(=O)OC)cc2c1OCC2(CO)c1ccccc1]

Methanamine hydrochloride (66.9 mg, 0.991 mmol), (+/−)-methyl 7-bromo-3-(hydroxymethyl)-3-phenyl-2,3-dihydrobenzofuran-5-carboxylate (180 mg, 0.496 mmol), palladium(II) acetate (55.6 mg, 0.248 mmol), xantphos (143 mg, 0.248 mmol) DMAP (272 mg, 2.23 mmol), and cobalt carbonyl (169 mg, 0.496 mmol) were dissolved in 1,4-dioxane (10 mL) and the reaction was irradiated in a biotage microwave at 100° C. for 2 h. The reaction was cooled to room temperature, diluted with water and extracted with EtOAc and Et₂O. The combined organics were passed through a hydrophobic frit and concentrated in vacuo to afford the crude product which was purified by silica gel column chromatography eluting with a gradient of 0-80% EtOAc:DCM and the appropriate fractions collected and concentrated in vacuo to afford (+/−)-methyl 3-(hydroxymethyl)-7-(methylcarbamoyl)-3-phenyl-2,3-dihydrobenzofuran-5-carboxylate (102 mg, 0.299 mmol, 60% yield) as a white solid.

LCMS (method Formic): Retention time 0.89, [M+H]⁺= 342

Intermediate 16: (+/−)-3-(Hydroxymethyl)-7-(methylcarbamoyl)-3-phenyl-2,3-dihydrobenzofuran-5-carboxylic acid

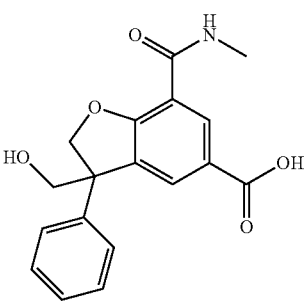 [SMILES: CNC(=O)c1cc(C(=O)O)cc2c1OCC2(CO)c1ccccc1]

LiOH (2.81 mg, 0.117 mmol) and (+/−)-methyl 3-(hydroxymethyl)-7-(methylcarbamoyl)-3-phenyl-2,3-dihydrobenzofuran-5-carboxylate (20 mg, 0.059 mmol) were dissolved in THF (0.5 mL) and water (0.5 mL). The resulting solution was stirred at rt for 2 h and then heated to 50° C. and stirred for a further 1 h. A further 1 eq. of LiOH was added and the reaction heated at 50° C. for 2 h. The reaction was allowed to cool and was then acidified with 2M HCl (aq) and extracted with EtOAc. The combined organics were passed through a hydrophobic frit and concentrated in vacuo to afford (+/−) 3-(hydroxymethyl)-7-(methylcarbamoyl)-3-phenyl-2,3-dihydrobenzofuran-5-carboxylic acid (13 mg, 0.040 mmol, 68% yield) as a white solid.

LCMS (method Formic): Retention time 0.77, [M+H]⁺=328

Intermediate 17 and 18: (S*)-Methyl 3-(hydroxymethyl)-7-(methylcarbamoyl)-3-phenyl-2,3-dihydrobenzofuran-5-carboxylate compound and (R*)-Methyl 3-(hydroxymethyl)-7-(methylcarbamoyl)-3-phenyl-2,3-dihydrobenzofuran-5-carboxylate

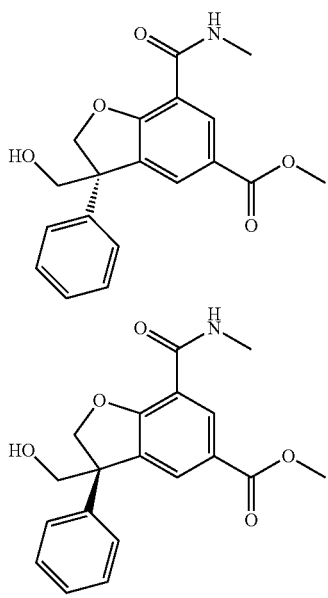

(+/−)-Methyl 3-(hydroxymethyl)-7-(methylcarbamoyl)-3-phenyl-2,3-dihydrobenzofuran-5-carboxylate (1900 mg) was submitted for chiral HPLC purification.

Analytical method: Approximately 0.5 mg of material was dissolved in 50% EtOH:heptane (1 mL); 20 μL injected onto column. Elution: 30% EtOH in heptane, flow rate=1.0 mL/min, wavelength=215 nm. Column=Chiralpak IC 250×4.6 mm (5 micron).

Preparative method: Approximatively 200 mg of material was dissolved in EtOH (2 mL) and DCM (1 mL). Injections: 3.0 mL of the solution was injected onto the column. Elution: 40% EtOH in hexane, flow rate=30 mL/min, wavelength=215 nm. Column=Chiralpak IC 250×30 mm (5 μm).

Fractions from 13-16 min were collected and concentrated to give (S*)-methyl 3-(hydroxymethyl)-7-(methylcarbamoyl)-3-phenyl-2,3-dihydrobenzofuran-5-carboxylate (832 mg, 2.44 mmol, 44%)

LCMS (method Formic): Retention time 0.87 min, [M+H]⁺=342 (Intermediate 17)

Fractions from 18-21 min were collected and concentrated to give (R*)-methyl 3-(hydroxymethyl)-7-(methylcarbamoyl)-3-phenyl-2,3-dihydrobenzofuran-5-carboxylate (792 mg, 2.32 mmol, 42%)

LCMS (method Formic): Retention time 0.87 min, [M+H]⁺=342 (Intermediate 18)

Intermediate 19: (S*)-3-(Hydroxymethyl)-7-(methylcarbamoyl)-3-phenyl-2,3-dihydrobenzofuran-5-carboxylic acid

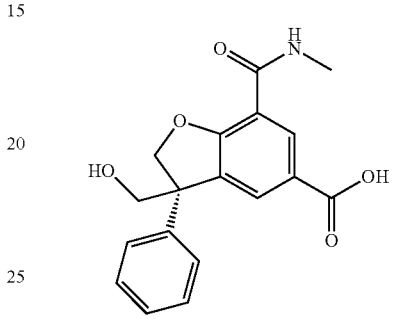

Methyl (S*)-3-(hydroxymethyl)-7-(methylcarbamoyl)-3-phenyl-2,3-dihydrobenzofuran-5-carboxylate (832 mg, 2.44 mmol) was taken up in 1:1 water:THF (14 mL) and treated with LiOH (117 mg, 4.87 mmol) and the reaction stirred at 50° C. for 4 h. The reaction was concentrated to remove the THF and then acidified to pH2 with 2N HCl (aq). A precipitate formed which was removed by filtration and dried to give (S*)-3-(hydroxymethyl)-7-(methylcarbamoyl)-3-phenyl-2,3-dihydrobenzofuran-5-carboxylic acid (753 mg, 2.30 mmol, 94% yield) as a white solid.

LCMS (method Formic): Retention time 0.75, [M+H]⁺=328

Intermediate 20: Methyl 3-iodo-4-(2-oxo-2-phenylethoxy)benzoate

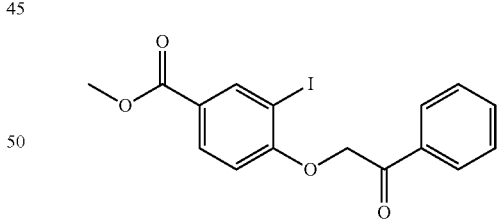

Methyl 4-hydroxy-3-iodobenzoate (available from commercial suppliers such as Sigma Aldrich, 10.0 g, 36.0 mmol), 2-bromo-1-phenylethan-1-one (available from commercial suppliers such as Sigma Aldrich, 6.83 g, 34.3 mmol) and potassium carbonate (14.2 g, 103 mmol) were suspended in acetone (100 mL) and left to stir at 80° C. under N₂ for 2.5 h. The reaction was filtered to remove excess potassium carbonate, and the filtrate was concentrated in vacuo. The residue was taken up in EtOAc, washed with 1N NaOH (aq), dried with Na₂SO₄, filtered and concentrated in vacuo to yield an orange solid (13.12 g). Et₂O (100 mL) was added to the crude product, sonicated, and stirred for 1.5 h. This was then filtered to isolate methyl 3-iodo-4-(2-oxo-2- phenylethoxy)benzoate (10.65 g, 25.50 mmol, 74% yield, purity=95%) as a cream solid.

LCMS (method Formic): Retention time 1.27, [M+H]$^+$= 397

Intermediate 21: Methyl 3-iodo-4-((2-phenylbut-2-en-1-yl)oxy)benzoate

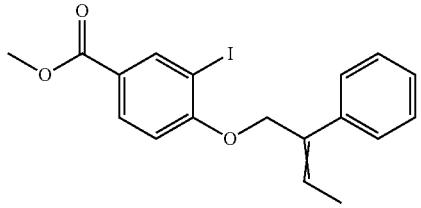 [SMILES: CC=C(COc1ccc(C(=O)OC)cc1I)c1ccccc1]

Ethyltriphenylphosphonium bromide (9.42 g, 25.4 mmol) was suspended in THF (100 mL), put under N$_2$ and cooled to 0° C. 1 M KOtBu in THF (22 mL, 22.00 mmol) was added dropwise, and the reaction was allowed to warm to rt and stirred for 1 h. Methyl 3-iodo-4-(2-oxo-2-phenylethoxy)benzoate (6.638 g, 16.75 mmol) in THF (50 mL) was added dropwise, and the reaction left to stir at rt overnight. The reaction was quenched with sat NH$_4$Cl (aq), water was added, and the layers were separated. The aqueous was extracted with EtOAc and the organics were washed with brine, dried with Na$_2$SO$_4$, filtered and concentrated in vacuo to yield a brown oil. The crude product was purified using silica gel column chromatography eluting with a gradient of 0-5% EtOAc:cyclohexane and the appropriate fractions collected and concentrated in vacuo to yield methyl 3-iodo-4-((2-phenylbut-2-en-1-yl)oxy)benzoate (4.643 g, 10.80 mmol, 65% yield, purity=95%) as a yellow oil.

LCMS (method Formic): Retention time 1.51, [M+H]$^+$= 408

Intermediate 22: (+/−)-Methyl 3-phenyl-3-vinyl-2,3-dihydrobenzofuran-5-carboxylate

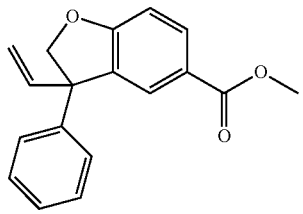 [SMILES: C=CC1(c2ccccc2)COc2ccc(C(=O)OC)cc21]

Methyl 3-iodo-4-((2-phenylbut-2-en-1-yl)oxy)benzoate (4.643 g, 11.37 mmol) was taken up in DMF (100 mL). Silver carbonate (6.27 g, 22.7 mmol) was added, and N$_2$ was bubbled through the reaction mixture. Palladium(II) acetate (0.255 g, 1.14 mmol) and triphenylphosphine (1.19 g, 4.55 mmol) were added, and the reaction left to stir at 80° C. for 27 h. Additional palladium(II) acetate (127 mg) and triphenylphosphine (600 mg) were added, and the reaction left to stir at 80° C. for 19 h. The reaction was then cooled to room temperature and filtered through Celite washing with EtOAc. Water was added to the filtrate, the layers were separated, and the aqueous was extracted with EtOAc. The combined organics were filtered through Celite again, then dried with Na$_2$SO$_4$, filtered and concentrated in vacuo to yield a brown liquid. The crude was purified in three portions using a 120 g SNAP KP-C18-HS cartridge, eluting with 45% acetonitrile in 10 mM aqueous ammonium bicarbonate solution for 2 CV then 45-90% acetonitrile over 10 CV and the appropriate fractions collected and concentrated in vacuo to yield (+/−)-methyl 3-phenyl-3-vinyl-2,3-dihydrobenzofuran-5-carboxylate (1.01 g, 3.42 mmol, 30% yield, purity=95%) as an orange gum.

LCMS (method Formic): Retention time 1.31, [M+H]$^+$= 281

Intermediate 23: (+/−)-Methyl 3-ethyl-3-phenyl-2,3-dihydrobenzofuran-5-carboxylate

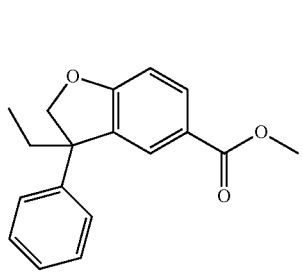 [SMILES: CCC1(c2ccccc2)COc2ccc(C(=O)OC)cc21]

5% w/w Pd/C (200 mg, 0.094 mmol) was added to the reaction vessel, this was purged with N$_2$. (+/−)-Methyl 3-phenyl-3-vinyl-2,3-dihydrobenzofuran-5-carboxylate (1.01 g, 3.60 mmol) in EtOH (20 mL) was added, and the reaction left to stir under an atmosphere of Hz (1 atm) for 4 h. The reaction mixture was filtered through Celite and concentrated in vacuo to yield (+/−)-methyl 3-ethyl-3-phenyl-2,3-dihydrobenzofuran-5-carboxylate (1.01 g, 3.40 mmol, 95% yield, purity=95%) as a pale brown gum.

LCMS (method Formic): Retention time 1.33, [M+H]$^+$= 283

Intermediate 24: (+/−)-Methyl 7-bromo-3-ethyl-3-phenyl-2,3-dihydrobenzofuran-5-carboxylate

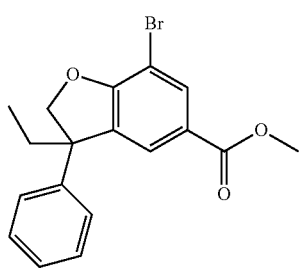 [SMILES: CCC1(c2ccccc2)COc2c(Br)cc(C(=O)OC)cc21]

(+/−)-Methyl 3-ethyl-3-phenyl-2,3-dihydrobenzofuran-5-carboxylate (1.95 g, 6.91 mmol) was taken up in DCM (60 mL), cooled to 0° C. and put under N$_2$. Br$_2$ (2.00 mL, 38.8 mmol) was added, and the reaction was allowed to warm to rt and stir for 5.5 h. The reaction was quenched with 10% sodium thiosulfate (aq) (50 mL), and sodium bisulfite was added until the reaction was pale yellow. The layers were separated and the aqueous was extracted with DCM. The combined organics were passed through a hydrophobic frit and concentrated in vacuo to yield a crude opaque yellow gum. The crude was purified using silica gel column chromatography, the solid was dry loaded onto free flowing silica and placed on top of a 100 g Si pre packed column and eluted with 1-10% EtOAc:cyclohexane and the appropriate fractions collected and concentrated in vacuo to yield (+/−)-methyl 7-bromo-3-ethyl-3-phenyl-2,3-dihydrobenzofuran-5-carboxylate (2.10 g, 5.53 mmol, 80% yield, purity=95%) as a yellow oil.

LCMS (method Formic): Retention time 1.44, [M+H]$^+$= 362

Intermediate 25: (+/−)-Methyl 3-ethyl-7-(methylcarbamoyl)-3-phenyl-2,3-dihydrobenzofuran-5-carboxylate

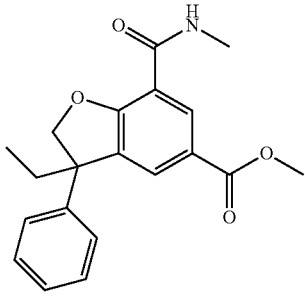 [SMILES: CCC1(c2ccccc2)COc2c(C(=O)NC)cc(C(=O)OC)cc21]

Methanamine hydrochloride (226 mg, 3.35 mmol), palladium(II) acetate (60.2 mg, 0.268 mmol), xantphos (155 mg, 0.268 mmol), DMAP (737 mg, 6.04 mmol), imidazole (183 mg, 2.68 mmol) and cobalt carbonyl (229 mg, 0.671 mmol) were sealed in a microwave vial. The vessel was purged with $N_2$ and (+/−)-methyl 7-bromo-3-ethyl-3-phenyl-2,3-dihydrobenzofuran-5-carboxylate (510 mg, 1.34 mmol) in 1,4-dioxane (12 mL) was added. The reaction vessel was sealed and irradiated in a microwave reactor to 90° C. for 4 h. The reaction mixture was cooled to room temperature, diluted with EtOAc, water was added, the mixture was filtered through Celite, and the filtrate was separated. The organic layer was washed with brine, a grey precipitate formed. The mixture was filtered through Celite again, and the biphasic filtrate was separated. The organic layer was dried with $Na_2SO_4$, filtered and concentrated in vacuo to yield a brown solid. This crude solid was purified using silica gel column chromatography eluting with a gradient of 5-50% EtOAc:cyclohexane and the appropriate fractions collected and concentrated in vacuo. This whole process was repeated ×3 to process 1.5 g of SM to yield (+/−)-methyl 3-ethyl-7-(methylcarbamoyl)-3-phenyl-2,3-dihydrobenzofuran-5-carboxylate (1.007 g, 2.820 mmol, 70% yield, purity=95%)

LCMS (method Formic): Retention time 1.13, $[M+H]^+=340$

Intermediate 26 and 27: (S*)-Methyl 3-ethyl-7-(methylcarbamoyl)-3-phenyl-2,3-dihydrobenzofuran-5-carboxylate compound with (R*)-methyl 3-ethyl-7-(methylcarbamoyl)-3-phenyl-2,3-dihydrobenzofuran-5-carboxylate (1:1)

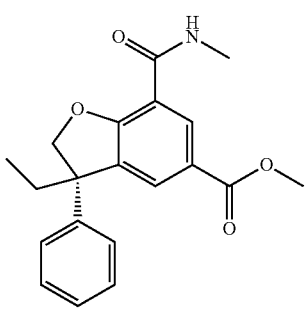

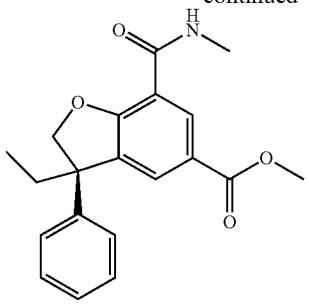

(+/−)-Methyl 3-ethyl-7-(methylcarbamoyl)-3-phenyl-2,3-dihydrobenzofuran-5-carboxylate (1457 mg) was submitted for chiral HPLC purification.

Analytical method: Approximatively 0.5 mg of material was dissolved in 50% EtOH:heptane (1 mL); 5 µL injected onto column. Elution: 30% EtOH (+0.2% isopropylamine) in heptane, flow rate=1.0 mL/min, wavelength=215 nm. Column=Chiralpak IC 250×4.6 mm (5 micron).

Preparative method: Approximatively 1457 mg of material was dissolved in EtOH (5 mL). Injections: 1.0 mL of the solution was injected onto the column. Elution: 20% EtOH (+0.2% isopropylamine) in hexane, flow rate=30 mL/min, wavelength=215 nm. Column= Chiralpak IC 250×30 mm (5 µm).

Fractions from 26-33 min were collected and concentrated to give (S*)-methyl 3-ethyl-7-(methylcarbamoyl)-3-phenyl-2,3-dihydrobenzofuran-5-carboxylate (711 mg, 1.99 mmol, yield 49%, purity=95%)

LCMS (method Formic): Retention time 1.13 min, $[M+H]^+=340$ (Intermediate 26)

Fractions from 37-48 min were collected and concentrated to give (R*)-methyl 3-ethyl-7-(methylcarbamoyl)-3-phenyl-2,3-dihydrobenzofuran-5-carboxylate (673 mg, 1.88 mmol, yield=46%, purity=95%)

LCMS (method Formic): Retention time 1.13 min, $[M+H]^+=340$ (Intermediate 27)

Intermediate 28: (S*)-3-Ethyl-7-(methylcarbamoyl)-3-phenyl-2,3-dihydrobenzofuran-5-carboxylic acid

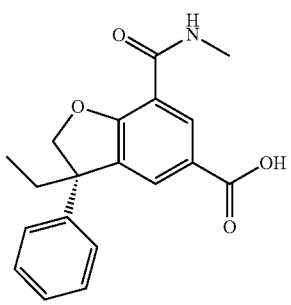 [SMILES: CC[C@@]1(c2ccccc2)COc2c(C(=O)NC)cc(C(=O)O)cc21]

Methyl (S*)-3-ethyl-7-(methylcarbamoyl)-3-phenyl-2,3-dihydrobenzofuran-5-carboxylate (709 mg, 2.09 mmol) was taken up in 1,4-dioxane (10 mL) and water (5 mL). 1 M LiOH in water (4.18 mL, 4.18 mmol) was added, and the reaction left to stir at 50° C. for 1.5 h. The reaction was cooled to room temperature, concentrated in vacuo and the residue was taken up in water (15 mL) and acidified with 2 M HCl (aq). The white precipitate formed was isolated by filtration and dried in the vacuum oven overnight to yield (S*)-3-ethyl-7-(methylcarbamoyl)-3-phenyl-2,3-dihydrobenzofuran-5-carboxylic acid (514 mg, 1.50 mmol, 72% yield, purity=95%) as a white solid.

LCMS (method Formic): Retention time 0.98, [M+H]⁺= 326

Intermediate 29: (S*)—N⁵-(3,3-diethoxypropyl)-3-ethyl-N⁷-methyl-3-phenyl-2,3-dihydrobenzofuran-5,7-dicarboxamide

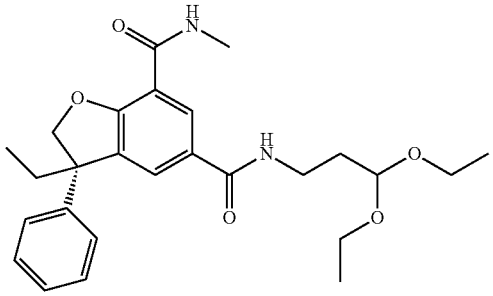 [SMILES: CCOC(CCNC(=O)c1cc(C(=O)NC)c2c(c1)[C@](CC)(c1ccccc1)CO2)OCC]

To a solution of (S*)-3-ethyl-7-(methylcarbamoyl)-3-phenyl-2,3-dihydrobenzofuran-5-carboxylic acid (75 mg, 0.23 mmol) in DMF (1 mL) was added sequentially HATU (131 mg, 0.346 mmol) and DIPEA (0.101 mL, 0.576 mmol). The reaction was stirred for 1 min then 3,3-diethoxypropan-1-amine (available from commercial suppliers such as Sigma Aldrich, 0.041 mL, 0.25 mmol) was added. The reaction was stirred for 1 h, after which sat. LiCl (aq) and EtOAc were added and the layers separated. The aqueous layer was extracted with further EtOAc. The organic layers were combined, back extracted with sat. LiCl (aq) and water and filtered through a cartridge fitted with a hydrophobic frit. The filtrate was evaporated in vacuo to give a dark oil. This oil was purified using silica gel column chromatography eluting with a gradient of 50-100% EtOAc:cyclohexane and the appropriate fractions collected and concentrated in vacuo to yield (S*)—N⁵-(3,3-diethoxypropyl)-3-ethyl-N⁷-methyl-3-phenyl-2,3-dihydrobenzofuran-5,7-dicarboxamide (116 mg, 0.230 mmol, 100% yield) as a pale yellow oil.

LCMS (method Formic): Retention time 1.12, [M+H]⁻= 499 (formate)

Intermediate 30: (S*)—N⁵-(2-((2r,5S)-5-(1,3-dioxoisoindolin-2-yl)-1,3-dioxan-2-yl)ethyl)-3-ethyl-N⁷-methyl-3-phenyl-2,3-dihydrobenzofuran-5,7-dicarboxamide

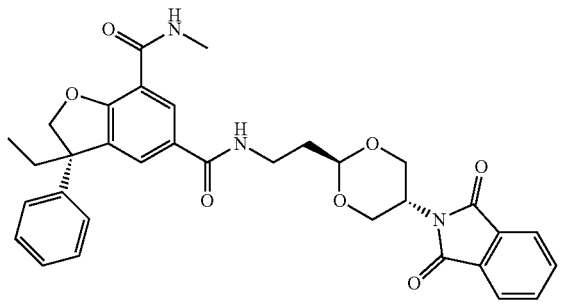 [SMILES: CC[C@@]1(c2ccccc2)COc2c(C(=O)NC)cc(C(=O)NCC[C@H]3OC[C@H](N4C(=O)c5ccccc5C4=O)CO3)cc21]

To a solution of (S*)—N⁵-(3,3-diethoxypropyl)-3-ethyl-N⁷-methyl-3-phenyl-2,3-dihydrobenzofuran-5,7-dicarboxamide (116 mg, 0.230 mmol) in toluene (3 mL) was added 2-(1,3-dihydroxypropan-2-yl)isoindoline-1,3-dione (available from commercial suppliers such as Apollo scientific, 50.8 mg, 0.230 mmol) and p-toluenesulfonic acid monohydrate (8.7 mg, 0.046 mmol). The resulting suspension was stirred at 90° C. under N₂ for 2 h. The reaction mixture was allowed to cool to rt and partitioned between EtOAc and sat. NaHCO₃(aq) and the layers separated. The aqueous phase was extracted with further EtOAc and the organic phases were combined, dried (Na₂SO₄) and filtered through a hydrophobic frit. The filtrate was evaporated in vacuo to give a yellow oil. This oil was purified using silica gel column chromatography eluting with a gradient of 40-100% EtOAc:cyclohexane and the appropriate fractions collected and concentrated in vacuo to give (S*)—N⁵-(2-((2r,5S)-5-(1,3-dioxoisoindolin-2-yl)-1,3-dioxan-2-yl)ethyl)-3-ethyl-N⁷-methyl-3-phenyl-2,3-dihydrobenzofuran-5,7-dicarboxamide (105 mg, 0.180 mmol, 78% yield) as a white foam LCMS (method Formic): Retention time 1.15, [M+H]⁺= 584

Intermediate 31: (S*)—N⁵-(4,4-diethoxybutyl)-3-ethyl-N⁷-methyl-3-phenyl-2,3-dihydrobenzofuran-5,7-dicarboxamide

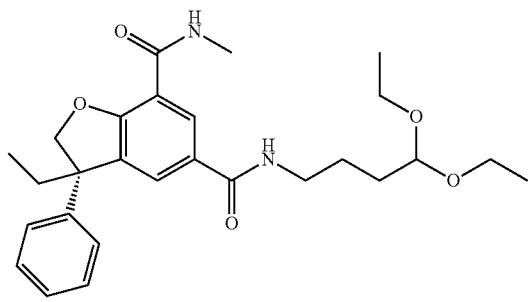 [SMILES: CCOC(CCCNC(=O)c1cc(C(=O)NC)c2c(c1)[C@](CC)(c1ccccc1)CO2)OCC]

To a solution of (S*)-3-ethyl-7-(methylcarbamoyl)-3-phenyl-2,3-dihydrobenzofuran-5-carboxylic acid (75 mg, 0.23 mmol) in DMF (1 mL) was added sequentially HATU (131 mg, 0.346 mmol) and DIPEA (0.101 mL, 0.576 mmol). The reaction was stirred for 1 min then 4,4-diethoxybutan-1-amine (available from commercial suppliers such as Sigma Aldrich, 0.044 mL, 0.25 mmol) was added. The reaction was stirred for 1 h, after which sat. LiCl (aq) and EtOAc were added and the layers separated. The aqueous layer was extracted with further EtOAc. The organic layers were combined, back extracted with sat. LiCl (aq) and water and filtered through a cartridge fitted with a hydrophobic frit. The filtrate was evaporated in vacuo to give a dark oil. This oil was purified using silica gel column chromatography eluting with a gradient of 40-100% EtOAc:cyclohexane and the appropriate fractions collected and concentrated in vacuo to give (S*)—N⁵-(4,4-diethoxybutyl)-3-ethyl-N⁷-methyl-3-phenyl-2,3-dihydrobenzofuran-5,7-dicarboxamide (115 mg, 0.221 mmol, 96% yield) as a yellow foam.

LCMS (method Formic): Retention time 1.14, [M+H]⁻= 512

Intermediate 32: (S*)—N⁵-(3-((2r,5S)-5-(1,3-dioxoisoindolin-2-yl)-1,3-dioxan-2-yl)propyl)-3-ethyl-N⁷-methyl-3-phenyl-2,3-dihydrobenzofuran-5,7-dicarboxamide

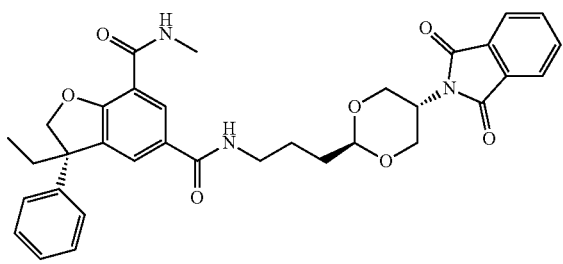 [SMILES: CC[C@@]1(c2ccccc2)COc2c(C(=O)NC)cc(C(=O)NCCC[C@H]3OC[C@H](N4C(=O)c5ccccc5C4=O)CO3)cc21]

To a solution of (S*)—N⁵-(4,4-diethoxybutyl)-3-ethyl-N⁷-methyl-3-phenyl-2,3-dihydrobenzofuran-5,7-dicarboxamide (115 mg, 0.221 mmol) in toluene (4 mL) was added 2-(1,3-dihydroxypropan-2-yl)isoindoline-1,3-dione (available from commercial suppliers such as Apollo scientific, 48.9 mg, 0.221 mmol) and p-toluenesulfonic acid monohydrate (8.4 mg, 0.044 mmol). The resulting suspension was stirred at 90° C. under N₂ for 2 h. The reaction mixture was allowed to cool to rt and was partitioned between EtOAc and sat. NaHCO₃(aq) and the layers separated. The aqueous phase was extracted with further EtOAc and the organic phases were combined, dried (Na₂SO₄) and filtered through a hydrophobic frit. The filtrate was evaporated in vacuo to give a yellow oil. This oil was purified using silica gel column chromatography eluting with a gradient of 40-100% EtOAc:cyclohexane and the appropriate fractions collected and concentrated in vacuo to give (S*)—N⁵-(3-((2r,5S)-5-(1,3-dioxoisoindolin-2-yl)-1,3-dioxan-2-yl)propyl)-3-ethyl-N⁷-methyl-3-phenyl-2,3-dihydrobenzofuran-5,7-dicarboxamide (80 mg, 0.13 mmol, 61% yield) as a clear gum.

LCMS (method Formic): Retention time 1.18, [M+H]⁻= 598

Intermediate 33: (1R,5S,6r))-3-Oxabicyclo[3.1.0]hexane-6-carboxylic acid

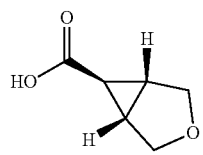

Lithium hydroxide (751 mg, 31.4 mmol) was added at rt to a solution of (1R,5S,6r)-ethyl 3-oxabicyclo[3.1.0]hexane-6-carboxylate (1.00 g, 6.27 mmol, commercially available from, for example, Pharmablock) in water (10 mL), THF (10 mL) and MeOH (10 mL). The resulting suspension was stirred 3 h at this temperature then was concentrated in vacuo. The residue was dissolved in a minimum amount of water, and treated with hydrochloric acid (5 mL, 25% w/w in water). The aqueous phase was extracted 4 times with MeOH/DCM and the combined organic phases were dried over a hydrophobic frit, concentrated in vacuo, to give (1R,5S,6r)-3-oxabicyclo[3.1.0]hexane-6-carboxylic acid (750 mg, 93%) which was used in the next step without further purification.

¹H NMR (400 MHz, DMSO-d₆) δ ppm 12.13 (s, 1H) 3.80 (d, J=8.6 Hz, 2H) 3.62 (d, J=8.6 Hz, 2H) 2.00-2.15 (m, 2H) 1.32 (t, J=3.1 Hz, 1H)

Intermediate 34: Benzyl (1R,5S,6r))-3-oxabicyclo[3.1.0]hexan-6-ylcarbamate

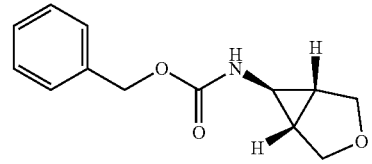 [SMILES: O=C(N[C@H]1[C@@H]2COC[C@@H]21)OCc1ccccc1]

A solution of (1R,5S,6r)-3-Oxabicyclo[3.1.0]hexane-6-carboxylic acid (340 mg, 2.65 mmol) in toluene (12 mL) at rt was treated with NEt₃ (1.11 mL, 7.96 mmol), diphenyl phosphorazidate (0.686 mL, 3.18 mmol) and benzyl alcohol (0.552 mL, 5.31 mmol) and the resulting mixture was heated at reflux for 2 h then was cooled to rt. The solution was diluted with EtOAc (10 mL) and washed with water (10 mL) and a sat. NaHCO₃(aq) (10 mL). The organic phase was dried and evaporated and the residue purified by chromatography on a 25 g silica column eluting with 0-50% EtOAc:cyclohexane and the product-containing fractions were evaporated in vacuo to give benzyl (1R,5S,6r)-3-oxabicyclo[3.1.0]hexan-6-ylcarbamate (460 mg, 74%) as a white solid.

LCMS (Formic): Retention time 0.83 min, [M+H]⁺= 234.3.

Intermediate 35: (1R,5S,6r))-3-Oxabicyclo[3.1.0]hexan-6-amine, hydrochloride

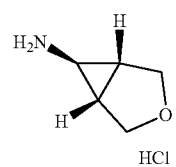

Benzyl (1R,5S,6r)-3-oxabicyclo[3.1.0]hexan-6-ylcarbamate (460 mg, 1.97 mmol) was dissolved in EtOH (20 mL) and the reaction was hydrogenated using an H-cube (settings: room temperature, 1 bar, 1 mL/min flow rate) and 10% Pd/C CatCart 30 as the catalyst. The reaction was cycled though the H-Cube for 1.5 h before acidifying the mixture with HCl (7M aqueous, 1.33 mL, 9.86 mmol) and evaporating in vacuo to yield an oily solid. The solid was dried in vacuo over 2 days to yield the desired product (1R,5S,6r)-3-oxabicyclo[3.1.0]hexan-6-amine, hydrochloride (262 mg, 93%) as an off-white solid.

¹H NMR (400 MHz, DMSO-d₆) δ ppm 8.48 (br. s., 3H) 3.80 (d, J=8.8 Hz, 2H) 3.59 (d, J=8.6 Hz, 2H) 2.24 (t, J=2.3 Hz, 1H) 2.07 (t, J=2.6 Hz, 2H).

Intermediate 36: tert-Butyl(cyclopent-3-en-1-yloxy)dimethylsilane

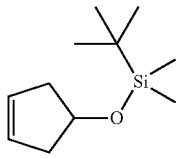

Cyclopent-3-en-1-ol (5.00 g, 59.4 mmol, commercially available from, for example, Astatech) was dissolved in DCM (100 mL) and TBDMS-Cl (8.96 g, 59.4 mmol) and imidazole (4.86 g, 71.3 mmol) were added, then the resulting suspension was stirred at rt over the weekend. The mixture was washed with water (2×100 mL), dried and evaporated in vacuo to give tert-butyl(cyclopent-3-en-1-yloxy)dimethylsilane (12.0 g, 60.7 mmol, 102% yield) as a pale yellow liquid.

$^1$H NMR (400 MHz, CDCl$_3$) δ ppm 5.68 (s, 2H) 4.50-4.62 (m, 1H) 2.59 (dd, J=14.9, 6.8 Hz, 2H) 2.23-2.37 (m, 2H) 0.91 (s, 9H) 0.09 (s, 6H).

Intermediate 37: (1R,5S,6r)-Ethyl 3-((tert-butyldimethylsilyl)oxy)bicyclo[3.1.0]hexane-6-carboxylate

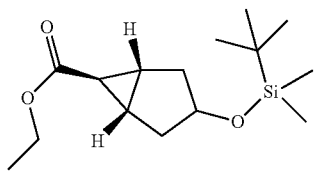 [SMILES: CCOC(=O)[C@H]1[C@@H]2CC(O[Si](C)(C)C(C)(C)C)C[C@@H]21]

Ethyl diazoacetate (6.90 mL, 66.5 mmol, commercially available from, for example, Sigma Aldrich) was dissolved in DCM (150 mL) and added dropwise over ~5 h to a mixture of rhodium(II) acetate dimer (1.00 g, 2.26 mmol, commercially available from, for example, Sigma Aldrich) and tert-butyl(cyclopent-3-en-1-yloxy)dimethylsilane (12.0 g, 60.5 mmol) in DCM (150 mL) at rt. The resulting green solution was stirred overnight at this temperature, then evaporated in vacuo to give a green liquid. This was loaded onto a 340 g silica column and eluted with 0-40% EtOAc:cyclohexane. Appropriate fractions were evaporated in vacuo to give ethyl (1R,5S,6r)-3-((tert-butyldimethylsilyl)oxy)bicyclo[3.1.0]hexane-6-carboxylate (5.5 g, 19 mmol, 32% yield) as a colourless liquid—NMR consistent with the desired product as a mixture of isomers at the silyl ether position in about 3:1 ratio and this was carried through crude to the next step.

LCMS (2 min High pH): Rt=0.96 min.

Intermediate 38: Benzyl ((1R,5S,6r))-3-((tert-butyldimethylsilyl)oxy)bicyclo[3.1.0]hexan-6-yl) carbamate

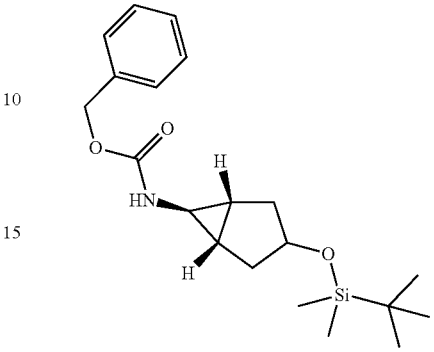

Step 1: NaOH (20 mL, 40 mmol, 2M aq.) was added to a solution of (1R,5S,6r)-ethyl 3-((tert-butyldimethylsilyl)oxy)bicyclo[3.1.0]hexane-6-carboxylate (5.0 g, 17 mmol) in EtOH (50 mL) at rt and the mixture was stirred for 3 h. The mixture was evaporated in vacuo to about 30 mL volume, then diluted with water (30 mL) and washed with Et$_2$O (50 mL). The Et$_2$O washings from the workup were dried and evaporated in vacuo to give recovered starting material, (1R,5S,6r)-ethyl 3-((tert-butyldimethylsilyl)oxy)bicyclo[3.1.0]hexane-6-carboxylate This was dissolved in ethanol (30 mL) and 2M aqueous NaOH solution (20 mL, 2M aq.) was added, then the mixture was heated at 70° C. for 3 h, then evaporated in vacuo. The residue was dissolved in water (50 mL) and washed with Et$_2$O (50 mL), then the aqueous layer was acidified with 2M HCl (20 mL) and extracted with EtOAc (2×50 mL). The combined organics were dried and evaporated in vacuo to give (1R,5S,6r)-3-((tert-butyldimethylsilyl)oxy)bicyclo[3.1.0]hexane-6-carboxylic acid (1.9 g, 7.4 mmol, 42% yield) as a pale yellow solid. The product was carried through to the next step without purification. Step 2: (1R,5S,6r)-3-((tert-Butyldimethylsilyl)oxy)bicyclo[3.1.0]hexane-6-carboxylic acid (1.8 g, 7.0 mmol) was dissolved in a mixture of toluene (20 mL) and Et$_3$N (1.957 mL, 14.04 mmol), then DPPA (1.81 mL, 8.42 mmol) was added and the mixture was stirred for 30 min at rt. Benzyl alcohol (1.095 mL, 10.53 mmol) was added and the mixture heated at 100° C. for 4 h, then cooled to rt. EtOAc (100 mL) was added and the solution was washed with water (2×100 mL), then dried over sodium sulfate, filtered and the filtrate evaporated in vacuo to give a pale yellow oil. This was dissolved in DCM (10 mL) and loaded onto a 50 g silica column, then eluted with 0-30% EtOAc/cyclohexane and the product-containing fractions were collected and evaporated in vacuo to give benzyl ((1R,5S,6r)-3-((tert-butyldimethylsilyl)oxy)bicyclo[3.1.0]hexan-6-yl) carbamate (1.90 g, 5.26 mmol, 75% yield) as a pale yellow oil, NMR consistent with desired product as a mixture of isomers in approximately 2:1 ratio. The compound was taken through to the next step without further purification.

LCMS (2 min Formic): Rt=1.56 min, [MI-1]±=362.6.

Intermediate 39: (1R,3s,5S,6r))-3-((tert-Butyldimethylsilyl)oxy)bicyclo[3.1.0]hexan-6-amine (9:1 Mix of Diastereomers)

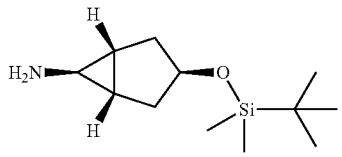

Benzyl ((1R,5S,6r)-3-((tert-butyldimethylsilyl)oxy)bicyclo[3.1.0]hexan-6-yl)carbamate (0.52 g, 1.438 mmol) was dissolved in EtOH (30 mL) and hydrogenated in the H-Cube at atmospheric pressure and 1 mL/min flow rate. The eluent was evaporated in vacuo and the residue purified using silica gel column chromatography eluting with a gradient of 0-10% 2M methanolic ammonia:DCM and the appropriate fractions collected and concentrated in vacuo to give: (1R,3S,5S,6r)-3-((tert-butyldimethylsilyl)oxy)bicyclo[3.1.0]hexan-6-amine (9:1 mix of diastereomers) (12 mg, 37%)

$^1$H NMR (400 MHz, CDCl$_3$) δ ppm 3.79 (t, J=7.6 Hz, 1H) 2.01 (dd, J=12.8, 7.2 Hz, 2H) 1.95 (s, 1H) 1.62-1.69 (m, 2H) 1.53 (br. s., 2H) 1.17 (dd, J=3.2, 1.7 Hz, 2H) 0.82-0.87 (m, 9H) −0.03-0.02 (m, 6H)

Intermediate 40: tert-Butyl ((1S,2S)-2-methylcyclopropyl)carbamate

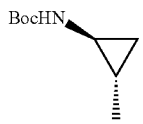

(1S,2S)-2-Methylcyclopropanecarboxylic acid (200 mg, 2.00 mmol, commercially available from, for example, Enamine) and triethylamine (0.90 mL, 6.5 mmol) were dissolved in tert-butanol (4 mL). Diphenyl phosphorylazide (0.47 mL, 2.2 mmol) was added and the reaction was heated at 90° C. The reaction was followed by TLC (eluting with 50:50 EtOAc:cyclohexane, visualising with Ninhydrin). After 2 h, TLC showed the formation of a less polar product as well as residual SM. The reaction was stirred for 3 days. The solution was partitioned between EtOAc (10 mL), and a saturated sodium bicarbonate aqueous solution (10 mL). The layers were separated and the aqueous phase was extracted with EtOAc (2×20 mL). The combined organics were dried over a hydrophobic frit and concentrated in vacuo to give 1.08 g of a yellow solid. This was purified by chromatography on SiO$_2$ (Biotage® SNAP 25 g cartridge, eluting with 0-50% EtOAc/cyclohexane). The appropriate fractions were concentrated to give tert-butyl ((1S,2S)-2-methylcyclopropyl)carbamate (223 mg, 1.17 mmol, 59% yield) as a white crystalline solid.

$^1$H NMR (400 MHz, MeOH-d$_4$) δ ppm 2.05-2.14 (m, 1H) 1.43 (br. s., 9H) 1.04 (d, J=5.9 Hz, 3H) 0.78 (m, J=8.9, 6.0, 6.0, 3.1 Hz, 1H) 0.59 (dt, J=8.9, 4.3 Hz, 1H) 0.39 (q, J=6.0 Hz, 1H).

Exchangeable Proton not Observed.

Intermediate 41: (1S,2S)-2-Methylcyclopropanamine hydrochloride

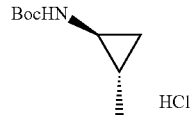

tert-Butyl ((1S,2S)-2-methylcyclopropyl)carbamate (215 mg, 1.26 mmol) was stirred at room temperature in 4 M HCl in dioxane (16 mL, 64.0 mmol). The reaction was followed by TLC (50:50 EtOAc:cyclohexane, visualising with Ninhydrin). After 30 min, the solution was concentrated in vacuo to give (1S,2S)-2-methylcyclopropanamine hydrochloride (151 mg, 1.12 mmol, 89% yield) as an off white solid.

$^1$H NMR (400 MHz, DMSO-d$_6$) δ ppm 8.27 (br. s., 3H) 2.25 (br. s., 1H) 1.06-1.18 (m, 1H) 0.99 (d, J=6.1 Hz, 3H) 0.85 (ddd, J=9.4, 5.6, 3.8 Hz, 1H) 0.48 (dt, J=7.5, 5.9 Hz, 1H).

Intermediate 42: (+/−) 3-ethyl-7-(methylcarbamoyl)-3-phenyl-2,3-dihydrobenzofuran-5-carboxylic acid

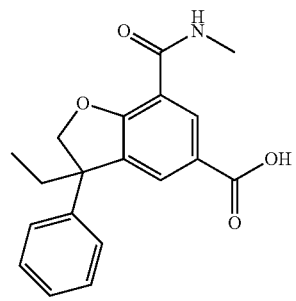 [SMILES: CCC1(c2ccccc2)COc2c(C(=O)NC)cc(C(=O)O)cc21]

(+/−) methyl 3-ethyl-7-(methylcarbamoyl)-3-phenyl-2,3-dihydrobenzofuran-5-carboxylate (2 g, 5.89 mmol, Intermediate 2S) and lithium hydroxide (0.282 g, 11.8 mmol) were stirred in a mixture of THF (10 mL) and water (10 mL) at 50° C. for 18 h. The reaction was concentrated to remove the THF and was acidified to pH 2 with 2M HCl (aq), a precipitate formed which was removed by filtration and dried to give (+/−) 3-ethyl-7-(methylcarbamoyl)-3-phenyl-2,3-dihydrobenzofuran-5-carboxylic acid (1.812 g, 5.57 mmol, 95% yield) as a cream solid.

LCMS (method Formic): Retention time 0.98, [M+H]$^+$= 326.3

EXAMPLES

Example 1: (+/−)-N$^5$-((1R,5S,6r)-3-oxabicyclo[3.1.0]hexan-6-yl)-N$^7$,3-dimethyl-3-phenyl-2,3-dihydrobenzofuran-5,7-dicarboxamide

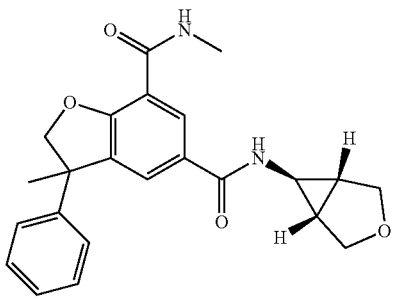 [SMILES: CNC(=O)c1cc(C(=O)N[C@H]2[C@@H]3COC[C@@H]32)cc2c1OCC2(C)c1ccccc1]

(+/−)-3-Methyl-7-(methylcarbamoyl)-3-phenyl-2,3-dihydrobenzofuran-5-carboxylic acid (60 mg, 0.19 mmol) and HATU (88 mg, 0.23 mmol) were dissolved in DCM (4 mL) at rt under N$_2$. DIPEA (0.101 mL, 0.578 mmol) was added and the resulting solution was stirred at rt for 10 min before (1R,5S,6r)-3-oxabicyclo[3.1.0]hexan-6-amine (22.9 mg, 0.231 mmol) was added. The resulting solution was stirred at rt for 1 h. The reaction was quenched with sat. NaHCO$_3$ (aq) and extracted with DCM. The organics were passed through a hydrophobic frit and concentrated in vacuo to afford the crude product which was purified by silica gel column chromatography eluting with a gradient of 0-100% (3:1 EtOAc/EtOH):cyclohexane and the appropriate fractions collected and concentrated in vacuo to afford (+/−)-N$^5$-((1R,5S,6r)-3-oxabicyclo[3.1.0]hexan-6-yl)-N$^7$,3-dimethyl-3-phenyl-2,3-dihydrobenzofuran-5,7-dicarboxamide (73 mg, 0.19 mmol, 97% yield) as a white solid.

LCMS (method formic): Retention time 0.90 min, [M+H]$^+$=393

$^1$H NMR (DMSO-d$_6$, 400 MHz): δ (ppm) 8.45 (d, J=3.9 Hz, 1H), 8.24 (d, J=2.0 Hz, 1H), 7.87 (d, J=4.4 Hz, 1H), 7.73 (d, J=2.0 Hz, 1H), 7.23-7.39 (m, 5H), 4.83 (d, J=9.0 Hz, 1H), 4.72 (d, J=9.0 Hz, 1H), 3.84 (d, J=8.3 Hz, 2H), 3.62 (dd, J=8.3, 2.2 Hz, 2H), 2.84 (d, J=4.6 Hz, 3H), 2.55-2.60 (m, 1H), 1.88 (q, J=2.2 Hz, 2H), 1.76 (s, 3H);

Examples 2 and 3: (S*)—N$^5$-((1R,5S,6r)-3-oxabicyclo[3.1.0]hexan-6-yl)-N$^7$,3-dimethyl-3-phenyl-2,3-dihydrobenzofuran-5,7-dicarboxamide compound and (R*)—N5-((1R,5S,6r)-3-oxabicyclo[3.1.0]hexan-6-yl)-N$^7$,3-dimethyl-3-phenyl-2,3-dihydrobenzofuran-5,7-dicarboxamide

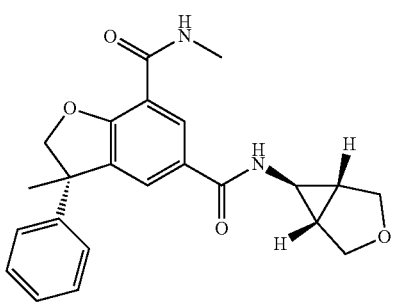

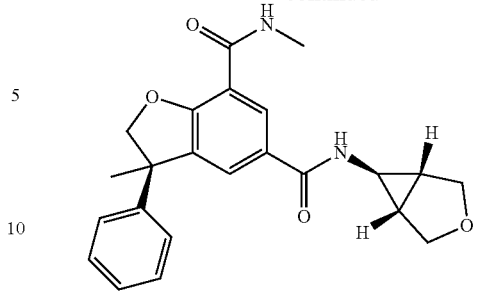

(+/−)-N$^5$-((1R,5S,6r)-3-oxabicyclo[3.1.0]hexan-6-yl)-N$^7$,3-dimethyl-3-phenyl-2,3-dihydrobenzofuran-5,7-dicarboxamide (42 mg) was submitted for chiral HPLC purification.

Analytical method: Approximatively 0.5 mg of material was dissolved in 50% EtOH:heptane (1 mL); 20 μL injected onto column. Elution: 15% EtOH in heptane, flow rate=1.0 mL/min, wavelength=215 nm. Column=Chiralpak OD-H 250×4.6 mm (5 micron).

Preparative method: Approximatively 41 mg of material was dissolved in EtOH (2 mL).

Injections: 1.0 mL of the solution was injected onto the column. Elution: 15% EtOH in heptane, flow rate=30 mL/min, wavelength=215 nm. Column=Chiralpak OD-H 250×30 mm (5 μm).

Fractions from 18-20 min were collected and concentrated to give (S*)—N$^5$-((1R,5S,6r)-3-oxabicyclo[3.1.0]hexan-6-yl)-N$^7$,3-dimethyl-3-phenyl-2,3-dihydrobenzofuran-5,7-dicarboxamide (16 mg, 0.041 mmol, yield=38%) and fractions from 22.5-28 min gave (R*)—N$^5$-((1R,5S,6r)-3-oxabicyclo[3.1.0]hexan-6-yl)-N$^7$,3-dimethyl-3-phenyl-2,3-dihydrobenzofuran-5,7-dicarboxamide (14 mg, 0.036 mmol, yield=33%)

LCMS (method Formic): Retention time 0.92 min, [M+H]$^+$=437 (Example 2)

$^1$H NMR (400 MHz, METHANOL-d$_4$) δ ppm 8.36 (d, J=2.0 Hz, 1H) 7.70 (d, J=2.0 Hz, 1H) 7.17-7.40 (m, 5H) 4.89 (d, J=8.8 Hz, 1H) 4.77 (d, J=9.0 Hz, 1H) 4.00 (d, J=8.3 Hz, 2H) 3.73 (d, J=8.3 Hz, 2H) 2.99 (s, 3H) 2.61 (t, J=2.4 Hz, 1H) 1.92 (t, J=2.7 Hz, 2H) 1.82 (s, 3H)

LCMS (method Formic): Retention time 0.92 min, [M+H]$^+$=437 (Example 3).

Example 4: (S*)—N$^5$,N$^7$,3-Trimethyl-3-phenyl-2,3-dihydrobenzofuran-5,7-dicarboxamide

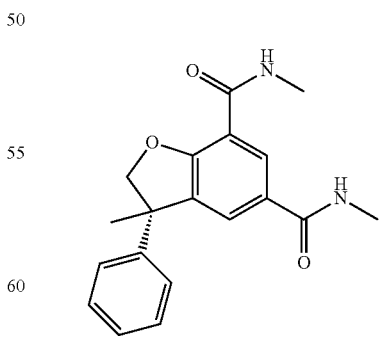

To a stock solution of (S*)-3-methyl-7-(methylcarbamoyl)-3-phenyl-2,3-dihydrobenzofuran-5-carboxylic acid (0.156 g, 0.500 mmol) and HATU (0.190 g, 0.500 mmol) in DMF (2.5 mL) was added DIPEA (0.26 mL, 1.5 mmol) and the solution was stirred for 5 min. An aliquot of this stock solution (0.55 mL) was dispensed into a vial containing methylamine (0.120 mmol) the vial was left to stand at rt for 18 h. The crude was purified directly using MDAP (Formic method) to give: (S*)—$N^5,N^7$,3-trimethyl-3-phenyl-2,3-dihydrobenzofuran-5,7-dicarboxamide (24 mg, 0.075 mmol, yield 67%)

LCMS (method formic): Retention time 0.86 min, [M+H]$^+$=325

Similarly prepared were the following:

| Ex. | Structure | Name | Retention time (method formic) | [M + H]+ |
|---|---|---|---|---|
| 5 | 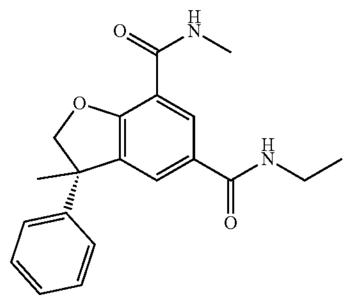 [SMILES: CCNC(=O)c1cc(C(=O)NC)c2c(c1)[C@](C)(c1ccccc1)CO2] | (S*)-$N^5$-Ethyl-$N^7$,3-dimethyl-3-phenyl-2,3-dihydrobenzofuran-5,7-dicarboxamide (25 mg, 0.072 mmol, yield 65%) | 0.92 | 339 |
| 6 | 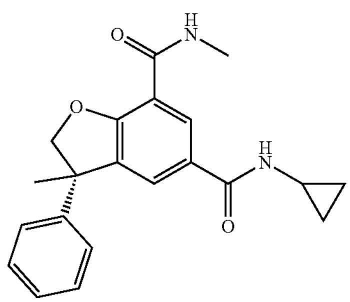 [SMILES: CNC(=O)c1cc(C(=O)NC2CC2)cc2c1OC[C@@]2(C)c1ccccc1] | (S*)-$N^5$-Cyclopropyl-$N^7$,3-dimethyl-3-phenyl-2,3-dihydrobenzofuran-5,7-dicarboxamide (32 mg, 0.092 mmol, yield = 82%) | 0.94 | 351 |
| 7 | 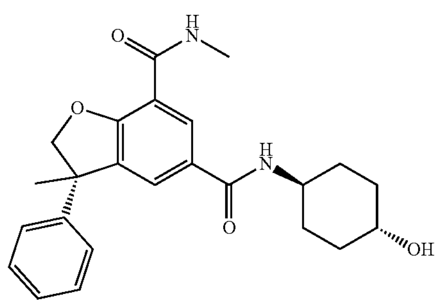 | (S*)-$N^5$-((1r,4S)-4-Hydroxycyclohexyl)-$N^7$,3-dimethyl-3-phenyl-2,3-dihydrobenzofuran-5,7-dicarboxamide (41 mg, 0.10 mmol, yield = 90%) | 0.87 | 409 |
| 8 | 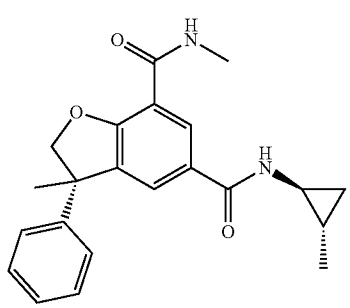 [SMILES: CNC(=O)c1cc(C(=O)N[C@H]2C[C@@H]2C)cc2c1OC[C@@]2(C)c1ccccc1] | (S*)-$N^7$,3-Dimethyl-$N^5$-((1S,2S)-2-methylcyclopropyl)-3-phenyl-2,3-dihydrobenzofuran-5,7-dicarboxamide (24 mg, 0.067 mmol, yield = 60%) | 1.02 | 365 |

Examples 9 and 10: (S*)—N⁵-((1R,3R,5S,6r)-3-hydroxybicyclo[3.1.0]hexan-6-yl)-N⁷,3-dimethyl-3-phenyl-2,3-dihydrobenzofuran-5,7-dicarboxamide and (S*)—N⁵-((1R,3S,5S,6r)-3-hydroxybicyclo[3.1.0]hexan-6-yl)-N⁷,3-dimethyl-3-phenyl-2,3-dihydrobenzofuran-5,7-dicarboxamide

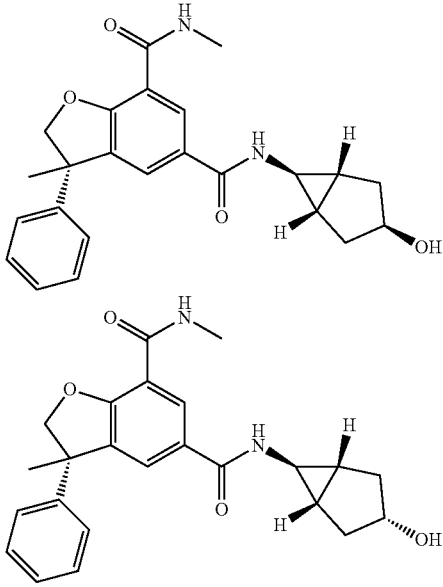

(S*)-3-Methyl-7-(methylcarbamoyl)-3-phenyl-2,3-dihydrobenzofuran-5-carboxylic acid (80 mg, 0.26 mmol), HATU (147 mg, 0.385 mmol), DMF (1.5 mL) and DIPEA (0.135 mL, 0.771 mmol) were stirred for 5 min, then (1R,5S,6r)-6-aminobicyclo[3.1.0]hexan-3-ol (32.0 mg, 0.283 mmol) was added and the reaction was stirred for 1 h at rt. Further (S*)-3-methyl-7-(methylcarbamoyl)-3-phenyl-2,3-dihydrobenzofuran-5-carboxylic acid (40 mg, 0.13 mmol), HATU (147 mg, 0.385 mmol) and DIPEA (0.135 mL, 0.771 mmol) were added and the reaction stirred at rt for 1 h. The reaction was concentrated in vacuo and purified by MDAP (method high pH) to give (S*)—N⁵-((1R,3R,5S,6r)-3-hydroxybicyclo[3.1.0]hexan-6-yl)-N⁷,3-dimethyl-3-phenyl-2,3-dihydrobenzofuran-5,7-dicarboxamide (16 mg, 0.039 mmol, 15% yield) as a white solid LCMS (method Formic): Retention time 0.88 min, [M+H]⁺=407

¹H NMR (400 MHz, DMSO-d₆) δ ppm 8.30 (d, J=3.8 Hz, 1H) 8.21 (d, J=2.0 Hz, 1H) 7.87 (d, J=4.5 Hz, 1H) 7.72 (d, J=1.8 Hz, 1H) 7.19-7.42 (m, 5H) 4.84 (d, J=9.0 Hz, 1H) 4.72 (d, J=9.0 Hz, 1H) 4.57 (d, J=5.3 Hz, 1H) 3.77-3.91 (m, 1H) 2.85 (d, J=4.8 Hz, 3H) 2.04 (dd, J=12.5, 7.0 Hz, 2H) 1.77 (s, 3H) 1.61 (ddd, J=12.4, 8.0, 4.5 Hz, 2H) 1.37-1.49 (m, 2H) and (S*)—N⁵-((1R,3S,5S,6r)-3-hydroxybicyclo[3.1.0]hexan-6-yl)-N⁷,3-dimethyl-3-phenyl-2,3-dihydrobenzofuran-5,7-dicarboxamide (36 mg, 0.089 mmol, 35% yield) as a white solid LCMS (method Formic): Retention time 0.92 min, [M+H]⁺=407

Example 11: (S*)—N⁵-(3-((2r,5S)-5-amino-1,3-dioxan-2-yl)propyl)-N⁷,3-dimethyl-3-phenyl-2,3-dihydrobenzofuran-5,7-dicarboxamide

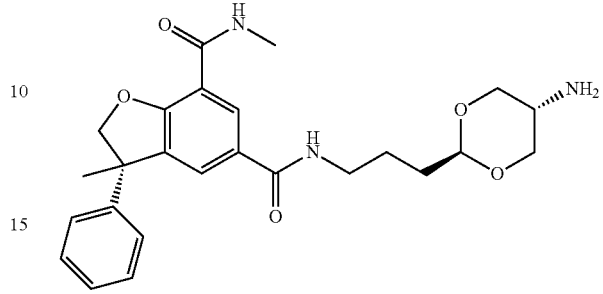

To a suspension of (S*)—N⁵-(3-((2r,5S)-5-(1,3-dioxoisoindolin-2-yl)-1,3-dioxan-2-yl)propyl)-N⁷,3-dimethyl-3-phenyl-2,3-dihydrobenzofuran-5,7-dicarboxamide (59 mg, 0.10 mmol) in EtOH (1 mL) was added hydrazine hydrate (0.015 mL, 0.30 mmol); the resulting suspension was stirred at 40° C. for 2.5 h. The reaction mixture was diluted with MeOH and sonicated, it was then filtered and the solid washed with MeOH. The filtrate was evaporated under a positive pressure of N₂ to give a white solid. This solid was purified by MDAP (Method high pH) and was further purified using silica gel column chromatography eluting with a gradient of 0-50% (20% (2M NH₃ in MeOH) in DCM):DCM. The appropriate fractions were collected and concentrated in vacuo to give the crude title compound which was further purified using silica gel column chromatography eluting with a gradient of 20-60% (20% (2M NH₃ in MeOH)DCM):DCM. The appropriate fractions were collected and concentrated in vacuo to afford (S*)—N⁵-(3-((2r,5S)-5-amino-1,3-dioxan-2-yl)propyl)-N⁷,3-dimethyl-3-phenyl-2,3-dihydrobenzofuran-5,7-dicarboxamide (24 mg, 0.053 mmol, 52% yield) as a colourless oil.

LCMS (method formic): Retention time 0.62 min, [M+H]⁺=454

Example 12: (S*)—N⁵-(2-((2r,5S)-5-amino-1,3-dioxan-2-yl)ethyl)-N⁷,3-dimethyl-3-phenyl-2,3-dihydrobenzofuran-5,7-dicarboxamide

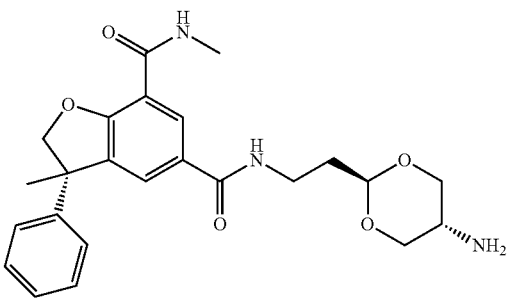 [SMILES: CNC(=O)c1cc(C(=O)NCC[C@H]2OC[C@H](N)CO2)cc2c1OC[C@@]2(C)c1ccccc1]

To a suspension of (S*)—N⁵-(2-((2r,5S)-5-(1,3-dioxoisoindolin-2-yl)-1,3-dioxan-2-yl)ethyl)-N⁷,3-dimethyl-3-phenyl-2,3-dihydrobenzofuran-5,7-dicarboxamide (135 mg, 0.237 mmol) in EtOH (1 mL) was added hydrazine hydrate (0.034 mL, 0.71 mmol); the resulting suspension was stirred at 40° C. for 2 h and then allowed to stand for 1 h. The reaction mixture was diluted with MeOH, transferred to a scintillation vial as a suspension with the aid of sonication and evaporated under a positive pressure of $N_2$ to give a white solid. This solid was purified using silica gel column chromatography eluting with a gradient of 20-60% (20% (2M $NH_3$ in MeOH) in DCM):DCM. The appropriate fractions were collected and concentrated in vacuo to afford (S*)—$N^5$-(2-((2r,5S)-5-amino-1,3-dioxan-2-yl)ethyl)-$N^7$,3-dimethyl-3-phenyl-2,3-dihydrobenzofuran-5,7-dicarboxamide (87 mg, 0.20 mmol, 84% yield) as a white solid.

LCMS (method formic): Retention time 0.58 min, $[M+H]^+$=440

Example 13: (+/−)-$N^5$-((1R,5S,6r)-3-Oxabicyclo [3.1.0]hexan-6-yl)-3-(hydroxymethyl)-$N^7$-methyl-3-phenyl-2,3-dihydrobenzofuran-5,7-dicarboxamide

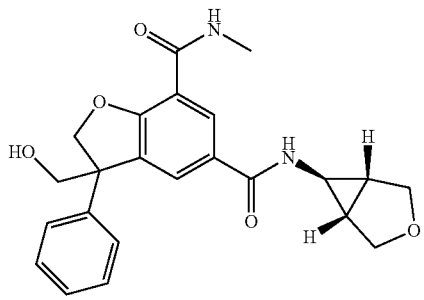 [SMILES: CNC(=O)c1cc(C(=O)N[C@H]2[C@@H]3COC[C@@H]32)cc2c1OCC2(CO)c1ccccc1]

(+/−)-3-(Hydroxymethyl)-7-(methylcarbamoyl)-3-phenyl-2,3-dihydrobenzofuran-5-carboxylic acid (14 mg, 0.043 mmol) and HATU (19.5 mg, 0.0510 mmol) were dissolved in DCM (4 mL) at rt under $N_2$. DIPEA (0.022 mL, 0.13 mmol) was added and the resulting solution was stirred at rt for 10 min before (1R,5S,6r)-3-oxabicyclo[3.1.0]hexan-6-amine (5.1 mg, 0.051 mmol) was added. The resulting solution was stirred at rt for 1 h. The reaction was quenched with sat. $NaHCO_3$(aq) and extracted with DCM. The combined organics were passed through a hydrophobic frit and concentrated in vacuo to afford the crude product which was purified by MDAP (method Formic) to afford (+/−)-$N^5$-((1R,5S,6r)-3-oxabicyclo[3.1.0]hexan-6-yl)-3-(hydroxymethyl)-$N^7$-methyl-3-phenyl-2,3-dihydrobenzofuran-5,7-dicarboxamide (8.4 mg, 0.021 mmol, 48% yield) as a white solid.

LCMS (method formic): Retention time 0.77 min, $[M+H]^+$=409

Examples 14 and 15: (S*)—$N^5$-((1R,5S,6r)-3-oxabicyclo[3.1.0]hexan-6-yl)-3-(hydroxymethyl)-$N^7$-methyl-3-phenyl-2,3-dihydrobenzofuran-5,7-dicarboxamide and (R*)—$N^5$-((1R,5S,6r)-3-oxabicyclo [3.1.0]hexan-6-yl)-3-(hydroxymethyl)-$N^7$-methyl-3-phenyl-2,3-dihydrobenzofuran-5,7-dicarboxamide

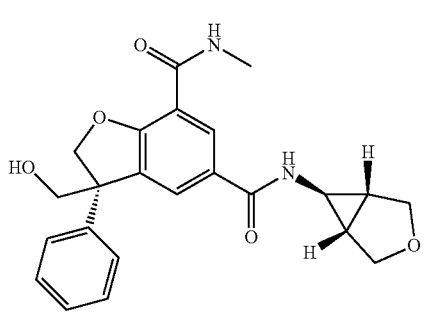

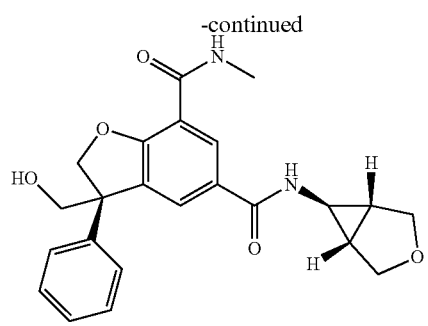

(+/−)-$N^5$-((1R,5S,6r)-3-Oxabicyclo[3.1.0]hexan-6-yl)-3-(hydroxymethyl)-$N^7$-methyl-3-phenyl-2,3-dihydrobenzofuran-5,7-dicarboxamide (70 mg) was submitted for chiral HPLC purification.

Analytical method: Approximatively 0.5 mg of material was dissolved in 50% EtOH:heptane (1 mL); 20 µL injected on column. Elution: 40% EtOH (+0.2% isopropylamine) in heptane, flow rate=1.0 mL/min, wavelength=215 nm. Column=Chiralpak IC 250×4.6 mm (5 micron).

Preparative method: Approximatively 70 mg of material was dissolved in EtOH (2 mL). Injections: 2.0 mL of the solution was injected onto the column. Elution: 20% EtOH (+0.2% isopropylamine) in heptane (+0.2% isopropylamine), flow rate=30 mL/min, wavelength=215 nm. Column=Chiralpak IC 250×30 mm (5 um).

Fractions from 38-44 min were collected and concentrated to give (S*)—$N^5$-((1R,5S,6r)-3-oxabicyclo[3.1.0] hexan-6-yl)-3-(hydroxymethyl)-$N^7$-methyl-3-phenyl-2,3-dihydrobenzofuran-5,7-dicarboxamide (25 mg, 0.061 mmol, yield 37%) Fractions from 48-60 min were collected and concentrated to give (R*)—$N^5$-((1R,5S,6r)-3-oxabicyclo [3.1.0]hexan-6-yl)-3-(hydroxymethyl)-$N^7$-methyl-3-phenyl-2,3-dihydrobenzofuran-5,7-dicarboxamide (22 mg, 0.054 mmol, yield=31%)

LCMS (method Formic): Retention time 0.77 min, $[M+H]^+$=409 (Example 14)

LCMS (method Formic): Retention time 0.77 min, $[M+H]^+$=409 (Example 15).

Examples 16 and 17: (S*)—$N^5$-((1R,3R,5S,6r)-3-hydroxybicyclo[3.1.0]hexan-6-yl)-3-(hydroxymethyl)-$N^7$-methyl-3-phenyl-2,3-dihydrobenzofuran-5,7-dicarboxamide and (S*)—$N^5$-((1R,3S,5S,6r)-3-hydroxybicyclo[3.1.0]hexan-6-yl)-3-(hydroxymethyl)-$N^7$-methyl-3-phenyl-2,3-dihydrobenzofuran-5,7-

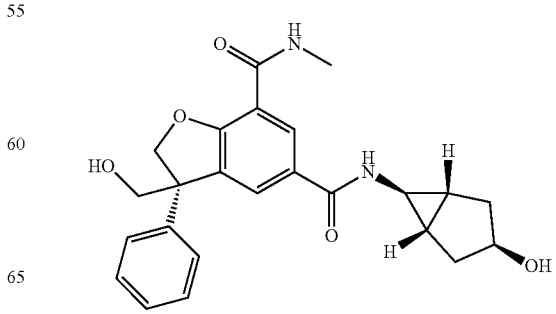

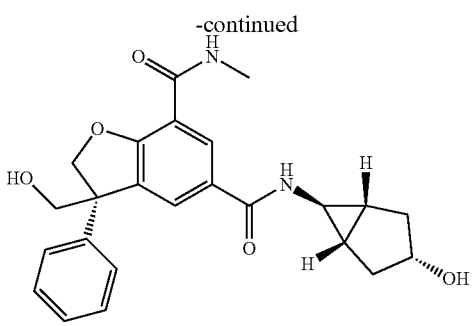

(S*)-3-(Hydroxymethyl)-7-(methylcarbamoyl)-3-phenyl-2,3-dihydrobenzofuran-5-carboxylic acid (90 mg, 0.27 mmol), HATU (115 mg, 0.302 mmol) and DIPEA (0.144 mL, 0.825 mmol) were stirred in DMF (4 mL) at rt for 5 min. (1R,5S,6r)-6-aminobicyclo[3.1.0]hexan-3-ol (37.3 mg, 0.330 mmol) was added and the reaction was stirred at rt for 2 h. The reaction was diluted with EtOAc and was washed with 10% citric acid (aq) followed by 10% LiCl (aq). The organic phase was dried using a hydrophobic frit and concentrated to give a yellow solid. This solid was purified by MDAP (Method High pH) to give: (S*)—N$^5$-((1R,3R,5S,6r)-3-hydroxybicyclo[3.1.0]hexan-6-yl)-3-(hydroxymethyl)-N$^7$-methyl-3-phenyl-2,3-dihydrobenzofuran-5,7-dicarboxamide (22 mg, 0.052 mmol, 19% yield) as a white solid LCMS (method Formic): Retention time 0.75 min, [M+H]$^+$=423

(S*)—N$^5$-((1R,3S,5S,6r)-3-hydroxybicyclo[3.1.0]hexan-6-yl)-3-(hydroxymethyl)-N$^7$-methyl-3-phenyl-2,3-dihydrobenzofuran-5,7-dicarboxamide (23 mg, 0.054 mmol, 20% yield) as a white solid LCMS (method Formic): Retention time 0.79 min, [M+H]$^+$=423

Example 18: (+/−)-3-(Hydroxymethyl)-N$^7$-methyl-N$^5$-((1S,2S)-2-methylcyclopropyl)-3-phenyl-2,3-dihydrobenzofuran-5,7-dicarboxamide

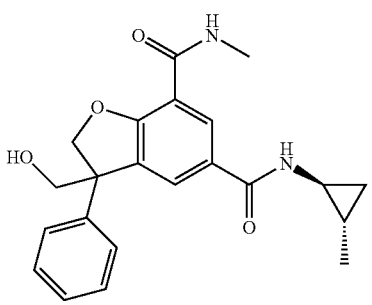 [SMILES: CNC(=O)c1cc(C(=O)N[C@H]2C[C@@H]2C)cc2c1OCC2(CO)c1ccccc1]

(+/−)-3-(Hydroxymethyl)-7-(methylcarbamoyl)-3-phenyl-2,3-dihydrobenzofuran-5-carboxylic acid (90 mg, 0.275 mmol) was suspended in DMF (3 mL) and treated with HATU (115 mg, 0.302 mmol) and DIPEA (0.144 mL, 0.825 mmol) and was stirred at rt for 10 min, (1S,2S)-2-methylcyclopropan-1-amine hydrochloride (35.5 mg, 0.330 mmol) was added and the reaction stirred at rt for 2 h. The reaction was diluted with 10% citric acid (aq) and extracted with EtOAc, the organic phase was washed with 10% LiCl (aq) dried using a hydrophobic frit and concentrated to give a yellow oil. This oil was purified using silica gel column chromatography eluting with a gradient of 0-10% 2M NH$_3$ in MeOH:DCM to give (+/−)-3-(hydroxymethyl)-N$^7$-methyl-N$^5$-((1S,2S)-2-methylcyclopropyl)-3-phenyl-2,3-dihydrobenzofuran-5,7-dicarboxamide (77 mg, 0.20 mmol, 74% yield) as a yellow solid.

LCMS (method formic): Retention time 0.88 min, [M+H]$^+$=381

Example 19: (S*)-3-(Hydroxymethyl)-N$^5$,N$^7$-dimethyl-3-phenyl-2,3-dihydrobenzofuran-5,7-dicarboxamide

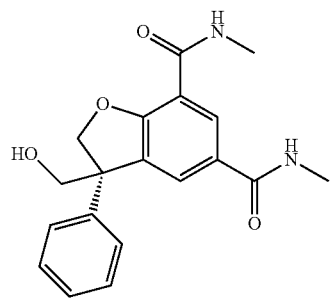 [SMILES: CNC(=O)c1cc(C(=O)NC)c2c(c1)[C@](CO)(c1ccccc1)CO2]

A stock solution of (S*)-3-(hydroxymethyl)-7-(methylcarbamoyl)-3-phenyl-2,3-dihydrobenzofuran-5-carboxylic acid (0.164 g, 0.500 mmol) and HATU (0.190 g, 0.500 mmol) in DMF (2.5 mL) was prepared. To this solution was added DIPEA (0.260 mL, 1.500 mmol). An aliquot (0.55 mL) of this stock solution was added to a vial containing (0.004 mg, 0.120 mmol) the vial was shaken and then left to stand at rt for 18 h. The reaction was purified directly by MDAP (Method Formic) to give (S*)-3-(hydroxymethyl)-N$^5$,N$^7$-dimethyl-3-phenyl-2,3-dihydrobenzofuran-5,7-dicarboxamide (26 mg, 0.076 mmol, 68% yield)

LCMS (method formic): Retention time 0.72 min, [M+H]$^+$=341

Similarly prepared were the following:

| Ex. | Structure | Name | Retention time (method formic) | [M + H]+ |
|---|---|---|---|---|
| 20 | 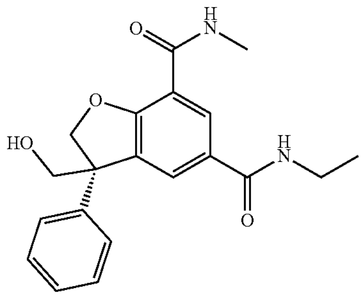 [SMILES: CCNC(=O)c1cc(C(=O)NC)c2c(c1)[C@](CO)(c1ccccc1)CO2] | (S*)-$N^5$-Ethyl-3-(hydroxymethyl)-$N^7$-methyl-3-phenyl-2,3-dihydrobenzofuran-5,7-dicarboxamide (24 mg, 0.067 mmol, yield 68%) | 0.77 | 355 |
| 21 | 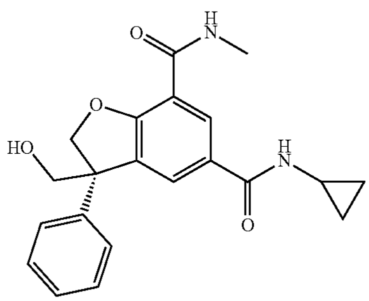 [SMILES: CNC(=O)c1cc(C(=O)NC2CC2)cc2c1OC[C@@]2(CO)c1ccccc1] | (S*)-$N^5$-Cyclopropyl-3-(hydroxymethyl)-$N^7$-methyl-3-phenyl-2,3-dihydrobenzofuran-5,7-dicarboxamide (23 mg, 0.063 mmol, yield = 57%) | 0.78 | 367 |
| 22 | 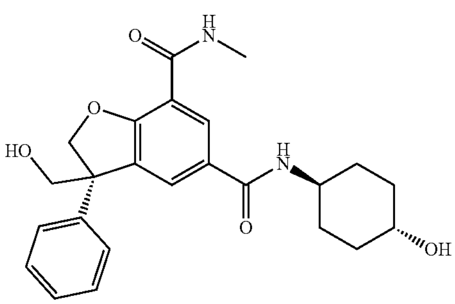 [SMILES: CNC(=O)c1cc(C(=O)N[C@H]2CC[C@H](O)CC2)cc2c1OC[C@@]2(CO)c1ccccc1] | (S*)-$N^5$-((1r,4S)-4-Hydroxycyclohexyl)-3-(hydroxymethyl)-$N^7$-methyl-3-phenyl-2,3-dihydrobenzofuran-5,7-dicarboxamide (30 mg, 0.70 mmol, yield = 63%) | 0.73 | 425 |
| 23 | 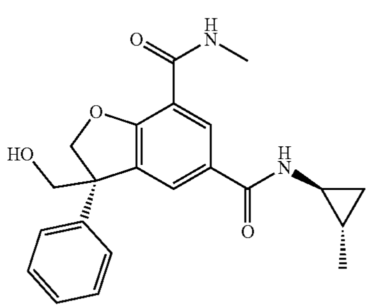 [SMILES: CNC(=O)c1cc(C(=O)N[C@H]2C[C@@H]2C)cc2c1OC[C@@]2(CO)c1ccccc1] | (S*)-3-(Hydroxymethyl)-$N^7$-methyl-$N^5$-((1S,2S)-2-methylcyclopropyl)-3-phenyl-2,3-dihydrobenzofuran-5,7-dicarboxamide (24 mg, 0.063 mmol, yield = 57%) $^1$H NMR (600 MHz, DMSO-d6) δ ppm 8.40 (d, J = 4.0 Hz, 1 H) 8.23 (d, J = 1.8 Hz, 1 H) 7.84 (d, J = 4.4 Hz, 1 H) 7.80 (d, J = 1.8 Hz, 1 H) 7.22-7.38 (m, 5 H) 5.00 (d, J = 9.2 Hz, 1 H) 4.81 (d, J = 9.2 Hz, 1 H) 3.92-4.03 (m, 2 H) 2.83 (d, J = 4.8 Hz, 3 H) 2.53 (d, J = 3.7 Hz, 1 H) 1.05 (d, J = 6.2 Hz, 3 H) 0.90-0.97 (m, 1 H) 0.73 (dt, J = 8.7, 4.6 Hz, 1 H) 0.46 (dt, J = 7.2, 5.4 Hz, 1 H) | 0.86 | 381 |

Example 24: (S*)—$N^5$-((1R,5S,6r)-3-Oxabicyclo[3.1.0]hexan-6-yl)-3-ethyl-N7-methyl-3-phenyl-2,3-dihydrobenzofuran-5,7-dicarboxamide

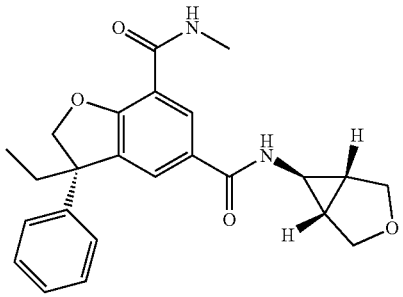 [SMILES: CC[C@@]1(c2ccccc2)COc2c(C(=O)NC)cc(C(=O)N[C@H]3[C@@H]4COC[C@@H]43)cc21]

(S*)-3-Ethyl-7-(methylcarbamoyl)-3-phenyl-2,3-dihydrobenzofuran-5-carboxylic acid (76 mg, 0.23 mmol) was taken up in DMF (2 mL). DIPEA (0.122 mL, 0.701 mmol), then (1R,5S,6r)-3-oxabicyclo[3.1.0]hexan-6-amine HCl (38.0 mg, 0.280 mmol) was added and the reaction left to stir for 5 min. HATU (135 mg, 0.355 mmol) was added, and the reaction was left to stir at rt for 1.75 h. The reaction was concentrated in vacuo. The residue was partitioned between sat. $NaHCO_3$(aq) and EtOAc. The organic layer was washed with 1 M HCl (aq) and brine, dried with $Na_2SO_4$, filtered and concentrated in vacuo to yield a brown solid. The crude product was purified using silica gel column chromatography eluting with a gradient of 5-50% EtOAc:cyclohexane and the appropriate fractions collected and concentrated in vacuo to yield (S*)—$N^5$-((1R,5S,6r)-3-oxabicyclo[3.1.0]hexan-6-yl)-3-ethyl-$N^7$-methyl-3-phenyl-2,3-dihydrobenzofuran-5,7-dicarboxamide (96.4 mg, 0.225 mmol, 96% yield, purity=95%) as a white solid.

LCMS (method formic): Retention time 0.95 min, $[M+H]^+$=407

Similarly prepared were the following:

| Ex. | Structure | Name | Retention time (method formic) | [M + H]+ |
|---|---|---|---|---|
| 25 | 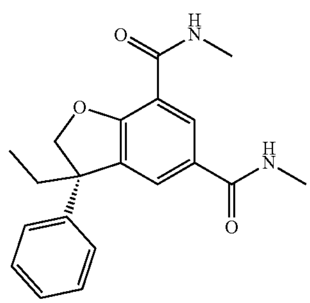 [SMILES: CC[C@@]1(c2ccccc2)COc2c(C(=O)NC)cc(C(=O)NC)cc21] | (S*)-3-Ethyl-$N^5$,$N^7$-dimethyl-3-phenyl-2,3-dihydrobenzofuran-5,7-dicarboxamide (19 mg, 0.056 mmol, yield 61%) | 0.92 | 339 |
| 26 | 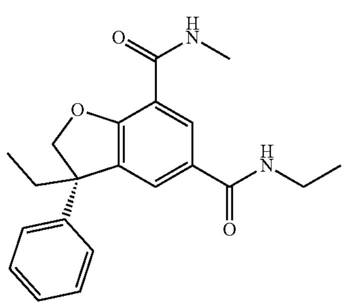 [SMILES: CCNC(=O)c1cc(C(=O)NC)c2c(c1)[C@](CC)(c1ccccc1)CO2] | (S*)-$N^5$,3-diethyl-$N^7$-methyl-3-phenyl-2,3-dihydrobenzofuran-5,7-dicarboxamide (29 mg, 0.082 mmol, yield = 59%) | 0.99 | 353 |
| 27 | 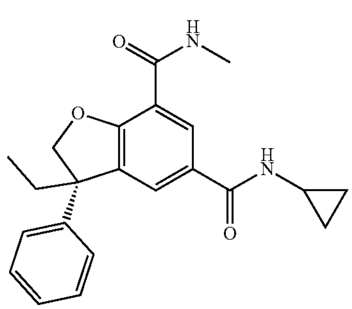 [SMILES: CC[C@@]1(c2ccccc2)COc2c(C(=O)NC)cc(C(=O)NC3CC3)cc21] | (S*)-$N^5$-Cyclopropyl-3-ethyl-$N^7$-methyl-3-phenyl-2,3-dihydrobenzofuran-5,7-dicarboxamide (29 mg, 0.079 mmol, yield = 86%) | 0.99 | 365 |

| Ex. | Structure | Name | Retention time (method formic) | [M + H]+ |
|---|---|---|---|---|
| 28 | 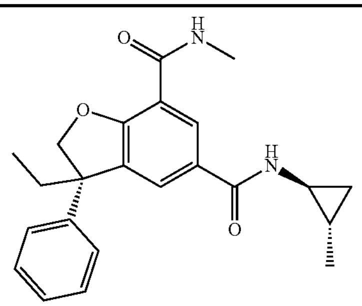 | (S*)-3-Ethyl-N$^7$-methyl-N$^5$-((1S,2S)-2-methylcyclopropyl)-3-phenyl-2,3-dihydrobenzofuran-5,7-dicarboxamide (30 mg, 0.079 mmol, yield = 86%) | 1.06 | 379 |
| 29 | 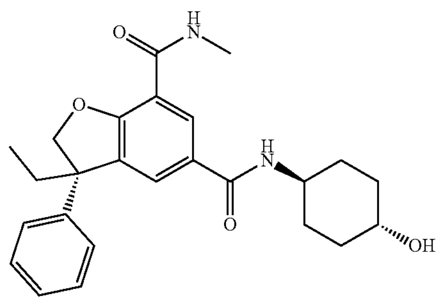 [SMILES: CC[C@@]1(c2ccccc2)COc2c(C(=O)NC)cc(C(=O)N[C@H]3CC[C@H](O)CC3)cc21] | (S*)-3-Ethyl-N$^5$-((1r,4S)-4-hydroxycyclohexyl)-N$^7$-methyl-3-phenyl-2,3-dihydrobenzofuran-5,7-dicarboxamide (42 mg, 0.089 mmol, yield = 98% | 0.96 (HpH) | 423 |

Example 30: (S*)-3-Ethyl-N$^5$-((1R,3R,5S,6r)-3-hydroxybicyclo[3.1.0]hexan-6-yl)-N$^7$-methyl-3-phenyl-2,3-dihydrobenzofuran-5,7-dicarboxamide

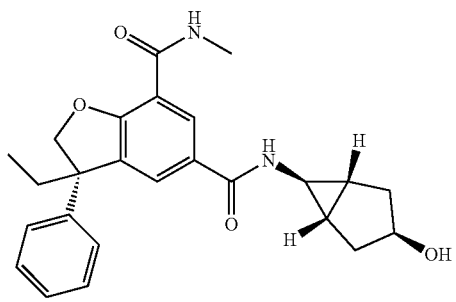 [SMILES: CC[C@@]1(c2ccccc2)COc2c(C(=O)NC)cc(C(=O)N[C@H]3[C@@H]4C[C@@H](O)C[C@@H]43)cc21]

(S*)-3-Ethyl-7-(methylcarbamoyl)-3-phenyl-2,3-dihydrobenzofuran-5-carboxylic acid (60 mg, 0.18 mmol) and HATU (84 mg, 0.22 mmol) were dissolved in DCM (4 mL) at rt. DIPEA (0.097 mL, 0.55 mmol) was added and the resulting solution was stirred at rt for 10 min before (1R,3S,5S,6r)-6-aminobicyclo[3.1.0]hexan-3-ol (25.0 mg, 0.221 mmol) was added. The resulting solution was stirred at rt for 1 h. The reaction was quenched with sat. NaHCO$_3$(aq) and extracted with DCM. The combined organics were passed through a hydrophobic frit and concentrated in vacuo to afford the crude product. The crude product was purified by MDAP (formic method) to (S*)-3-ethyl-N$^5$-((1R,3R,5S,6r)-3-hydroxybicyclo[3.1.0]hexan-6-yl)-N$^7$-methyl-3-phenyl-2,3-dihydrobenzofuran-5,7-dicarboxamide (42.4 mg, 0.101 mmol, 55% yield) as a white solid.

LCMS (method formic): Retention time 0.92 min, [M+H]$^+$=421

Example 31: (S*)—N$^5$-(2-((2r,5S)-5-amino-1,3-dioxan-2-yl)ethyl)-3-ethyl-N$^7$-methyl-3-phenyl-2,3-dihydrobenzofuran-5,7-dicarboxamide

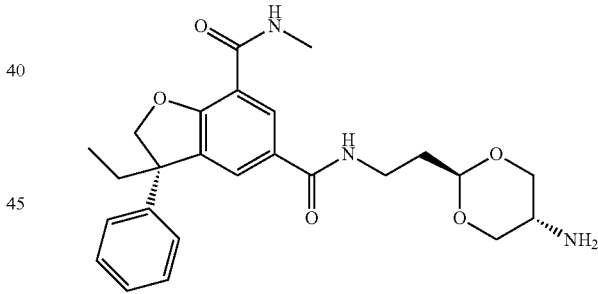

To a suspension of (S*)—N$^5$-(2-((2r,5S)-5-(1,3-dioxoisoindolin-2-yl)-1,3-dioxan-2-yl)ethyl)-3-ethyl-N$^7$-methyl-3-phenyl-2,3-dihydrobenzofuran-5,7-dicarboxamide (105 mg, 0.180 mmol) in EtOH (1 mL) was added hydrazine hydrate (0.026 mL, 0.54 mmol); the resulting suspension was stirred at 40° C. for 2 h and then allowed to stand overnight. The reaction mixture was diluted with EtOH, transferred to a scintillation vial as a suspension with the aid of sonication and evaporated under a positive pressure of N$_2$ to give a white solid. This solid was purified using silica gel column chromatography eluting with a gradient of 0-60% (20% (2M NH$_3$ in MeOH)DCM):DCM. and the appropriate fractions collected and concentrated in vacuo to give (S*)—N$^5$-(2-((2r,5S)-5-amino-1,3-dioxan-2-yl)ethyl)-3-ethyl-N$^7$-methyl-3-phenyl-2,3-dihydrobenzofuran-5,7-dicarboxamide (72 mg, 0.16 mmol, 88% yield)

LCMS (method formic): Retention time 0.91 min, [M+H]$^+$=454

Example 32: (S*)—N⁵-(3-((2r,5S)-5-Amino-1,3-dioxan-2-yl)propyl)-3-ethyl-N⁷-methyl-3-phenyl-2,3-dihydrobenzofuran-5,7-dicarboxamide

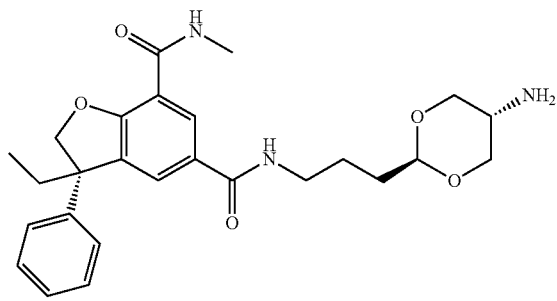 [SMILES: CC[C@@]1(c2ccccc2)COc2c(C(=O)NC)cc(C(=O)NCCC[C@H]3OC[C@H](N)CO3)cc21]

To a suspension of (S*)—N⁵-(3-((2r,5S)-5-(1,3-dioxoisoindolin-2-yl)-1,3-dioxan-2-yl)propyl)-3-ethyl-N⁷-methyl-3-phenyl-2,3-dihydrobenzofuran-5,7-dicarboxamide (80 mg, 0.13 mmol) in EtOH (1 mL) was added hydrazine hydrate (0.019 mL, 0.40 mmol); the resulting suspension was stirred at 40° C. for 2.5 h and then allowed to stand at rt overnight. The reaction mixture was diluted with EtOH and sonicated, and transferred to a scintillation vial, which was evaporated under a positive pressure of N₂ to give a white solid. This solid was purified using silica gel column chromatography eluting with a gradient of 0-60% (20% (2M NH₃ in MeOH)DCM):DCM. and the appropriate fractions collected and concentrated in vacuo to give (S*)—N⁵-(3-((2r,5S)-5-amino-1,3-dioxan-2-yl)propyl)-3-ethyl-N⁷-methyl-3-phenyl-2,3-dihydrobenzofuran-5,7-dicarboxamide (40 mg, 0.086 mmol, 64% yield) as a colourless gum.

LCMS (method formic): Retention time 0.92 min, [M+H]⁺=468

Example 33: (+/−) 3-ethyl-N⁵-(3-hydroxypropyl)-N⁷-methyl-3-phenyl-2,3-dihydrobenzofuran-5,7-dicarboxamide

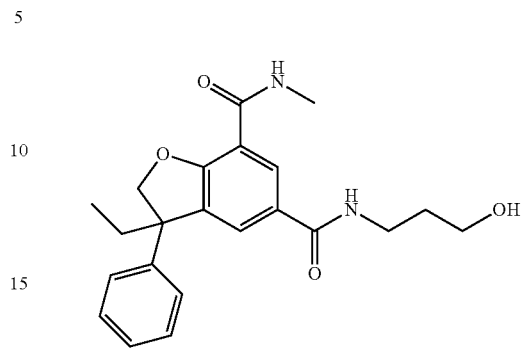

A solution of HATU (0.038 g, 0.100 mmol) dissolved in DMF (0.5 mL) and (+/−) 3-ethyl-7-(methylcarbamoyl)-3-phenyl-2,3-dihydrobenzofuran-5-carboxylic acid (0.032 g, 0.100 mmol, Intermediate 42) and DIPEA (0.052 mL, 0.300 mmol) was shaken and was then added to amino propanol (0.009 g, 0.120 mmol). The reaction was stood at rt for 64 h. The reaction was injected as is and purified by MDAP (High pH) to give: (+/−) 3-ethyl-N⁵-(3-hydroxpropyl)-N⁷-methyl-3-phenyl-2,3-dihydrobenzofuran-5,7-dicarboxamide (7.3 mg, 0.019 mmol, Yield 17%)

LCMS (method formic): Retention time 0.87 min, [M+H]⁺=383

Similarly prepared were the following:

| Ex. | Structure | Name | Retention time (method formic) | [M + H]+ |
|---|---|---|---|---|
| 34 | 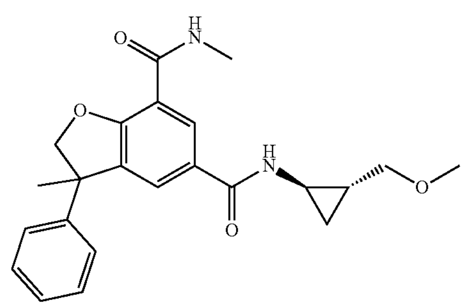 [SMILES: CNC(=O)c1cc(C(=O)N[C@@H]2C[C@H]2COC)cc2c1OCC2(C)c1ccccc1] | (+/−) N⁵-((1R,2R)-2-(methoxymethyl)cyclopropyl)-N⁷,3-dimethyl-3-phenyl-2,3-dihydrobenzofuran-5,7-dicarboxamide (10 mg, 0.026 mmol, yield 24%) | 0.93 | 395 |
| 35 | 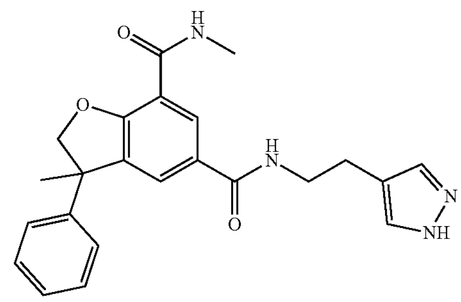 [SMILES: CNC(=O)c1cc(C(=O)NCCc2cn[nH]c2)cc2c1OCC2(C)c1ccccc1] | (+/−) N⁵-(2-(1H-pyrazol-4-yl)ethyl)-N⁷,3-dimethyl-3-phenyl-2,3-dihydrobenzofuran-5,7-dicarboxamide (12 mg, 0.030 mmol, yield = 27%) | 0.84 | 405 |

-continued

| Ex. | Structure | Name | Retention time (method formic) | [M + H]+ |
|---|---|---|---|---|
| 36 | 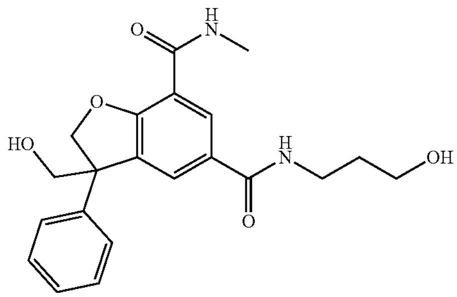 [SMILES: CNC(=O)c1cc(C(=O)NCCCO)cc2c1OCC2(CO)c1ccccc1] | (+/−) 3-(hydroxymethyl)-N$^5$-(3-hydroxpropyl)-N$^7$-methyl-3-phenyl-2,3-dihydrobenzofuran-5,7-dicarboxamide (11 mg, 0.029 mmol, yield = 27%) | 0.68 | 385 |
| 37 | 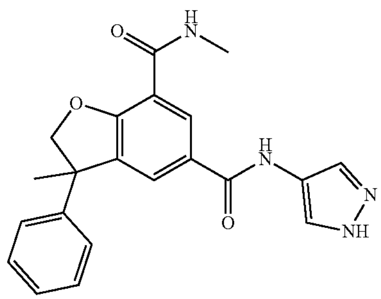 [SMILES: CNC(=O)c1cc(C(=O)Nc2cn[nH]c2)cc2c1OCC2(C)c1ccccc1] | (+/−) N$^7$,3-dimethyl-3-phenyl-N$^5$-(1H-pyrazol-4-yl)-2,3-dihydrobenzofuran-5,7-dicarboxamide (21 mg, 0.055 mmol, yield = 50%) | 0.85 | 377 |
| 38 | 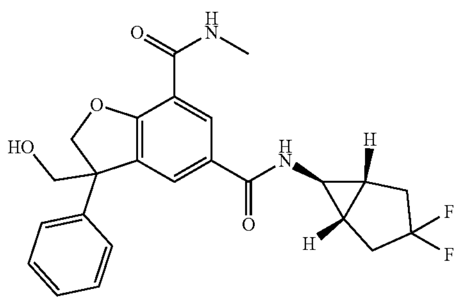 [SMILES: CNC(=O)c1cc(C(=O)N[C@H]2[C@@H]3CC(F)(F)C[C@@H]32)cc2c1OCC2(CO)c1ccccc1] | (+/−) N$^5$-((1R,5S,6r)-3,3-difluorobicyclo[3.1.0]hexan-6-yl)-3-(hydroxymethyl)-N$^7$-methyl-3-phenyl-2,3-dihydrobenzofuran-5,7-dicarboxamide (16 mg, 0.036 mmol, yield = 32%) | 0.91 | 443 |
| 39 | 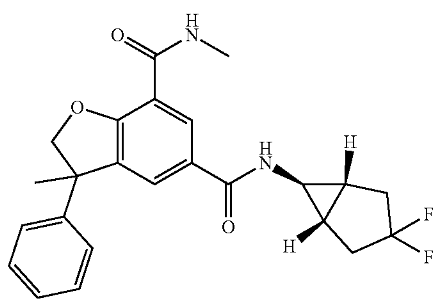 [SMILES: CNC(=O)c1cc(C(=O)N[C@H]2[C@@H]3CC(F)(F)C[C@@H]32)cc2c1OCC2(C)c1ccccc1] | (+/−) N$^5$-((1R,5S,6r)-3,3-difluorobicyclo[3.1.0]hexan-6-yl)-N$^7$,3-dimethyl-3-phenyl-2,3-dihydrobenzofuran-5,7-dicarboxamide (17 mg, 0.040 mmol, yield = 36%) | 1.07 | 427 |
| 40 | 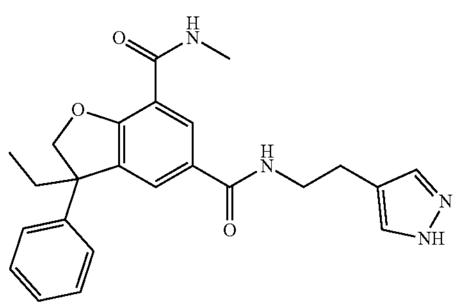 [SMILES: CCC1(c2ccccc2)COc2c(C(=O)NC)cc(C(=O)NCCc3cn[nH]c3)cc21] | (+/−) N$^5$-(2-(1H-pyrazol-4-yl)ethyl)-3-ethyl-N$^7$-methyl-3-phenyl-2,3-dihydrobenzofuran-5,7-dicarboxamide (19 mg, 0.045 mmol, yield = 40%) | 0.88 | 419 |

| Ex. | Structure | Name | Retention time (method formic) | [M + H]+ |
|---|---|---|---|---|
| 41 | 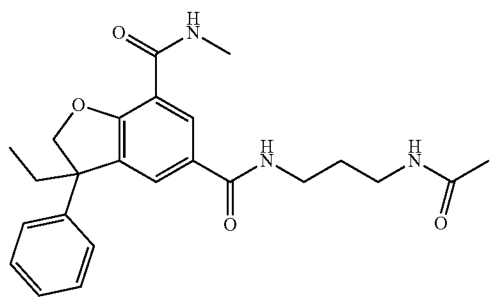 [SMILES: CCC1(c2ccccc2)COc2c(C(=O)NC)cc(C(=O)NCCCNC(C)=O)cc21] | (+/−) $N^5$-(3-acetamidopropyl)-3-ethyl-$N^7$-methyl-3-phenyl-2,3-dihydrobenzofuran-5,7-dicarboxamide (9 mg, 0.021 mmol, yield = 19%) | 0.86 | 424 |
| 42 | 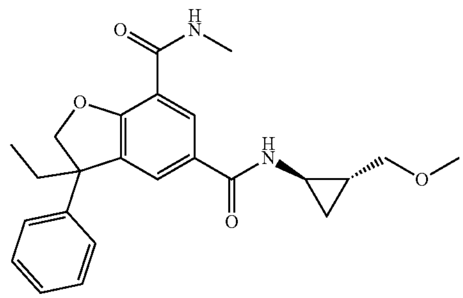 [SMILES: CCC1(c2ccccc2)COc2c(C(=O)NC)cc(C(=O)N[C@@H]3C[C@H]3COC)cc21] | (+/−) 3-ethyl-$N^5$-((1R,2R)-2-(methoxymethyl)cyclopropyl)-$N^7$-methyl-3-phenyl-2,3-dihydrobenzofuran-5,7-dicarboxamide (12 mg, 0.029 mmol, yield 26%) | 0.98 | 409 |
| 43 | 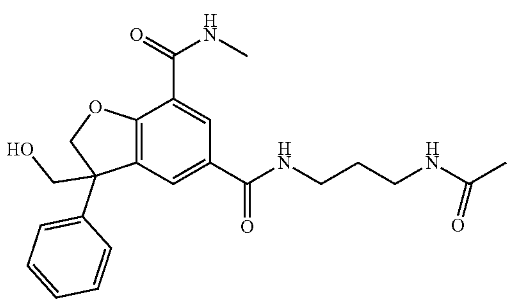 [SMILES: CNC(=O)c1cc(C(=O)NCCCNC(C)=O)cc2c1OCC2(CO)c1ccccc1] | (+/−) $N^5$-(3-acetamidopropyl)-3-(hydroxymethyl)-$N^7$-methyl-3-phenyl-2,3-dihydrobenzofuran-5,7-dicarboxamide (24 mg, 0.055 mmol, yield = 50%) | 0.69 | 426 |
| 44 | 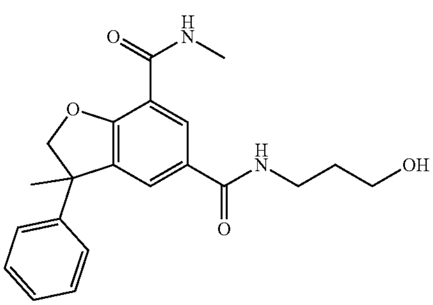 [SMILES: CNC(=O)c1cc(C(=O)NCCCO)cc2c1OCC2(C)c1ccccc1] | (+/−) $N^5$-(3-hydroxypropyl)-$N^7$,3-dimethyl-3-phenyl-2,3-dihydrobenzofuran-5,7-dicarboxamide (11 mg, 0.028 mmol, yield = 26%) | 0.82 | 369 |
| 45 | 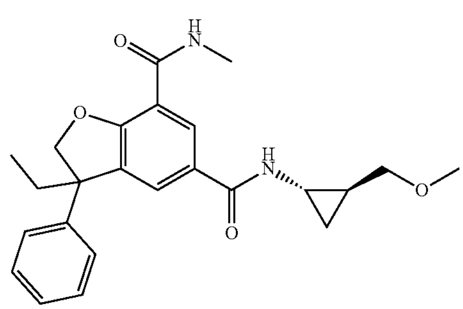 [SMILES: CCC1(c2ccccc2)COc2c(C(=O)NC)cc(C(=O)N[C@H]3C[C@@H]3COC)cc21] | (+/−) 3-ethyl-$N^5$-((1S,2S)-2-(methoxymethyl)cyclopropyl)-$N^7$-methyl-3-phenyl-2,3-dihydrobenzofuran-5,7-dicarboxamide (16 mg, 0.038 mmol, yield 35%) | 0.98 | 409 |

| Ex. | Structure | Name | Retention time (method formic) | [M + H]+ |
|---|---|---|---|---|
| 46 | 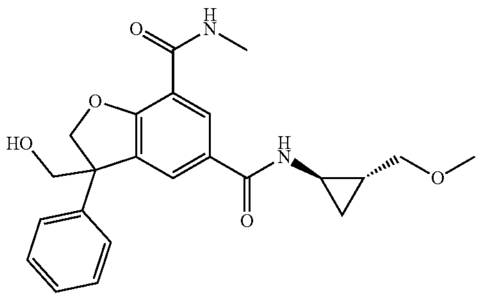 [SMILES: CNC(=O)c1cc(C(=O)N[C@@H]2C[C@H]2COC)cc2c1OCC2(CO)c1ccccc1] | (+/−) 3-(hydroxymethyl)-N$^5$-((1R,2R)-2-(methoxymethyl)cyclopropyl)-N$^7$-methyl-3-phenyl-2,3-dihydrobenzofuran-5,7-dicarboxamide (11 mg, 0.028 mmol, yield 25%) | 0.78 | 411 |
| 47 | 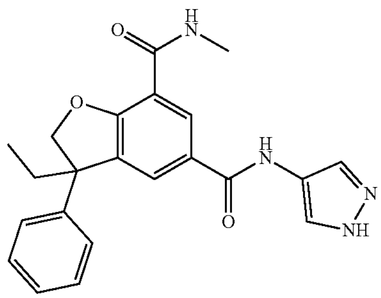 [SMILES: CCC1(c2ccccc2)COc2c(C(=O)NC)cc(C(=O)Nc3cn[nH]c3)cc21] | (+/−) 3-ethyl-N$^7$-methyl-3-phenyl-N$^5$-(1H-pyrazol-4-yl)-2,3-dihydrobenzofuran-5,7-dicarboxamide (25 mg, 0.064 mmol, yield = 57%) | 0.90 | 391 |
| 48 | 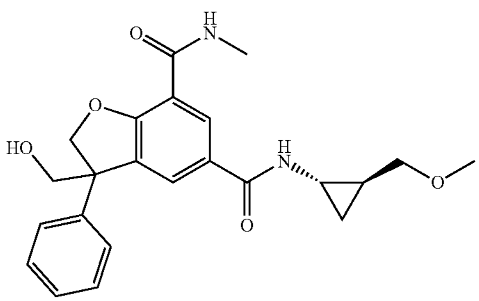 [SMILES: CNC(=O)c1cc(C(=O)N[C@H]2C[C@@H]2COC)cc2c1OCC2(CO)c1ccccc1] | (+/−) 3-(hydroxymethyl)-N$^5$-((1S,2S)-2-(methoxymethyl)cyclopropyl)-N$^7$-methyl-3-phenyl-2,3-dihydrobenzofuran-5,7-dicarboxamide (20 mg, 0.048 mmol, yield 43%) | 0.78 | 411 |
| 49 | 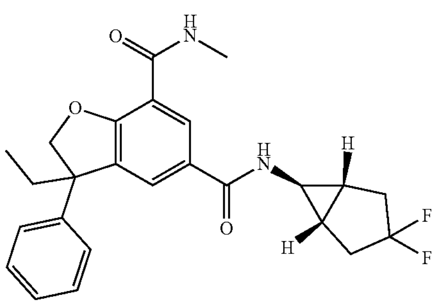 [SMILES: CCC1(c2ccccc2)COc2c(C(=O)NC)cc(C(=O)N[C@H]3[C@@H]4CC(F)(F)C[C@@H]43)cc21] | (+/−) N$^5$-((1R,5S,6r)-3,3-difluorobicyclo[3.1.0]hexan-6-yl)-3-ethyl-N$^7$-methyl-3-phenyl-2,3-dihydrobenzofuran-5,7-dicarboxamide (19 mg, 0.042 mmol, yield = 38%) | 1.12 | 441 |
| 50 | 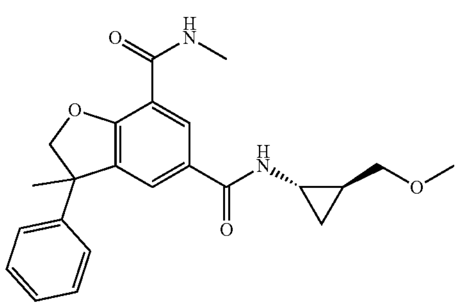 | (+/−) N$^5$-((1S,2S)-2-(methoxymethyl)cyclopropyl)-N$^7$,3-dimethyl-3-phenyl-2,3-dihydrobenzofuran-5,7-dicarboxamide (21 mg, 0.053 mmol, yield = 48%) | 0.93 | 395 |

| Ex. | Structure | Name | Retention time (method formic) | [M + H]+ |
|---|---|---|---|---|
| 51 | 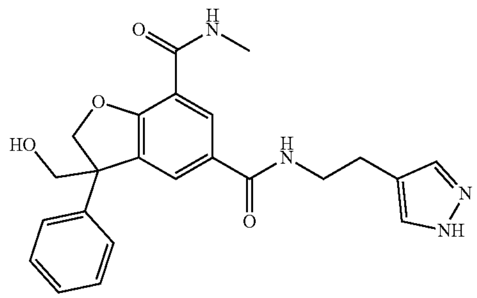 [SMILES: CNC(=O)c1cc(C(=O)NCCc2cn[nH]c2)cc2c1OCC2(CO)c1ccccc1] | (+/−) N⁵-(2-(1H-pyrazol-4-yl)ethyl)-3-(hydroxymethyl)-N⁷-methyl-3-phenyl-2,3-dihydrobenzofuran-5,7-dicarboxamide (17 mg, 0.040 mmol, yield = 36%) | 0.70 | 421 |
| 52 | 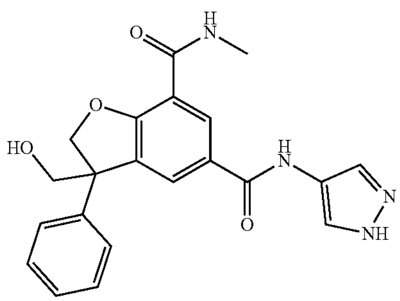 [SMILES: CNC(=O)c1cc(C(=O)Nc2cn[nH]c2)cc2c1OCC2(CO)c1ccccc1] | (+/−) 3-(hydroxymethyl)-N⁷-methyl-3-phenyl-N⁵-(1H-pyrazol-4-yl)-2,3-dihydrobenzofuran-5,7-dicarboxamide (24 mg, 0.062 mmol, yield = 56%) | 0.71 | 393 |
| 53 | 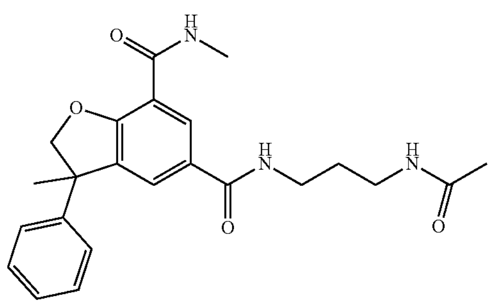 [SMILES: CNC(=O)c1cc(C(=O)NCCCNC(C)=O)cc2c1OCC2(C)c1ccccc1] | (+/−) N⁵-(3-acetamidopropyl)-N⁷,3-dimethyl-3-phenyl-2,3-dihydrobenzofuran-5,7-dicarboxamide (10 mg, 0.025 mmol, yield = 22%) | 0.81 | 410 |

Example 54: (+/−) N⁵-(3-aminopropyl)-3-(hydroxymethyl)-N⁷-methyl-3-phenyl-2,3-dihydrobenzofuran-5,7-dicarboxamide, trifluoroacetic acid salt

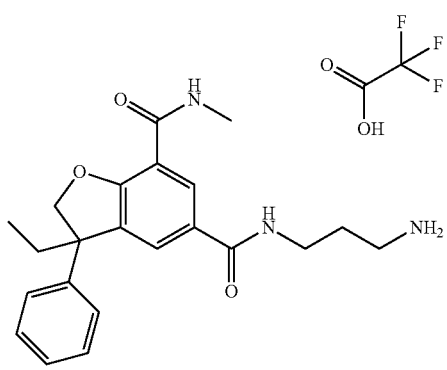 [SMILES: CCC1(c2ccccc2)COc2c(C(=O)NC)cc(C(=O)NCCCN)cc21 ; O=C(O)C(F)(F)F]

A solution of HATU (0.038 g, 0.100 mmol) dissolved in DMF (0.5 mL) and (+/−) 3-(hydroxymethyl)-7-(methylcarbamoyl)-3-phenyl-2,3-dihydrobenzofuran-5-carboxylic acid (0.032 g, 0.100 mmol, Intermediate 16) and DIPEA (0.052 ml, 0.300 mmol) was shaken and was then added to tert-butyl (3-aminopropyl)carbamate (0.021 g, 0.120 mmol). The reaction was allowed to stand at rt for 64h. The reaction was injected as is and purified by MDAP (High pH) to give boc protected title compound which was taken up in DCM (0.5 mL) and treated with TFA (0.5 mL) and stood at rt for 1h. The reaction was then concenrated and dried to give: N⁵-(3-aminopropyl)-3-(hydroxymethyl)-N⁷-methyl-3-phenyl-2,3-dihydrobenzofuran-5,7-dicarboxamide, trifluoroacetic acid salt (12 mg, 0.024 mmol, yield 22%)

LCMS (method formic): Retention time 0.48 min, [M+H]⁺=384

Similarly prepared were the following:

| 55 | 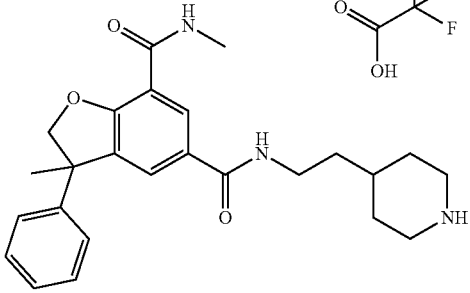 | | (+/−) N[7],3-dimethyl-3-phenyl-N[5]-(2-(piperidin-4-yl)ethyl)-2,3-dihydrobenzofuran-5,7-dicarboxamide 2,2,2-trifluoroacetate (20 mg, 0.037 mmol, yield = 34%) | 0.61 | 422 |
|---|---|---|---|---|---|
| 56 | 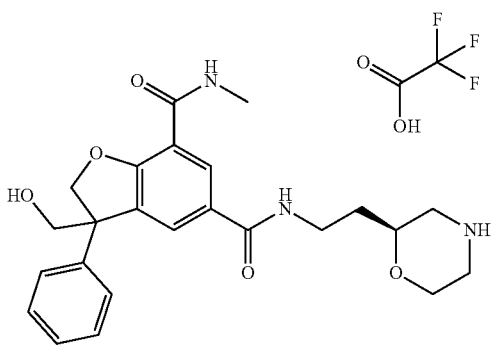 [SMILES: CNC(=O)c1cc(C(=O)NCC[C@H]2CNCCO2)cc2c1OCC2(CO)c1ccccc1 ; O=C(O)C(F)(F)F] | | (+/−) 3-(hydroxymethyl)-N[7]-methyl-N[5]-(2-((S)-morpholin-2-yl)ethyl)-3-phenyl-2,3-dihydrobenzofuran-5,7-dicarboxamide 2,2,2-trifluoroacetate (21 mg, 0.038 mmol, yield = 34%) | 0.50 | 440 |
| 57 | 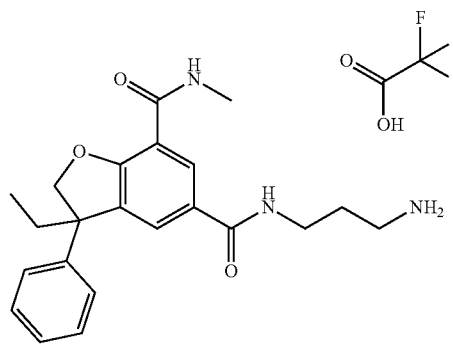 | | (+/−) N[5]-(3-aminopropyl)-3-ethyl-N[7]-methyl-3-phenyl-2,3-dihydrobenzofuran-5,7-dicarboxamide 2,2,2-trifluoroacetate (23 mg, 0.046 mmol, yield = 42%) | 0.61 | 382 |
| 58 | 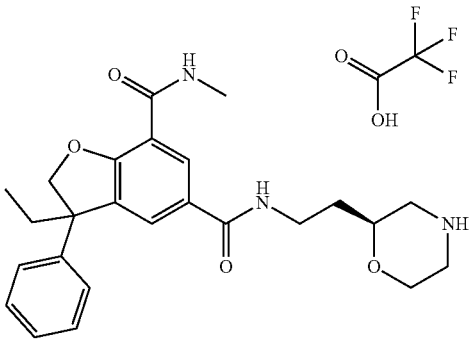 [SMILES: CCC1(c2ccccc2)COc2c(C(=O)NC)cc(C(=O)NCC[C@H]3CNCCO3)cc21 ; O=C(O)C(F)(F)F] | | (+/−) 3-ethyl-N[7]-methyl-N[5]-(2-((S)-morpholin-2-yl)ethyl)-3-phenyl-2,3-dihydrobenzofuran-5,7-dicarboxamide 2,2,2-trifluoroacetate (29 mg, 0.053 mmol, yield = 47%) | 0.63 | 438 |

| # | Structure | Reagent | Name | | |
|---|---|---|---|---|---|
| 59 | 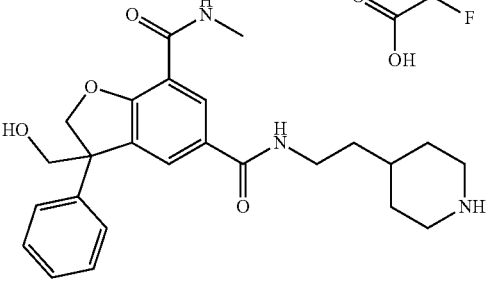 | 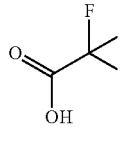 | (+/−) 3-(hydroxymethyl)-$N^7$-methyl-3-phenyl-$N^5$-(2-(piperidin-4-yl)ethyl)-2,3-dihydrobenzofuran-5,7-dicarboxamide 2,2,2-trifluoroacetate (24 mg, 0.044 mmol, yield = 39%) | 0.52 | 438 |
| 60 | 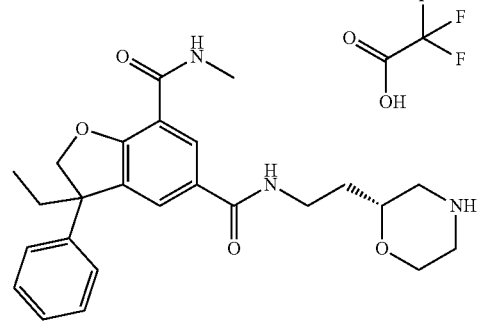 | 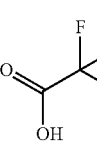 | (+/−) 3-ethyl-$N^7$-methyl-$N^5$-(2-((R)-morpholin-2-yl)ethyl)-3-phenyl-2,3-dihydrobenzofuran-5,7-dicarboxamide 2,2,2-trifluoroacetate (15 mg, 0.027 mmol, yield = 25%) | 0.63 | 438 |
| 61 | 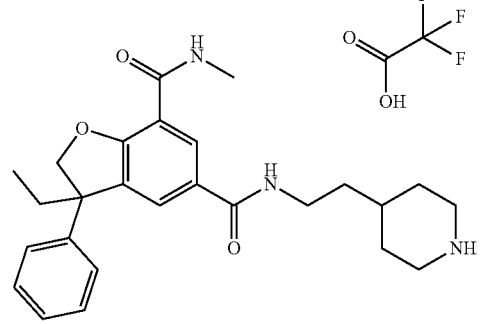 | 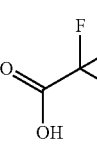 | (+/−) 3-ethyl-$N^7$-methyl-3-phenyl-$N^5$-(2-(piperidin-4-yl)ethyl)-2,3-dihydrobenzofuran-5,7-dicarboxamide 2,2,2-trifluoroacetate (19 mg, 0.035 mmol, yield = 31%) | 0.65 | 436 |
| 62 | 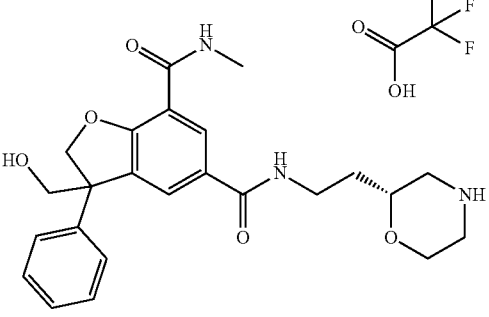 | 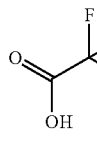 | (+/−) 3-(hydroxymethyl)-$N^7$-methyl-$N^5$-(2-((R)-morpholin-2-yl)ethyl)-3-phenyl-2,3-dihydrobenzofuran-5,7-dicarboxamide 2,2,2-trifluoroacetate (10 mg, 0.018 mmol, yield = 16%) | 0.50 | 440 |

| | | | | | |
|---|---|---|---|---|---|
| 63 | | | (+/−) $N^7$,3-dimethyl-$N^5$-(2-((R)-morpholin-2-yl)ethyl)-3-phenyl-2,3-dihydrobenzofuran-5,7-dicarboxamide 2,2,2-trifluoroacetate (20 mg, 0.037 mmol, yield = 34%) | 0.59 | 424 |
| 64 | | | (+/−) $N^7$,3-dimethyl-$N^5$-(2-((S)-morpholin-2-yl)ethyl)-3-phenyl-2,3-dihydrobenzofuran-5,7-dicarboxamide 2,2,2-trifluoroacetate (29 mg, 0.054 mmol, yield = 49%) | 0.59 | 424 |
| 65 | | | (+/−) $N^5$-(3-aminopropyl)-$N^7$,3-dimethyl-3-phenyl-2,3-dihydrobenzofuran-5,7-dicarboxamide 2,2,2-trifluoroacetate (17 mg, 0.035 mmol, yield = 32%) | 0.57 | 368 |

Biological Data

The compounds of formula (I) may be tested in one or more of the following assays:

Time Resolved Fluorescence Resonance Energy Transfer (TR-FRET) Assay

Bromodomain binding was assessed utilising a time resolved fluorescent resonance energy transfer (TR-FRET) competition assay. To enable this approach a known, high affinity, pan-BET interacting small molecule was labelled with Alexa Fluor® 647, which is a far-red-fluorescent dye (Reference Compound X). Reference Compound X acts as a reporter of bromodomain binding and is the acceptor fluorophore component of the TR-FRET pair. Europium chelate, conjugated to an anti-6*His antibody, was utilised as the donor fluorophore in the TR-FRET pair. The anti-6*His antibody binds selectively to a six Histidine purification epitope added to the amino-terminus of each of the BET tandem bromodomain protein constructs used in this study. A TR-FRET signal is generated when the donor and acceptor fluorophores are in close proximity, between 20-80 Å, which is enabled in this assay by binding of Reference Compound X to the bromodomain protein.

Reference Compound X: 4-((Z)-3-(6-((5-(2-((4S)-6-(4-chlorophenyl)-8-methoxy-1-methyl-4H-benzo[f][1,2,4]triazolo[4,3-a][1,4]diazepin-4-yl)acetamido)pentyl)amino)-6-oxohexyl)-2-((2E,4E)-5-(3,3-dimethyl-5-sulfo-1-(4-sulfobutyl)-3H-indol-1-ium-2-yl)penta-2,4-dien-1-ylidene)-3methyl-5-sulfoindolin-1-yl)butane-1-sulphonate)

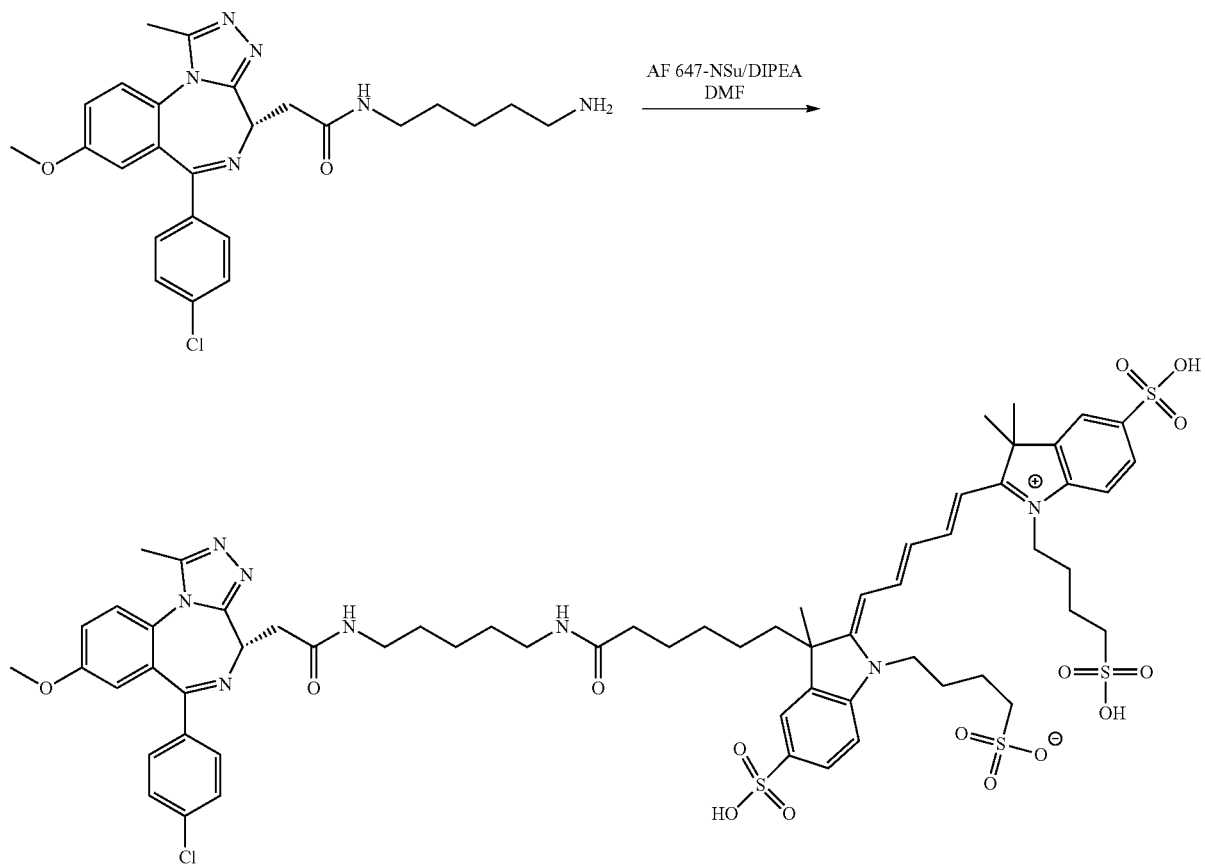

To a solution of N-(5-aminopentyl)-2-((4S)-6-(4-chlorophenyl)-8-methoxy-1-methyl-4H-benzo[f][1,2,4]triazolo[4,3-a][1,4]diazepin-4-yl)acetamide (for a preparation see Reference Compound J, WO2011/054848A1, 1.7 mg, 3.53 µmol) in DMF (40 µl) was added a solution of AlexaFluor647-ONSu (2.16 mg, 1.97 µmol) also in DMF (100 µl). The mixture was basified with DIPEA (1 µl, 5.73 µmol) and agitated overnight on a vortex mixer.

The reaction mixture was evaporated to dryness. The solid was dissolved in acetonitrile/water/acetic acid (5/4/1, <1 ml) filtered and was applied to a Phenomenex Jupiter C18 preparative column and eluted with the following gradient (A=0.1% trifluoroacetic acid in water, B=0.1% TFA/90% acetonitrile/10% water): Flow rate=10 ml/min., AU=20/10 (214 nm):

5-35%, t=0 min: B=5%; t=10 min: B=5%; t=100 min: B=35%; t=115 min: B=100% (Sep. grad: 0.33%/min)

The major component was eluted over the range 26-28% B but appeared to be composed of two peaks. The middle fraction (F1.26) which should contain "both" components was analysed by analytical HPLC (Spherisorb ODS2, 1 to 35% over 60 min): single component eluting at 28% B.

Fractions F1.25/26&27 were combined and evaporated to dryness. Transferred with DMF, evaporated to dryness, triturated with dry ether and the blue solid dried overnight at <0.2 mbar: 1.54 mg.

Analytical HPLC (Sphersisorb ODS2, 1 to 35% B over 60 min): MSM10520-1: [M+H]$^+$ (obs): 661.8/– corresponding with M-29. This equates to [(M+2H)/2]$^+$ for a calculated mass of 1320.984 which is M-29. This is a standard occurrence with the Alexa Fluor 647 dye and represents a theoretical loss of two methylene groups under the conditions of the mass spectrometer.

Assay Principle: In order to generate a TR-FRET signal, donor fluorophore is excited by a laser at λ337 nm, which subsequently leads to emission at λ618 nm. If the acceptor fluorophore is in close proximity then energy transfer can occur, which leads to emission of Alexa Fluor® 647 at λ665 nm. In the presence of competitor compound, Reference Compound X can be displaced from binding to the bromodomain. If displacement occurs, the acceptor fluorophore is no longer in proximity to the donor fluorophore, which prevents fluorescent energy transfer and, subsequently, a loss of Alexa Fluor® 647 emission at λ665 nm.

The competition of the compounds of formula (I) with Reference Compound X for binding to the BET family (BRD2, BRD3, BRD4 and BRDT) was assessed using protein truncates spanning both bromodomain 1 (BD1) and bromodomain 2 (BD2). In order to monitor differential binding to either BD1 or BD2, single residue mutations of key tyrosines to alanine were made in the acetyl lysine binding pockets. To validate this approach, a double residue mutant tandem domain protein was produced for each of the BET family members. Utilising a Fluorescence Polarisation approach, binding affinities for each of the single and double mutants for Reference Compound X were determined. The affinities of the double mutant tandem proteins for Reference Compound X were greatly reduced in comparison to the non mutated, wild type tandem BET proteins (>1000 fold reduction in Kd). The affinities of the single mutated bromdomain tandem proteins for Reference Compound X were equipotent with the corresponding non-mutated BET protein. These data demonstrated that single mutations of Tyrosine to Alanine reduce the Kd of the interaction between the mutated bromodomain and Reference Compound X by >1000 fold. In the TR-FRET competition assay, Reference Compound X is used at a concentration that is equivalent to the Kd for the non-mutated bromodomain, which ensures that no binding at the mutated bromodomain is detected.

Protein production: Recombinant Human Bromodomains [(BRD2 (1-473) (Y113A) and (Y386A), BRD3 (1-435) (Y73A) and (Y348A) BRD4 (1-477) (Y97A) and (Y390A) and BRDT (1-397) (Y66A) and (Y309A)] were expressed in E. coli cells (in pET15b vector for BRD2/3/4 and in pET28a vector for BRDT) with a 6-His tag at the N-terminal. The His-tagged Bromodomain pellet was resuspended in 50 mM HEPES (pH7.5), 300 mM NaCl, 10 mM imidazole & 1 µl/ml protease inhibitor cocktail and extracted from the E. coli cells using sonication and purified using a nickel sepharose high performance column, the proteins were washed and then eluted with a linear gradient of 0-500 mM imidazole with buffer 50 mM HEPES (pH7.5), 150 mM NaCl, 500 mM imidazole, over 20 column volumes. Final purification was completed by Superdex 200 prep grade size exclusion column. Purified protein was stored at −80° C. in 20 mM HEPES pH 7.5 and 100 mM NaCl. Protein identity was confirmed by peptide mass fingerprinting and predicted molecular weight confirmed by mass spectrometry.

Protocol for Bromodomain BRD2, 3, 4 and T, BD1+BD2 Mutant TR-FRET competition assays: All assay components were dissolved in an assay buffer composing of 50 mM HEPES pH7.4, 50 mM NaCl, 5% Glycerol, 1 mM DTT and 1 mM CHAPS. Reference Compound X was diluted, in assay buffer containing 20 nM single mutant, tandem bromodomain protein, to a concentration equivalent to 2*Kd for this bromodomain. The solution containing bromodomain and Reference Compound X was added to dose response dilutions of test compound or DMSO vehicle (a maximum of 0.5% DMSO is used in this assay) in Greiner 384 well black low volume microtitre plates and subsequently incubated for 30 minutes at room temperature. An equal volume of 3 nM of anti-6*His Europium chelate was added to all wells, followed by a further 30 minute incubation at room temperature. TR-FRET was detected using a Perkin Elmer Multimode plate reader, by exciting the donor fluorophore at λ337 nm and subsequently, after a delay of 50 µsecs, measuring emission of the donor and acceptor fluorophores at λ615 nm and λ665 nm, respectively. In order to control these assays, 16 replicates each of uninhibited (DMSO vehicle) and inhibited (10*IC$_{50}$ concentrations of Example 11 of WO 2011/054846A1) TR-FRET assays were included on every microtitre plate.

cA four parameter curve fit of the following form was then applied:

$$y=a+((b-a)/(1+(10^x/10^C)^d)$$

Where 'a' is the minimum, 'b' is the Hill slope, 'c' is the pIC$_{50}$ and 'd' is the maximum.

With the exception of Example 26 all Examples were each tested in the BRD4 BD1 and the BRD4 BD2 TR-FRET assays essentially as described above. Those of skill in the art will recognise that in vitro binding assays and cell-based assays for functional activity are subject to experimental variability. Accordingly, it is to be understood that the pIC$_{50}$ values given below are exemplary only. pIC$_{50}$ values are expressed as log$_{10}$ units.

All tested compounds were found to have a pIC$_{50}$≥5.0 in at least one assay described above.

Examples 3 and 14 were found to have a pIC$_{50}$≥5.0 and <6.0 in the BRD4 BD2 assay.

All other tested compounds were found to have a pIC$_{50}$≥6.0 and <8.0 in the BRD4 BD2 assay.

Example 1 had a mean pIC$_{50}$ of 7.2 in the BRD4 BD2 TR-FRET assay described above, and a mean pIC$_{50}$ of 4.5 in the BRD4 BD1 TR-FRET assay described above.

Example 2 had a mean pIC$_{50}$ of 7.5 in the BRD4 BD2 TR-FRET assay described above, and a mean pIC$_{50}$ of 4.7 in the BRD4 BD1 TR-FRET assay described above.

Example 9 had a mean pIC$_{50}$ of 7.8 in the BRD4 BD2 TR-FRET assay described above, and a mean pIC$_{50}$ of 4.7 in the BRD4 BD1 TR-FRET assay described above.

Example 23 had a mean pIC$_{50}$ of 7.6 in the BRD4 BD2 TR-FRET assay described above, and a mean pIC$_{50}$ of 4.6 in the BRD4 BD1 TR-FRET assay described above.

Calculation of Selectivity for BRD4 BD2 Over BRD4 BD1

Selectivity for BRD4 BD2 over BRD4 BD1 was calculated as follows:

Selectivity=BRD4 BD2 pIC50−BRD4 BD1 pIC50

All tested compounds were found to have selectivity for BRD4 BD2 over BRD4 BD1 of ≥1 log unit in at least one of the TR-FRET assays described above, and hence are at least 10 fold selective for BRD4 BD2 over BRD4 BD1.

Examples 3, 4, 14, 25, 36, 40, 43, 54, 56, 57 and 65 were found to have selectivity for BRD4 BD2 over BRD4 BD1 of ≥1 to <2 log unit in at least one of the TR-FRET assays described above.

All other Examples were found to have selectivity for BRD4 BD2 over BRD4 BD1 of ≥2 log unit in at least one of the TR-FRET assays described above, and hence are at least 100 fold selective for BRD4 BD2 over BRD4 BD1.

Examples 9, 10, 11, 17 and 23 were found to have selectivity for BRD4 BD2 over BRD4 BD1 of ≥3 log units in at least one of the TR-FRET assays described above, and hence is at least 1000-fold selective for BRD4 BD2 over BRD4 BD1.

The invention claimed is:
1. A compound of formula (I)

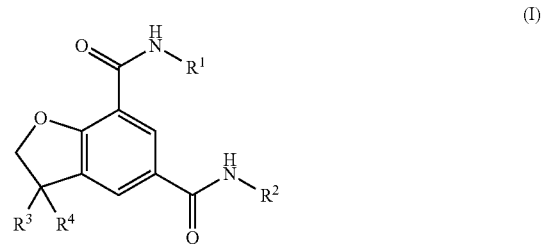

or a pharmaceutically acceptable salt thereof,
wherein:
R$^1$ is —C$_{1-3}$alkyl or cyclopropyl;
R$^2$ is —C$_{0-3}$alkyl-cycloalkyl, wherein the cycloalkyl group is optionally substituted with one, two or three R$^5$ groups which may be the same or different; or
R$^2$ is —C$_{0-4}$alkyl-heterocyclyl or —(CH$_2$)$_p$O-heterocyclyl wherein each heterocyclyl is optionally substituted by one or two R$^9$ groups which may be the same or different; or
R$^2$ is H, —CH$_3$, —C$_{2-6}$alkyl optionally substituted by up to five fluoro, —C$_{2-6}$alkylOR$^{13}$, —C$_{2-6}$alkylNR$^{11}$R$^{12}$, —(CH$_2$)$_m$SO$_2$C$_{1-3}$alkyl, —(CH$_2$)$_m$SO$_2$NR$^{11}$R$^{12}$, —$(CH_2)_mC(O)NR^{11}R^{12}$, —$(CH_2)_mCN$, —$(CH_2)_mCO_2R^{13}$, —$(CH_2)_mNHCO_2C_{1-4}alkyl$ —$(CH_2)_mNHC(O)C_{1-4}alkyl$ or —$(CH_2)_n$heteroaryl, wherein heteroaryl is optionally substituted by one or two $R^{14}$ groups which may be the same or different;

$R^3$ is phenyl optionally substituted with one, two or three $R^7$ groups which may be the same or different;

$R^4$ is —$CH_2OR^6$ or —$C_{1-3}alkyl$ optionally substituted by up to three fluoro;

each $R^5$ is independently halo, —$C_{0-6}alkyl-R^8$, —$O$—$C_{2-6}alkyl-R^8$, —CN or —$SO_2C_{1-3}alkyl$;

$R^6$ is —H or —$C_{1-3}alkyl$;

each $R^7$ is independently -halo, —$C_{1-4}alkyl$, —$C_{0-3}alkyl-OR^{10}$, —$C_{0-3}alkyl-NR^{15}R^{16}$, —$C_{0-3}alkyl-CONR^{15}R^{16}$, —CN or —$SO_2R^{17}$;

$R^8$ is —H, —$OR^{10a}$, —$NR^{18}R^{19}$ or heteroaryl;

each $R^9$ is independently halo, $C_{1-4}alkyl$, cyclopropyl, cyclobutyl, —$CH_2CF_3$, —$CH_2CHF_2$, —$CH_2CH_2F$, —$OCH_2CH_2OR^{13}$, —$C_{0-3}alkylOR^{13}$, —$C_{0-3}alkylNR^{11}R^{12}$, —$NHCH_2CH_2OR^{13}$, —$NHCO_2R^{13}$, oxo, —$C(O)R^{13}$, —$C(O)OR^{13}$ or —$C(O)NR^{11}R^{12}$;

$R^{10a}$ is —H, —$C_{1-3}alkyl$, —$C_{2-3}alkylNR^{11}R^{12}$ or —$C_{2-3}alkylOH$;

$R^{10}$ is —H, —$C_{1-3}alkyl$, —$C_{2-3}alkylNR^{15}R^{16}$ or —$C_{2-3}alkylOH$;

$R^{11}$ and $R^{12}$ are each independently selected from —H and —$C_{1-3}alkyl$; or $R^{11}$ and $R^{12}$ may join together with the nitrogen to which they are attached, to form a 4 to 7-membered heterocyclyl group optionally substituted by one or two substituents independently selected from —$C_{1-3}alkyl$, —OH and F;

$R^{13}$ is —H or —$C_{1-4}alkyl$;

each $R^{14}$ is independently halo, $C_{1-4}alkyl$, cyclopropyl, cyclobutyl or —$OR^{13}$;

$R^{15}$ and $R^{16}$ are each independently selected from —H and —$C_{1-3}alkyl$;

or $R^{15}$ and $R^{16}$ may join together with the nitrogen to which they are attached, to form a 4 to 7-membered heterocyclyl group optionally substituted by one or two substituents independently selected from —$C_{1-3}alkyl$, —OH and F;

$R^{17}$ is —$C_{1-3}alkyl$ or —$NR^{15}R^{16}$;

$R^{18}$ and $R^{19}$ are each independently selected from —H, —$C(O)OC(CH_3)_3$, —$C_{1-6}alkyl$, cycloalkyl, heterocyclyl, —$C_{2-3}alkylNR^{13}COC_{1-3}alkyl$, —$C_{2-3}alkylNR^{15}R^{16}$ and —$C_{2-3}alkyl-O-C_{1-3}alkyl$ wherein the —$C_{1-6}alkyl$ and cycloalkyl may be optionally substituted by one, two or three fluoro; or $R^{18}$ and $R^{19}$ may join together with the nitrogen to which they are attached, to form a 4 to 7-membered heterocyclyl group optionally substituted by one or two substituents independently selected from —$C_{1-3}alkyl$, —OH and F;

m is an integer selected from 2, 3 and 4;

p is an integer selected from 2, 3 and 4; and n is an integer selected from 0, 1, 2, 3 and 4.

2. The compound or pharmaceutically acceptable salt thereof according to claim 1, wherein the compound of formula (I) is a compound of formula (IA) or (IB):

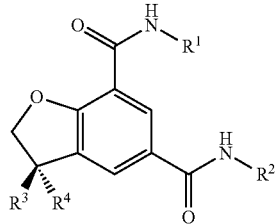

(IA)

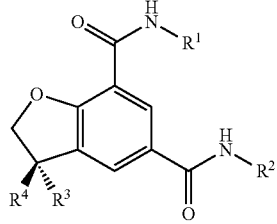

(IB)

wherein $R^1$, $R^2$, $R^3$ and $R^4$ are defined according to formula (I).

3. The compound or pharmaceutically acceptable salt thereof according to claim 1, wherein $R^1$ is methyl.

4. The compound or pharmaceutically acceptable salt thereof according to claim 1, wherein $R^2$ is —$C_{0-3}alkyl-C_{3-7}$cycloalkyl and the $C_{3-7}$cycloalkyl group is optionally substituted with one, two or three $R^5$ groups which may be the same or different.

5. The compound or pharmaceutically acceptable salt thereof according to claim 4, wherein $R^2$ is cyclopropyl, cyclobutyl, cyclohexyl or bicyclo[3.1.0]hexanyl, wherein any said cyclopropyl, cyclobutyl, cyclohexyl or bicyclo[3.1.0]hexanyl is optionally substituted with one, two or three $R^5$ groups which may be the same or different.

6. The compound or pharmaceutically acceptable salt thereof according to claim 5, wherein $R^5$ is —$C_{0-6}alkyl-R^8$.

7. The compound or pharmaceutically acceptable salt thereof according to claim 1, wherein $R^2$ is —$C_{0-4}alkyl$-heterocyclyl, and heterocyclyl is optionally substituted by one or two $R^9$ groups which may be the same or different.

8. The compound or pharmaceutically acceptable salt thereof according to claim 7, wherein $R^2$ is heterocyclyl, —$CH_2CH_2$-heterocyclyl or —$CH_2CH_2CH_2$-heterocyclyl.

9. The compound or pharmaceutically acceptable salt thereof according to claim 7, wherein the heterocyclyl is selected from oxetanyl, tetrahydrofuranyl, tetrahydro-2H-pyranyl, morpholinyl, piperidinyl, piperazinyl, (1r,5s)-3-oxabicyclo[3.1.0]hexanyl and (1r,5s)-3-azabicyclo[3.1.0]hexanyl optionally substituted by one or two $R^9$ groups which may be the same or different.

10. The compound or pharmaceutically acceptable salt thereof according to claim 7, wherein the heterocyclyl is optionally substituted by one or two $R^9$ groups selected from methyl, —$C(O)CH_3$, —$NH_2$ and fluoro.

11. The compound or pharmaceutically acceptable salt thereof according to claim 7, wherein the heterocyclyl optionally substituted by one or two $R^9$ groups is:

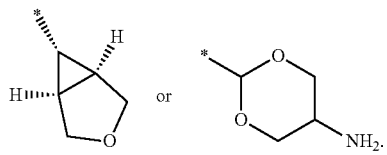

* denotes point of attachment

12. The compound or pharmaceutically acceptable salt thereof according to claim 1, wherein $R^2$ is —H, —$CH_3$, $C_{2-6}$alkyl optionally substituted by up to five fluoro, —$C_{2-6}$alkylOR$^{13}$, —$C_{2-6}$alkylNR$^{11}$R$^{12}$, —$(CH_2)_m SO_2 C_{1-3}$alkyl, —$(CH_2)_m C(O)NR^{11}R^{12}$, —$(CH_2)_m CN$, —$(CH_2)_m CO_2 R^{13}$, —$(CH_2)_m NHCO_2 C(CH_3)_3$ or —$(CH_2)_n C_{5-6}$heteroaryl, and wherein $C_{5-6}$heteroaryl is optionally substituted by one or two $R^{14}$ groups which may be the same or different.

13. The compound or pharmaceutically acceptable salt thereof according to claim 12, wherein $R^2$ is —H, —$CH_3$, $C_{2-6}$alkyl, —$C_{2-6}$alkylOR$^{13}$, —$C_{2-6}$alkylNR$^{11}$R$^{12}$ or —$(CH_2)_n C_{5-6}$heteroaryl.

14. The compound or pharmaceutically acceptable salt thereof according to claim 13, wherein $R^2$ is —H, methyl, ethyl, propyl, —$CH_2CH_2OH$, —$CH_2CH_2CH_2OH$, —$CH_2CH(CH_3)OH$, —$CH_2CH_2OCH_3$, —$CH_2CH_2CH_2OCH_3$, —$CH_2CH_2N(CH_3)_2$, —$CH_2CH_2CH_2N(CH_3)_2$, —$CH_2CHF_2$ or —$CH_2CH_2$pyridinyl.

15. The compound or pharmaceutically acceptable salt thereof according to claim 1, wherein $R^3$ is phenyl optionally substituted by —$OCH_3$ or —$OCH_2CH_2OH$.

16. The compound or pharmaceutically acceptable salt thereof according to claim 1, wherein $R^4$ is methyl, ethyl or —$CH_2OH$.

17. The compound or pharmaceutically acceptable salt thereof according to claim 1, wherein the compound is selected from:
- (+/−)-N$^5$-((1R,5S,6r)-3-oxabicyclo[3.1.0]hexan-6-yl)-N$^7$,3-dimethyl-3-phenyl-2,3-dihydrobenzofuran-5,7-dicarboxamide;
- (S*)—N$^5$-((1R,5S,6r)-3-oxabicyclo[3.1.0]hexan-6-yl)-N$^7$,3-dimethyl-3-phenyl-2,3-dihydrobenzofuran-5,7-dicarboxamide compound;
- (R*)—N5-((1R,5S,6r)-3-oxabicyclo[3.1.0]hexan-6-yl)-N$^7$,3-dimethyl-3-phenyl-2,3-dihydrobenzofuran-5,7-dicarboxamide;
- (S*)—N$^5$,N$^7$,3-Trimethyl-3-phenyl-2,3-dihydrobenzofuran-5,7-dicarboxamide;
- (S*)—N$^5$-Ethyl-N7,3-dimethyl-3-phenyl-2,3-dihydrobenzofuran-5,7-dicarboxamide;
- (S*)—N$^5$-Cyclopropyl-N7,3-dimethyl-3-phenyl-2,3-dihydrobenzofuran-5,7-dicarboxamide;
- (S*)—N$^5$-((1r,4S)-4-Hydroxycyclohexyl)-N$^7$,3-dimethyl-3-phenyl-2,3-dihydrobenzofuran-5,7-dicarboxamide;
- (S*)—N7,3-Dimethyl-N$^5$-((1S,2S)-2-methylcyclopropyl)-3-phenyl-2,3-dihydrobenzofuran-5,7-dicarboxamide;
- (S*)—N$^5$-((1R,3R,5S,6r)-3-hydroxybicyclo[3.1.0]hexan-6-yl)-N$^7$,3-dimethyl-3-phenyl-2,3-dihydrobenzofuran-5,7-dicarboxamide;
- (S*)—N$^5$-((1R,3S,5S,6r)-3-hydroxybicyclo[3.1.0]hexan-6-yl)-N$^7$,3-dimethyl-3-phenyl-2,3-dihydrobenzofuran-5,7-dicarboxamide;
- (S*)—N$^5$-(3-((2r,5S)-5-amino-1,3-dioxan-2-yl)propyl)-N$^7$,3-dimethyl-3-phenyl-2,3-dihydrobenzofuran-5,7-dicarboxamide;
- (S*)—N$^5$-(2-((2r,5S)-5-amino-1,3-dioxan-2-yl)ethyl)-N$^7$,3-dimethyl-3-phenyl-2,3-dihydrobenzofuran-5,7-dicarboxamide;
- (+/−)-N$^5$-((1R,5S,6r)-3-Oxabicyclo[3.1.0]hexan-6-yl)-3-(hydroxymethyl)-N$^7$-methyl-3-phenyl-2,3-dihydrobenzofuran-5,7-dicarboxamide;
- (S*)—N$^5$-((1R,5S,6r)-3-oxabicyclo[3.1.0]hexan-6-yl)-3-(hydroxymethyl)-N$^7$-methyl-3-phenyl-2,3-dihydrobenzofuran-5,7-dicarboxamide;
- (R*)—N$^5$-((1R,5S,6r)-3-oxabicyclo[3.1.0]hexan-6-yl)-3-(hydroxymethyl)-N$^7$-methyl-3-phenyl-2,3-dihydrobenzofuran-5,7-dicarboxamide;
- (S*)—N$^5$-((1R,3R,5S,6r)-3-hydroxybicyclo[3.1.0]hexan-6-yl)-3-(hydroxymethyl)-N$^7$-methyl-3-phenyl-2,3-dihydrobenzofuran-5,7-dicarboxamide;
- (S*)—N$^5$-((1R,3S,5S,6r)-3-hydroxybicyclo[3.1.0]hexan-6-yl)-3-(hydroxymethyl)-N$^7$-methyl-3-phenyl-2,3-dihydrobenzofuran-5,7-dicarboxamide;
- (+/−)-3-(Hydroxymethyl)-N$^7$-methyl-N$^5$-((1S,2S)-2-methylcyclopropyl)-3-phenyl-2,3-dihydrobenzofuran-5,7-dicarboxamide;
- (S*)-3-(Hydroxymethyl)-N$^5$,N7-dimethyl-3-phenyl-2,3-dihydrobenzofuran-5,7-dicarboxamide;
- (S*)—N$^5$-Ethyl-3-(hydroxymethyl)-N$^7$-methyl-3-phenyl-2,3-dihydrobenzofuran-5,7-dicarboxamide;
- (S*)—N$^5$-Cyclopropyl-3-(hydroxymethyl)-N$^7$-methyl-3-phenyl-2,3-dihydrobenzofuran-5,7-dicarboxamide;
- (S*)—N$^5$-((1r,4S)-4-Hydroxycyclohexyl)-3-(hydroxymethyl)-N$^7$-methyl-3-phenyl-2,3-dihydrobenzofuran-5,7-dicarboxamide;
- (S*)-3-(Hydroxymethyl)-N7-methyl-N$^5$-((1S,2S)-2-methylcyclopropyl)-3-phenyl-2,3-dihydrobenzofuran-5,7-dicarboxamide;
- (S*)—N$^5$-((1R,5S,6r)-3-Oxabicyclo[3.1.0]hexan-6-yl)-3-ethyl-N7-methyl-3-phenyl-2,3-dihydrobenzofuran-5,7-dicarboxamide;
- (S*)-3-Ethyl-N$^5$,N$^7$-dimethyl-3-phenyl-2,3-dihydrobenzofuran-5,7-dicarboxamide;
- (S*)—N$^5$-Cyclopropyl-3-ethyl-N$^7$-methyl-3-phenyl-2,3-dihydrobenzofuran-5,7-dicarboxamide;
- (S*)-3-Ethyl-N$^7$-methyl-N$^5$-((1S,2S)-2-methylcyclopropyl)-3-phenyl-2,3-dihydrobenzofuran-5,7-dicarboxamide;
- (S*)-3-Ethyl-N$^5$-((1r,4S)-4-hydroxycyclohexyl)-N$^7$-methyl-3-phenyl-2,3-dihydrobenzofuran-5,7-dicarboxamide;
- (S*)-3-Ethyl-N-((1R,3R,5S,6r)-3-hydroxybicyclo[3.1.0]hexan-6-yl)-N$^7$-methyl-3-phenyl-2,3-dihydrobenzofuran-5,7-dicarboxamide;
- (S*)—N$^5$-(2-((2r,5S)-5-amino-1,3-dioxan-2-yl)ethyl)-3-ethyl-N-methyl-3-phenyl-2,3-dihydrobenzofuran-5,7-dicarboxamide;
- (S*)—N$^5$-(3-((2r,5S)-5-Amino-1,3-dioxan-2-yl)propyl)-3-ethyl-N$^7$-methyl-3-phenyl-2,3-dihydrobenzofuran-5,7-dicarboxamide;
- (+/−) 3-ethyl-N$^5$-(3-hydroxypropyl)-N$^7$-methyl-3-phenyl-2,3-dihydrobenzofuran-5,7-dicarboxamide;
- (+/−) N$^5$-((1R,2R)-2-(methoxymethyl)cyclopropyl)-N$^7$,3-dimethyl-3-phenyl-2,3-dihydrobenzofuran-5,7-dicarboxamide;
- (+/−) N$^5$-(2-(1H-pyrazol-4-yl)ethyl)-N$^7$,3-dimethyl-3-phenyl-2,3-dihydrobenzofuran-5,7-dicarboxamide;
- (+/−) 3-(hydroxymethyl)-N$^5$-(3-hydroxypropyl)-N$^7$-methyl-3-phenyl-2,3-dihydrobenzofuran-5,7-dicarboxamide;
- (+/−) N$^7$,3-dimethyl-3-phenyl-N$^5$-(1H-pyrazol-4-yl)-2,3-dihydrobenzofuran-5,7-dicarboxamide;
- (+/−) N$^5$-((1R,5S,6r)-3,3-difluorobicyclo[3.1.0]hexan-6-yl)-3-(hydroxymethyl)-N$^7$-methyl-3-phenyl-2,3-dihydrobenzofuran-5,7-dicarboxamide;
- (+/−) N$^5$-((1R,5S,6r)-3,3-difluorobicyclo[3.1.0]hexan-6-yl)-N$^7$,3-dimethyl-3-phenyl-2,3-dihydrobenzofuran-5,7-dicarboxamide;
- (+/−) N$^5$-(2-(1H-pyrazol-4-yl)ethyl)-3-ethyl-N$^7$-methyl-3-phenyl-2,3-dihydrobenzofuran-5,7-dicarboxamide;

(+/−) $N^5$-(3-acetamidopropyl)-3-ethyl-$N^7$-methyl-3-phenyl-2,3-dihydrobenzofuran-5,7-dicarboxamide;

(+/−) 3-ethyl-$N^5$-((1R,2R)-2-(methoxymethyl)cyclopropyl)-$N^7$-methyl-3-phenyl-2,3-dihydrobenzofuran-5,7-dicarboxamide;

(+/−) $N^5$-(3-acetamidopropyl)-3-(hydroxymethyl)-$N^7$-methyl-3-phenyl-2,3-dihydrobenzofuran-5,7-dicarboxamide;

(+/−) $N^5$-(3-hydroxypropyl)-$N^7$,3-dimethyl-3-phenyl-2,3-dihydrobenzofuran-5,7-dicarboxamide;

(+/−) 3-ethyl-$N^5$-((1S,2S)-2-(methoxymethyl)cyclopropyl)-$N^7$-methyl-3-phenyl-2,3-dihydrobenzofuran-5,7-dicarboxamide;

(+/−) 3-(hydroxymethyl)-$N^5$-((1R,2R)-2-(methoxymethyl)cyclopropyl)-$N^7$-methyl-3-phenyl-2,3-dihydrobenzofuran-5,7-dicarboxamide;

(+/−) 3-ethyl-$N^7$-methyl-3-phenyl-$N^5$-(1H-pyrazol-4-yl)-2,3-dihydrobenzofuran-5,7-dicarboxamide;

(+/−) 3-(hydroxymethyl)-$N^5$-((1S,2S)-2-(methoxymethyl)cyclopropyl)-$N^7$-methyl-3-phenyl-2,3-dihydrobenzofuran-5,7-dicarboxamide;

(+/−) $N^5$-((1R,5S,6r)-3,3-difluorobicyclo[3.1.0]hexan-6-yl)-3-ethyl-$N^7$-methyl-3-phenyl-2,3-dihydrobenzofuran-5,7-dicarboxamide;

(+/−) $N^5$-((1S,2S)-2-(methoxymethyl)cyclopropyl)-$N^7$,3-dimethyl-3-phenyl-2,3-dihydrobenzofuran-5,7-dicarboxamide;

(+/−) $N^5$-(2-(1H-pyrazol-4-yl)ethyl)-3-(hydroxymethyl)-$N^7$-methyl-3-phenyl-2,3-dihydrobenzofuran-5,7-dicarboxamide;

(+/−) 3-(hydroxymethyl)-$N^7$-methyl-3-phenyl-$N^5$-(1H-pyrazol-4-yl)-2,3-dihydrobenzofuran-5,7-dicarboxamide;

(+/−) $N^5$-(3-acetamidopropyl)-$N^7$,3-dimethyl-3-phenyl-2,3-dihydrobenzofuran-5,7-dicarboxamide;

(+/−) $N^5$-(3-aminopropyl)-3-(hydroxymethyl)-$N^7$-methyl-3-phenyl-2,3-dihydrobenzofuran-5,7-dicarboxamide, trifluoroacetic acid salt;

(+/−) $N^7$,3-dimethyl-3-phenyl-$N^5$-(2-(piperidin-4-yl)ethyl)-2,3-dihydrobenzofuran-5,7-dicarboxamide;

(+/−) 3-(hydroxymethyl)-$N^7$-methyl-$N^5$-(2-((S)-morpholin-2-yl)ethyl)-3-phenyl-2,3-dihydrobenzofuran-5,7-dicarboxamide 2,2,2-trifluoroacetate;

(+/−) $N^5$-(3-aminopropyl)-3-ethyl-$N^7$-methyl-3-phenyl-2,3-dihydrobenzofuran-5,7-dicarboxamide 2,2,2-trifluoroacetate;

(+/−) 3-ethyl-$N^7$-methyl-$N^5$-(2-((S)-morpholin-2-yl)ethyl)-3-phenyl-2,3-dihydrobenzofuran-5,7-dicarboxamide 2,2,2-trifluoroacetate;

(+/−) 3-(hydroxymethyl)-$N^7$-methyl-3-phenyl-$N^5$-(2-(piperidin-4-yl)ethyl)-2,3-dihydrobenzofuran-5,7-dicarboxamide 2,2,2-trifluoroacetate;

(+/−) 3-ethyl-$N^7$-methyl-$N^5$-(2-((R)-morpholin-2-yl)ethyl)-3-phenyl-2,3-dihydrobenzofuran-5,7-dicarboxamide 2,2,2-trifluoroacetate;

(+/−) 3-ethyl-$N^7$-methyl-3-phenyl-$N^5$-(2-(piperidin-4-yl)ethyl)-2,3-dihydrobenzofuran-5,7-dicarboxamide 2,2,2-trifluoroacetate;

(+/−) 3-(hydroxymethyl)-$N^7$-methyl-$N^5$-(2-((R)-morpholin-2-yl)ethyl)-3-phenyl-2,3-dihydrobenzofuran-5,7-dicarboxamide 2,2,2-trifluoroacetate;

(+/−) $N^7$,3-dimethyl-$N^5$-(2-((R)-morpholin-2-yl)ethyl)-3-phenyl-2,3-dihydrobenzofuran-5,7-dicarboxamide 2,2,2-trifluoroacetate;

(+/−) $N^7$,3-dimethyl-$N^5$-(2-((S)-morpholin-2-yl)ethyl)-3-phenyl-2,3-dihydrobenzofuran-5,7-dicarboxamide 2,2,2-trifluoroacetate; and (+/−) $N^5$-(3-aminopropyl)-$N^7$,3-dimethyl-3-phenyl-2,3-dihydrobenzofuran-5,7-dicarboxamide 2,2,2-trifluoroacetate;

or a pharmaceutically acceptable salt thereof.

18. A pharmaceutical composition comprising the compound or pharmaceutically acceptable salt thereof according to claim 1 and one or more pharmaceutically acceptable excipients.

* * * * *